United States Patent
Rando et al.

(10) Patent No.: US 11,299,733 B2
(45) Date of Patent: Apr. 12, 2022

(54) PROCESS OF DELIVERING SMALL RNAS TO SPERM

(71) Applicant: UNIVERSITY OF MASSACHUSETTS, Boston, MA (US)

(72) Inventors: Oliver Rando, Natick, MA (US); Upasna Sharma, Shrewsbury, MA (US); Colin Conine, Brighton, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 20 days.

(21) Appl. No.: 16/315,004

(22) PCT Filed: Jul. 12, 2017

(86) PCT No.: PCT/US2017/041647
§ 371 (c)(1),
(2) Date: Jan. 3, 2019

(87) PCT Pub. No.: WO2018/013640
PCT Pub. Date: Jan. 18, 2018

(65) Prior Publication Data
US 2019/0309294 A1 Oct. 10, 2019

Related U.S. Application Data

(60) Provisional application No. 62/363,174, filed on Jul. 15, 2016.

(51) Int. Cl.
| | |
|---|---|
| C12N 15/113 | (2010.01) |
| C12N 5/076 | (2010.01) |
| C12N 15/11 | (2006.01) |
| A61B 17/43 | (2006.01) |
| A61B 17/435 | (2006.01) |
| A61D 19/02 | (2006.01) |
| A61D 19/04 | (2006.01) |
| A61K 9/00 | (2006.01) |
| A61K 9/06 | (2006.01) |
| C12N 5/073 | (2010.01) |

(52) U.S. Cl.
CPC ............ *C12N 15/113* (2013.01); *A61B 17/43* (2013.01); *A61B 17/435* (2013.01); *A61D 19/02* (2013.01); *A61D 19/04* (2013.01); *A61K 9/0034* (2013.01); *A61K 9/06* (2013.01); *C12N 5/061* (2013.01); *C12N 5/0604* (2013.01); *C12N 15/111* (2013.01); *C12N 2310/14* (2013.01); *C12N 2310/141* (2013.01); *C12N 2320/30* (2013.01); *C12N 2501/65* (2013.01); *C12N 2510/00* (2013.01)

(58) Field of Classification Search
CPC ...... A61D 19/04; A61D 19/00; C12N 15/113; C12N 5/061; C12N 2310/14; C12N 2310/141; C12N 2501/65
See application file for complete search history.

(56) References Cited

U.S. PATENT DOCUMENTS

| | | | |
|---|---|---|---|
| 6,899,863 B1 | 5/2005 | Dhellin et al. | |
| 2002/0193350 A1* | 12/2002 | Ellington | ............... A01N 1/021 514/100 |
| 2005/0025847 A1 | 2/2005 | Camus-Bablon et al. | |
| 2005/0210541 A1* | 9/2005 | DeLeon | ............... C12N 9/2408 800/21 |
| 2011/0177054 A1 | 7/2011 | Gibbings et al. | |
| 2015/0024497 A1 | 1/2015 | Hyde et al. | |
| 2015/0190632 A1 | 7/2015 | Raviv et al. | |

FOREIGN PATENT DOCUMENTS

| | | |
|---|---|---|
| EP | 2 407 539 A1 | 1/2012 |
| WO | WO 2007/091269 A2 | 8/2007 |
| WO | WO 2015/161184 A1 | 10/2015 |
| WO | WO 2016/161374 A1 | 10/2016 |
| WO | WO 2016/205410 A2 | 12/2016 |

OTHER PUBLICATIONS

Eaton et al (Epigenomics (2015) 7(7), 1165-1171) (Year: 2015).*
Gapp (Nature Neuroscience 17(5):667-669, 2014) (Year: 2014).*
Grandjean et al (Sci Rep 5, 18193, published Dec. 15, 2015) (Year: 2015).*
Chen et al (Science 351(6271): 397-400, 2016) (Year: 2016).*
Gapp et al (Cell Research 26(4): 395-396, 2016) (Year: 2016).*
Yuan et al., (Development 143, 635-647, ePub Dec. 30, 2015) (Year: 2015).*
Reilly et al (Sci. Rep. 6:31794, Aug. 23, 2016) (Year: 2016).*
Frenette et al. (Biology of Reproduction 75:885-890, 2006) (Year: 2006).*
Sharma, et al., "Biogenesis and function of Trna fragments during sperm maturation and fertilization in mammals," Science, Jan. 22, 2016 (Jan. 22, 2016), vol. 351, pp. 391-396.
Dias, et al., "Epigenetic mechanisms underlying learning and the inheritance of learned behaviors", Trends Neurosci, Dec. 24, 2014, vol. 38, pp. 96-107.

(Continued)

*Primary Examiner* — Richard A Schnizer
(74) *Attorney, Agent, or Firm* — Lathrop GPM LLP; James H. Velema, Esq.; Michael Spellberg, Esq.

(57) ABSTRACT

Methods and compositions directed to altering a population of sRNAs in a sperm using vesicles isolated from an epididymosome are provided. Methods and compositions directed to altering a population of sRNAs in an oocyte using vesicles isolated from an epididymosome are also provided. Methods for altering an sRNA population in a sperm or an oocyte can be used to prevent, or reduce the severity of, a disease, disorder, or condition that would otherwise be inherited by progeny. For example, certain epigenetic inherited conditions due to paternal effects, such as certain metabolic and stress disorders and conditions, can be ameliorated in progeny using sperm or oocytes having an altered sRNA population.

13 Claims, 48 Drawing Sheets
Specification includes a Sequence Listing.

(56) References Cited

OTHER PUBLICATIONS

Carone, et al., "Paternally Induced Transgenerational Environmental Reprogramming of Metabolic Gene Expression in Mammals," Cell, Dec. 23, 2010, vol. 143, pp. 1084-1096.

Rodgers, et al., "Transgenerational epigenetic programming via sperm micro RNA recapitulates effects of paternal stress", Proceedings of the National Academy of Sciences USA, Nov. 3, 2015, vol. 112, No. 44, pp. 13699-13704.

International Search Report and Written Opinion dated Nov. 20, 2017 in related PCT Application No. PCT/US2017/041647 (27 pages).

Alterman, et al., "Hydrophobically Modified siRNSs silence Huntingtin mRNA in Primary Neurons and Mouse Brain", Molecular Therapy—Nucleic Acids, vol. 4, No. 12, Dec. 1, 2015.

Mok, et al., "Multimeric small interfering ribonucleic acid for highly efficient sequence-specific gene silencing", Nature Materials, vol. 9, Jan. 24, 2010, pp. 272-278.

Lee, et al., "Small-Interfering RNA (siRNA)—Based Functional Micro- and Nanostructures for Efficient and Selective Gene Silencing", Accounts of Chemical Research, vol. 45, No. 7, Jul. 17, 2012, pp. 1014-1025.

Supplementary European Search Report dated Jul. 31, 2019 in related European Application No. EP 17745083 (7 pages).

* cited by examiner

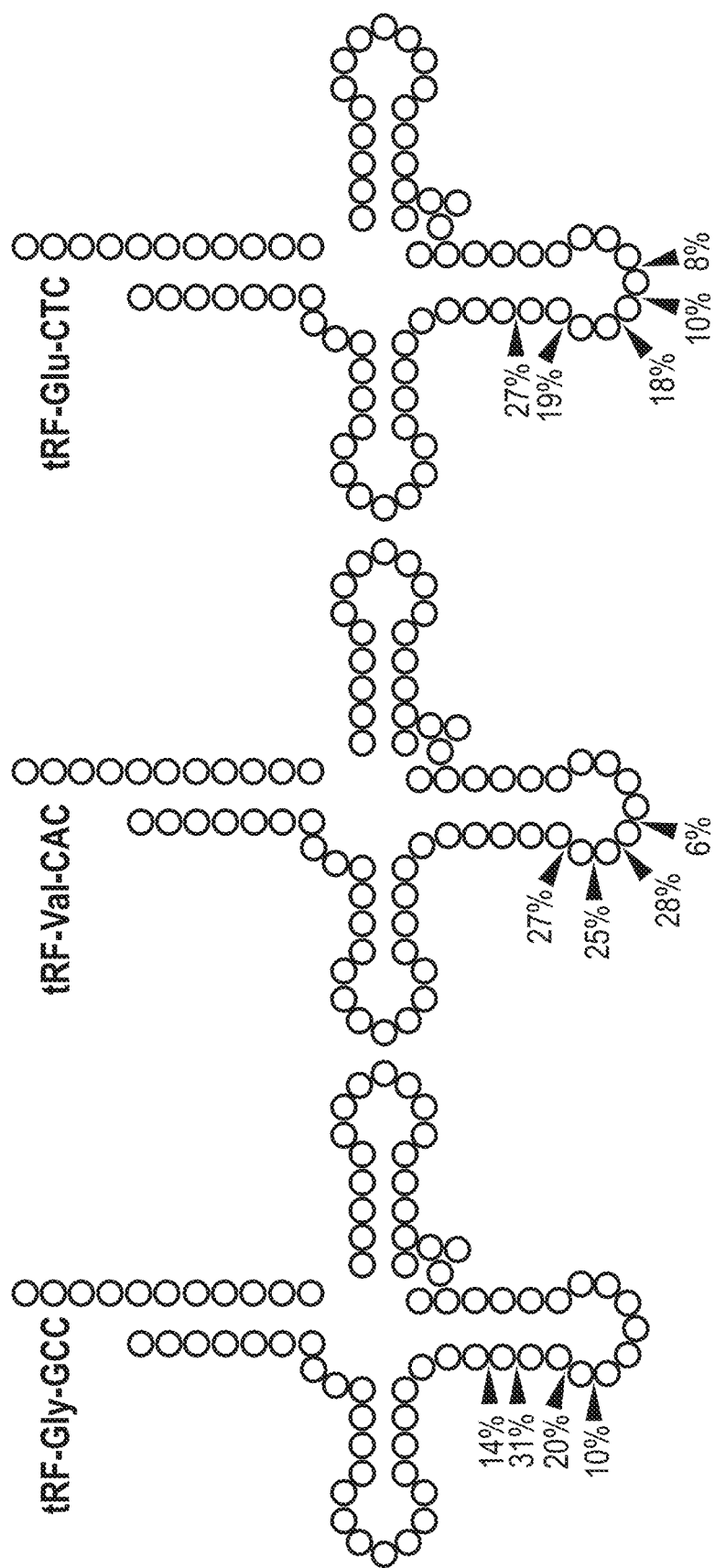

Cauda epididymosomes

Early 2-cell

Late 2-cell

SEQUENCE LISTING

<160> NUMBER OF SEQ ID NOS: 1

<210> SEQ ID NO 1
<211> LENGTH: 30
<212> TYPE: RNA
<213> ORGANISM: Mus musculus

<400> SEQUENCE: 1
gcgagaauuc uaccacugaa ccaccaaugc          30

PROCESS OF DELIVERING SMALL RNAS TO SPERM

RELATED APPLICATIONS

This application is a 35 U.S.C. § 371 filing of International Patent Application No. PCT/US2017/041647, filed Jul. 12, 2017, which claims priority to U.S. Provisional Patent Application Ser. No. 62/363,174, filed Jul. 15, 2016, the contents of which are incorporated herein by reference in their entirety.

STATEMENT REGARDING FEDERALLY SPONSORED RESEARCH

This invention was made with government support under Grant Nos. ES025458 and HD080224 awarded by the National Institutes of Health. The Government has certain rights in the invention.

TECHNICAL FIELD

The disclosed methods and compositions are directed to the field of reproductive biology. Specifically, the disclosed methods and compositions are directed to the delivery of small RNAs to sperm to effectuate changes in sperm RNA content.

BACKGROUND

Mendelian laws of genetics govern most inheritance, and most epigenetic modifications an organism may acquire are reset between generations. However, there has recently been growing evidence to support transgenerational epigenetic inheritance, where some epigenetic phenotypes are maintained through generations (Lim and Brunet, Trends Genet. 2013 29(3):176-186).

For example, animal studies and human cohort studies have suggested that metabolic changes in parents can be inherited epigenetically by offspring. In rats, a high fat diet in male parents affects glucose metabolism in female offspring (Ng et al., Nature 2010; 467: 963-966). Overfeeding male mice also results in the observation of metabolic changes in the two subsequent generations of male offspring (Pentinat et al., Endocrinology 2010; 151: 5617-5623). When female rats are fed a high fat diet, metabolism was also found to be altered in the next two generations, with only the females of the third generation showing this metabolic alteration, this latter phenotype being passed only paternally (Dunn and Bale, Endocrinology 2009; 150: 4999-5009; Dunn and Bale, Endocrinology 2011; 152: 2228-2236). If male rat parents are fed a low protein diet, then the offspring show metabolic alterations, such as lowered liver cholesterol (Carone et al., Cell 2010; 143: 1084-1096).

Human cohort studies also have proven to be the source of striking observations regarding apparent epigenetic effects on metabolism. For example, when mothers are exposed to famine during pregnancy, metabolism in male offspring is affected (Lumey et al., Am. J. Clin. Nutr. 2009; 89: 1737-1743). Second generation offspring also demonstrate alterations in metabolism, including a predisposition to suffer metabolic disease (Painter et al., Bjog. 2008; 115: 1243-1249). In another study, low food intake during adolescence correlated with an increase in survival of grandchildren (Pembrey et al., Eur. J. Hum. Genet. 2006; 14: 159-166).

Another example of intergenerational transmission of environmental information is the effect of stress experienced by parents, which appears to affect stress-related behaviors, and glucose metabolism, in offspring. For example, when parental male mice were exposed to maternal separation and unpredictable maternal stress (MSUS), depressive-like behaviors were observed in two subsequent generations (Franklin et al., Biol. Psychiatry 2010; 68: 408-415; see also Gapp, K et al., Nature Neuroscience 2014; 17(5): 667-669).

The mechanisms responsible for epigenetic inheritance patterns are just beginning to be understood. Mechanisms that have been implicated in these inheritance patterns thus far include histone modifications, DNA methylation, and non-coding RNAs, including RNA interference (RNAi) machinery, small interfering RNAs (siRNAs), Piwi-interacting RNAs (piRNAs) and microRNAs (miRNAs) (Lim and Brunet, Trends Genet. 2013 29(3):176-186). For example, there is evidence that paternal dietary conditions that affect offspring metabolism also affect the sperm small RNA payload (Sharma et al., Science 2016; 351(6271): 391-396). If purified sperm RNAs are injected into naive one-cell embryos, alterations in metabolism are observed in the resultant offspring (Grandjean et al., Sci Rep 2015; 5:18193; see also Chen, Q et al., Science 2016; 351: 397-400). Likewise, when total sperm RNA from traumatized males was injected into fertilized wild-type oocytes, the resultant offspring displayed metabolic changes (Gapp et al., Nature Neuroscience 2014; 17(5): 667-669). Finally, injecting nine sperm-specific miRNAs into zygotes that were identified in a paternal stress mouse model recapitulated the stress dysregulation phenotype in offspring (Rodgers et al., PNAS 2015; 112(44): 13699-13704).

There is a need in the art to efficiently modify sperm RNA payload to, for example, decrease the transmission of disease or disorders.

SUMMARY

In a first aspect, disclosed herein is a method of altering a population of sRNAs in a sperm of a subject, comprising contacting the sperm with an sRNA-containing vesicle isolated from an epididymosome to produce a sperm having an altered sRNA population. In embodiments, the sRNA is selected from the group consisting of a siRNA, a miRNA, a piRNA, a snoRNA, a srRNA, a U-RNA, and a tRNA fragment. In further embodiments, the tRNA fragment is selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment, the epididymosome is selected from the group consisting of caput epididymosome, corpus epididymosome, and cauda epididymosome.

In some embodiments, prior to contacting the sperm, the sperm is immature and altering an sRNA population increases sperm maturity. In other embodiments, prior to contacting the sperm, the sperm is defective and altering an sRNA population diminishes at least one defect. In such embodiments, the defective sperm can comprise a defect selected from the group consisting of a reduced level of sRNA, at least one aberrant sRNA, or absence of at least one sRNA that is present in healthy mature sperm. In an embodiment, the defective sperm comprises a defect in siRNA, miRNA, piRNA, snoRNA, srRNA, U-RNA, and tRNA fragment content. In further embodiments, the tRNA fragment content comprises a defect selected from the group consisting of tRNA-Gly-CCC fragment content, tRNA-Gly- TCC fragment content, tRNA-Gly-GCC fragment content, tRNA-Val-CAC fragment content, tRNA-Glu-CTC fragment content, tRNA-Lys-CTT fragment content, and tRNA-His-GTG fragment content. In other embodiments, the defective sperm comprises a decrease in at least one let-7 species of RNA when compared to a healthy sperm.

In certain embodiments, after altering the RNA content, the sperm is used to fertilize an oocyte.

In an embodiment, the subject is a mammal, such as a primate, such as a human.

In certain embodiments, the sperm that is altered is obtained from the subject's caput epididymis, corpus epididymis, cauda epididymis, vas deferens, testis, or ejaculate. In further embodiments, the sperm is obtained from the subject's caput epididymis, corpus epididymis, or cauda epididymis using microscopic or microsurgical epididymal sperm aspiration (MESA) or percutaneous epididymal sperm aspiration (PESA). In yet other further embodiments, the sperm is obtained from the subject's testis using a technique selected from the group consisting of needle aspiration (TESA), percutaneous or open surgical biopsy (TESE), multibiopsy TESE, microdissection TESE, site-directed TESE after fine needle aspiration mapping, and MicroTESE. Such techniques are routinely used in assisted reproduction.

In certain embodiments, the subject whose sperm is altered is experiencing a condition selected from the group consisting of a stress-related disease or disorder, a dietary restriction, and obesity. In an embodiment, the dietary restriction is protein deficiency. In another embodiment, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

In embodiments, the vesicle that is contacted to the sperm is heterologous to the subject. In other embodiments, the vesicle is autologous to the subject. In yet other embodiments, the vesicle comprises a heterologous RNA; the heterologous RNA can comprise a small RNA (sRNA). Such sRNA can be one selected from the group consisting of a siRNA, miRNA, a piRNA, a snoRNA, a srRNA, a U-RNA, and a tRNA fragment. In embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment where the sRNA is an miRNA, it can be selected from the group consisting of miR-10a/b, miR-141, miR-143, miR-148 and miR-200a. In other embodiments, the vesicle comprises autologous RNA. Such a vesicle can comprise sRNA that can be selected from the group consisting of a siRNA, miRNA, a piRNA, a snoRNA, a srRNA, a U-RNA, and a tRNA fragment. In the case where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment where the sRNA is an miRNA, it can be selected from the group consisting of miR-10a/b, miR-141, miR-143, miR-148 and miR-200a. In other embodiments, the vesicle comprises an artificial (synthetic) RNA. In such vesicles, the sRNA can be selected from the group consisting of a siRNA, miRNA, a piRNA, a snoRNA, a srRNA, a U-RNA, and a tRNA fragment. In the case where the sRNA is a tRNA fragment, then the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment where the sRNA is an miRNA, it can be selected from the group consisting of miR-10a/b, miR-141, miR-143, miR-148 and miR-200a. In other embodiments, the vesicle comprises a transgene.

In certain embodiments, the altered sperm fertilizes an oocyte in vitro. In other embodiments, the sperm is used in intracytoplasmic sperm injection (ICSI). These embodiments can further comprise implanting the fertilized oocyte to a second subject (e.g., a non-human subject) to produce a progeny.

In other embodiments, the altered sperm fertilizes an oocyte in vivo.

In embodiments, prior to contacting the sperm with a vesicle, the sperm are frozen.

In a second aspect, disclosed herein is a method of treating an epigenetically inheritable trait at risk of being transmitted to a progeny of a subject, comprising altering a population of sRNAs in a sperm from the subject by contacting the sperm with an sRNA-containing vesicle isolated from an epididymosome and fertilizing an oocyte with the sperm to produce the progeny. In embodiments, the sRNA is selected from the group consisting of a siRNA, a miRNA, a piRNA, a snoRNA, a srRNA, a U-RNA, and a tRNA fragment. In embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In embodiments where the sRNA is an miRNA, it can be selected from the group consisting of miR-10a/b, miR-141, miR-143, miR-148 and miR-200a. In other embodiments, the vesicle comprises a transgene.

In embodiments, the epididymosome is selected from the group consisting of caput epididymosome, corpus epididymosome, and cauda epididymosome.

In embodiments, the epigenetically inheritable trait is a disease or disorder that is a metabolic or stress-related disease or disorder. In some embodiments, the metabolic disease or disorder comprises a glucose or hepatic metabolic disease or disorder. In further embodiments, the hepatic metabolic disease or disorder comprises reduced sterol biosynthesis. In yet further embodiments, the reduced sterol biosynthesis comprises reduced cholesterol biosynthesis. In even further embodiments, hepatic Sqle gene expression is upregulated. In other embodiments, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

In embodiments, the progeny lacks symptoms of the epigenetically inheritable trait. In other embodiments, the progeny has ameliorated symptoms of the epigenetically inheritable trait.

In embodiments of this second aspect, the sperm comprises a defect selected from the group consisting of a reduced level of sRNA, at least one aberrant sRNA, or absence of at least one sRNA that is present in healthy mature sperm. In some embodiments, the sperm comprises a defect in siRNA, miRNA, piRNA, snoRNA, srRNA, U-RNA, and tRNA fragment content. In those embodiments wherein the defect is in tRNA content, the defect can be selected from the group consisting of tRNA-Gly-CCC fragment content, tRNA-Gly-TCC fragment content, tRNA-Gly-GCC fragment content, tRNA-Val-CAC fragment content, tRNA-Glu-CTC fragment content, tRNA-Lys-CTT fragment content, and tRNA-His-GTG fragment content. In other embodiments, prior to contacting the sperm, the sperm comprises a decrease in at least one let-7 species of RNA when compared to a healthy sperm.

In embodiments, the subject is a mammal, such as a primate, such as a human.

In embodiments, the sperm is obtained from the subject's caput epididymis, corpus epididymis, cauda epididymis, vas deferens, testis, or ejaculate. In such embodiments where the sperm obtained from the subject's caput epididymis, corpus epididymis, or cauda epididymis, microscopic or microsurgical epididymal sperm aspiration (MESA) or percutaneous epididymal sperm aspiration (PESA) is used. In other embodiments wherein the sperm is obtained from the subject's testis, a technique selected from the group consisting of needle aspiration (TESA), percutaneous or open surgical biopsy (TESE), multibiopsy TESE, microdissection TESE, site-directed TESE after fine needle aspiration mapping, and MicroTESE can be used. Such techniques are routinely used in assisted reproduction.

In embodiments of this second aspect, the subject is experiencing a condition selected from the group consisting of a stress-related disease or disorder, dietary restriction, and obesity. In further embodiments, the dietary restriction is protein deficiency. In other further embodiments, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

In some embodiments, the vesicle is heterologous to the subject. In other embodiments, the vesicle is autologous to the subject. In other embodiments, the vesicle comprises a heterologous RNA. In further embodiments, the heterologous RNA comprises a small RNA (sRNA). In such embodiments, the sRNA can be selected from the group consisting of a siRNA, miRNA, a piRNA, a snoRNA, a srRNA, a U-RNA, and a tRNA fragment. In embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises autologous RNA. In such vesicles, the sRNA can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises an artificial (synthetic) RNA. In such vesicles, the sRNA can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises a transgene.

In yet more embodiments of this second aspect, the sperm fertilizes an oocyte in vitro. In other embodiments, the sperm is used in intracytoplasmic sperm injection (ICSI).

Some embodiments comprise implanting the fertilized oocyte to a second subject to produce a progeny. In other embodiments, the sperm fertilizes an oocyte in vivo.

In embodiments, prior to contacting the sperm with an vesicle, the sperm are frozen.

In a third aspect, disclosed herein are pharmaceutical compositions comprising an vesicle comprising a small RNA molecule (sRNA). In embodiments, the sRNA is selected from the group consisting of a siRNA, a miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment.

In some embodiments, the pharmaceutical composition is a vaginal foam or gel.

In some embodiments, the vesicle is an exosome; in yet further embodiments, the exosome is an epididymosome. In further embodiments, the epididymosome is selected from the group consisting of caput epididymosome, corpus epididymosome, and cauda epididymosome. In other embodiments, the vesicle is a seminosome or a prostasome. In other embodiments, the vesicle is a microvesicle.

In embodiments of this third aspect, the vesicle comprises a heterologous RNA. In further embodiments, the heterologous RNA comprises a small RNA (sRNA). In yet further embodiments, the sRNA is selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises autologous RNA. In such embodiments, the vesicle comprises an sRNA that can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises an artificial (synthetic) RNA. In such embodiments, the vesicle comprises an sRNA that can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment, the vesicle comprises a transgene.

In certain embodiments of any of the aspects above in which the sRNA is an miRNA, it may be selected from the group consisting of miR-10a/b, miR-141, miR-143, miR-148 and miR-200a.

In a fourth aspect, disclosed herein is a method of altering the sRNA population in an oocyte, comprising altering a population of sRNA in a sperm by contacting a sperm with a vesicle isolated from an epididymosome (e.g., a caput epididymosome, a corpus epididymosome and/or a cauda epididymosome) to produce a sperm having an altered sRNA population, and fertilizing the oocyte with the sperm having an altered sRNA population. In certain embodiments, the sRNA is selected from the group consisting of a siRNA, a miRNA, a piRNA, a snoRNA, a srRNA, a U-RNA, and a tRNA fragment. In certain embodiments, the tRNA fragment is selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment.

In certain exemplary embodiments, the sperm comprises a defect selected from the group consisting of a reduced level of sRNA, at least one aberrant sRNA, or absence of at least one sRNA that is present in healthy mature sperm. In certain exemplary embodiments, the sperm comprises a defect in siRNA, miRNA, piRNA, snoRNA, srRNA, U-RNA, and tRNA fragment content.

In certain embodiments, the tRNA fragment content comprises a defect selected from the group consisting of tRNA-Gly-CCC fragment content, tRNA-Gly-TCC fragment content, tRNA-Gly-GCC fragment content, tRNA-Val-CAC fragment content, tRNA-Glu-CTC fragment content, tRNA-Lys-CTT fragment content, and tRNA-His-GTG fragment content. In certain embodiments, the miRNAs is selected from the group consisting of miR-10a/b, miR-141, miR-143, miR-148 and miR-200a. In certain embodiments, the vesicle comprises a synthetic RNA and/or a transgene.

In certain exemplary embodiments, the sperm fertilizes an oocyte in vitro or in vivo. In other embodiments, the sperm is used in intracytoplasmic sperm injection (ICSI). In certain embodiments, the method further includes the step of implanting the fertilized oocyte into a second, non-human subject to produce a progeny. In certain embodiments, the sperm are frozen prior to contacting the vesicle.

In a fifth aspect, disclosed herein is a method of altering a population of sRNAs in an isolated sperm, comprising contacting the isolated sperm with an sRNA-containing vesicle isolated from a caput epididymosome to produce a sperm having an altered sRNA population. In certain embodiments, the sperm having an altered sRNA population exhibits an increase in the levels of miRNAs and/or tRNA fragments compared to the levels of miRNAs and/or tRNA fragments in the isolated sperm prior to contacting the sRNA-containing vesicle. In other embodiments, a tRNA fragment is selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment and a tRNA-His-GTG fragment. In still other embodiments, a miRNA is selected from the group consisting of miR-10a/b, miR-141, miR-143, miR-148 and miR-200a.

In certain embodiments, the levels of tRNA fragments present are increased by at least about 5%, at least about 6%, at least about 7%, at least about 8%, at least about 9% or at least about 10% compared to levels of tRNA fragments in the isolated sperm prior to contacting with the sRNA-containing vesicle. In other embodiments, the levels of tRNA fragments present are increased by at least about two-fold compared to levels of tRNA fragments in the isolated sperm prior to contacting with the sRNA-containing vesicle.

In certain embodiments, the caput epididymosome is between about 100 nm and about 400 nm in diameter, between about 250 nm and about 350 nm in diameter, between about 120 nm and about 170 nm in diameter, or about 150 nm in diameter. In certain embodiments, the caput epididymosome is isolated from an epididymal sample and/or is isolated from the epididymal sample by ultracentrifugation.

In a fifth aspect, disclosed herein is a method of correcting a developmental defect in a zygote comprising microinjecting the zygote with a tRNA-Gly-GCC fragment to correct the developmental defect. In certain embodiments, the expression level of one or more genes associated with zygote development is altered. In other embodiments, the expression level of one or more genes associated with zygote development is downregulated.

BRIEF DESCRIPTION OF THE DRAWINGS

The foregoing and other features and advantages of the present invention will be more fully understood from the following detailed description of illustrative embodiments taken in conjunction with the accompanying drawings.

FIGS. 1A-1D shows the characterization of small RNAs in sperm. FIG. 1A shows small RNA sequencing data from mature cauda sperm samples. Sizes of deep sequencing reads are shown for the average of 12 small (<40 nt) cauda sperm RNA datasets. FIGS. 1B-1D show examples of abundant tRNA fragments (tRFs) in cauda sperm. tRNA fragments from the 5' end of tRNA-Gly-GCC (FIG. 1B), tRNA-Val-CAC (FIG. 1C), and tRNA-Glu-CTC (FIG. 1D) are shown schematically, with arrows indicating dominant 3' ends.

FIG. 2A shows a Northern blot analysis of total RNA isolated from testis, cauda epididymis, and caput epididymis, as indicated. FIG. 2B shows the quantitation of Northern blot data. Bars show levels of tRFs in testis, caput epididymis, and cauda epididymis, normalized to testis levels. Error bars show s.e.m. FIG. 2C shows pie charts showing the percentage of small RNAs mapping to the indicated features, for each tissue. rRNA-mapping reads are excluded.

FIG. 3A shows that sperm RNA payload diverges dramatically from the RNA population in testes. Small (<40 nt) RNA data from cauda sperm and from testes were normalized to parts per million (ppm) total reads (excluding rRNA-mapping reads), and data are shown for all RNAs present at greater than 5 ppm in the sperm or the testis averaged datasets. Scatterplot shows abundance of small RNAs in testis (x axis, log 10 scale) vs. sperm (y axis, log 10 scale), with RNAs mapping to tRNA genes, to microRNAs, to repeat elements/unique piRNAs, and to all other transcripts (fragments of mRNAs, snoRNAs, etc.) all indicated separately. FIG. 3B shows a schematic of murine epididymis. Sperm exiting the testis first enter the proximal (caput) epididymis, then proceed distally to the corpus and cauda epididymis, and exit via the vas deferens.

FIG. 5A shows that tRNA fragments that are more abundant in cauda, relative to caput, epididymis are also gained in cauda sperm. The scatterplot shows the relative changes between caput and cauda epididymis (x axis—positive values show cauda-enriched RNAs) compared to relative changes between caput and cauda sperm (y axis). Note that given the normalization to total small RNA abundance, a "loss" of a given tRF present in caput sperm could result from degradation of this tRF, or from constant abundance of this tRF in the face of overall tRF gain. FIG. 5B shows proximal-distal biases for tRFs in the epididymis and in sperm samples, averaged for each anticodon. Only tRFs with an average abundance of >100 ppm small RNAs are shown, and tRFs are ordered by cauda/caput ratio for epididymis samples.

FIG. 6A show a transmission electron micrograph of purified cauda epididymosomes, showing abundant vesicles of about 120-150 nm. FIG. 6B shows epididymosome size distribution. Nanosight sizing data for two independent cauda epididymosome preps. Data for 0-200 nm are shown in main panel, while inset shows 0-500 nm zoom-in. FIG. 6C shows that epididymosomal preparations are not contaminated with free RNA, or with fragments of sperm. tRNA fragments are protected from RNaseA treatment, indicating their presence in vesicles. In addition, epididymosomes purified from tdrd1−/− mice, which lack mature sperm, carry high levels of tRNA fragments, indicating that our epididymosome preparations are not simply fragments generated from maturing sperm such as the residual body.

FIG. 8A shows a schematic of murine epididymis. Circles represent epididymosomes. FIG. 8B shows a transmission electron micrograph of purified cauda epididymosomes (top panel), showing abundant vesicles of approximately 120-150 nm. Lower panel shows vesicle size distributions for epididymosomes isolated from cauda or from caput epididymis, obtained using nanosight sizing. A subtle increase in approximately 250-300 nm vesicles is apparent in cauda samples. FIG. 8C shows distributions for epididymosomal small (<40 nt) RNA-Seq libraries, showing highly abundant 28-32 nt (approximately 87% of reads) 5' tRNA fragments for cauda epididymosomes. In contrast, caput epididymosomes primarily carry microRNAs, with approximately 28% of reads mapping to 5' tRFs. FIG. 8D shows that small RNA populations in epididymosomes are highly correlated with those in mature sperm. The scatterplot shows abundance of various classes of small RNAs for sperm (x axis, log scale) and epididymosomes (y axis, log scale). FIG. 8E shows the consistent proximal-distal biases for specific RNAs in epididymis and epididymosome samples. For all RNAs with a maximum abundance of greater than 10 ppm in either caput or cauda samples, the log 2(cauda/caput) ratio is plotted for epididymis (x axis) vs. epididymosomes (y axis).

FIG. 9A shows Taqman analysis of the indicated tRFs in purified caput sperm and in "reconstituted" caput sperm which have been incubated with cauda epididymosomes, showing gain of tRFs relative to normalization control let-7. FIG. 9B shows the results of deep sequencing of sperm reconstitutions. In each case, tRFs are aggregated by codon, and data are normalized to levels of tRF-Glu-CTC. For bull, data shown mean and s.e.m. for four replicate reconstitutions experiments. For mouse, deep sequencing libraries were under sequenced approximately 100-200 thousand reads), and only two replicates were sequenced, but the same trends seen between natural caput and cauda sperm were recapitulated, with cauda-enriched tRFs such as tRF-Val-CAC being delivered to caput sperm via fusion with cauda epididymosomes.

FIG. 10A shows Affymetrix microarray data for mRNA abundance in embryonic stem cells transfected with an LNA antisense oligo targeting tRF-Gly-GCC. The X axis shows abundance of mRNAs in anti-GFP knockdown cells, and the y axis shows mRNA abundance for cells transfected with an LNA antisense targeting the 5' end of tRF-Gly-GCC. Data represent average of seven replicates. FIG. 10B shows the effect of tRF-Gly-GCC knockdown on MERVL is isoacceptor-specific. Affymetrix data for knockdown studies with the indicated LNA antisense oligos. All comparisons are to GFP siRNA transfections done in the same batch. Identical results are obtained when comparing to mock-transfected ES cells. All genes showing abundance changes of 2-fold or greater in 2 or more samples are shown. FIG. 10C shows RNA-Seq data for four pooled replicate samples of ES cells transfected with shRNA against GFP, or with the anti-tRF-Gly-GCC LNA oligo, as indicated. FIG. 10D shows a schematic showing genomic context for four tRF-Gly-GCC target genes, showing MERVL LTRs associated with all target genes. Some additional target genes, such as the Tdpoz cluster, are not as closely associated with MERVL LTRs, but instead are located in large MERVL-rich genomic clusters, and have also been shown to be part of the MERVL-regulated gene expression program (Macfarlan, T S, et al. 2012. Nature 487: 57-63). FIG. 10E shows that inhibition of tRF-Gly-GCC affects MERVL target expression in 4-cell embryos. Control zygotes were generated via IVF, and then either mock-injected or injected with an antisense oligonucleotide targeting tRF-Gly-GCC. Embryos were then allowed to develop to the 4-cell stage, and subject to single-embryo RNA-Seq. Averaged single embryo RNA-Seq data for control (n=28) or tRF-inhibited (n=27) embryos. Among genes upregulated at least 2-fold on average, those previously described as MERVL targets are indicated separately. FIG. 10F shows examples of single embryo data for two MERVL targets. Here, each bar represents mRNA abundance from a single embryo, with embryos ordered from highest to lowest expression for each condition.

FIG. 11A shows embryos generated by IVF that were cultured for varying times, then subject to single embryo RNA-Seq. FIG. 11B shows single-embryo data for preimplantation embryos represented via PCA: first two principal components explain 74% of dataset variance. FIG. 11C shows mRNA abundance in 2-cell embryos generated via IVF using Control vs. Low Protein sperm (n=41 C and 39 LP). Cumulative distribution plots for tRF-Gly-GCC targets (p=4.5×10-7, KS test), other MERVL targets (17) (p=2.5×10-13), and all remaining genes, showing percentage of genes with the average Log 2(LP/C) indicated on the x axis. Low Protein embryos exhibit a significant shift to lower expression of MERVL targets. Bottom panels show individual embryo data for two targets. FIG. 11D shows small RNAs isolated from Control or Low Protein cauda sperm were microinjected into control zygotes. RNA-Seq (n=42 C and 46 LP embryos) reveals downregulation of tRF-Gly-GCC targets (p=4.8×10-14) driven by Low Protein RNA. FIG. 11E shows the effects of synthetic tRF-Gly-GCC on 2-cell gene regulation, showing significant (p=0.0001) downregulation of target genes in embryos injected with tRF-Gly-GCC (n=26) vs. GFP controls (n=11). Inset shows effects of tRF-Glu-CTC (n=6). FIG. 11F shows effects of epididymal passage on embryonic gene regulation. Intact sperm isolated from rete testis (n=12), or cauda epididymis (n=9), were injected into control oocytes, and mRNA abundance was analyzed as above.

FIG. 12A shows subjected cumulative distribution plot for all genes encoding ribosomal protein genes during the indicated stages. X axis shows the relative expression of these genes in Low Protein IVF embryos, compared to Control. Grey line shows distribution of dietary effects on all non-RPG genes, for all four stages. Left shift at the 2-cell stage shows downregulation of RPGs in Low Protein 2-cell embryos. FIGS. 12B-E show GSEA plots for various sets of genes involved in ribosome biogenesis at the indicated developmental stages.

FIG. 12F shows an example image of a blastocyst stained with DAPI and anti-Cdx2 to image total cell number and trophectoderm cells. FIG. 12G shows that Low Protein diet reproducibly alters developmental tempo. FIG. 12H shows aggregated data for three replicate experiments, showing the number of blastocysts with the indicated number of cells, for embryos generated via IVF using Control or Low Protein sperm, as indicated.

FIG. 13A shows a schematic illustrating assay for tRNA charging analysis. FIG. 13B shows validation of tRNA charging protocol. Changes in tRNA abundance for charged and uncharged tRNAs are shown on the y axis, sorted by the change in charged tRNA abundance. FIG. 13C shows testicular tRNA abundance correlation with codon bias in the mouse. The X axis shows intact tRNA abundance in testis in log scale, and the y axis shows the corresponding codon abundance (in codon frequency/1000) in all murine mRNAs, or in the 47 most-highly expressed mRNAs in testis. FIG. 13D shows validation of tRNA charging analysis. Scatterplot shows abundance of approximately 60-80 nt RNAs in the total RNA protocol (x axis, log scale) compared to abundance of RNAs in the charged tRNA protocol (y axis, log scale). FIGS. 13E-13G show Low Protein vs. Control effects on tRNA levels for total (FIG. 13E), uncharged (FIG. 13F), and charged (FIG. 13G) tRNA levels in testis. FIG. 13H shows that dietary effects on sperm tRFs are not explained by effects on intact tRNA abundance in testes.

FIG. 14A shows the dietary effects on small RNA abundance in testes and caput and cauda epididymis samples. Each heatmap shows log 2 of Low Protein/Control RNA abundance for a pair of samples, showing RNAs (rows) that exhibit consistent dietary effects across >75% of samples. FIG. 14B shows the coherent dietary effects on tRF-Gly and let-7 family members throughout the male reproductive tract. For each RNA, bars show average and standard error of the mean for Low Protein effects on the abundance of the RNA species in the indicated tissue. Changes with a nominal p value of <0.05 (paired t test, not corrected for multiple testing) are indicated with asterisks.

FIG. 15A shows that unwashed caput sperm are contaminated with RNAs abundant in caput epididymosomes. FIG. 15B shows a comparison of small RNA payloads of cauda vs. caput sperm for all RNA species with an abundance of at least 1 ppm in both sperm populations. FIG. 15C shows the proximal-distal biases observed for epididymis (x axis) are recapitulated in cauda vs. caput sperm samples (y axis). FIG. 15D shows that there is a gain in all four tRFs from caput to cauda. Data from FIG. 15D are shown with tRF-Val-CAC normalized to tRF-Glu-CTC rather than to microRNAs. FIG. 15E shows that tRF-Val-CAC is strongly cauda-enriched in all three preparations—epididymal epithelium, epididymosomes, and sperm—examined. FIG. 15F depicts Northern blots showing that caput sperm carry intact tRNAs FIG. 16A shows the sperm from males consuming Control or Low Protein diet which were used to fertilize oocytes gathered from Control females. Sqle levels (normalized to Actb) are shown for all offspring as individual points, with horizontal lines showing mean expression. FIG. 16B shows the cumulative distribution of Sqle expression for all offspring generated using Control or Low Protein sperm, as indicated. FIG. 16C shows consistent litter effects. Sqle levels were averaged for all offspring of a given litter.

FIG. 17A shows RNA-Seq and ribosome footprinting data for Sp110. FIG. 17B shows that RNA abundance and ribosome footprinting data are highly correlated, indicating that tRF-Gly-GCC does not affect MERVL elements as a secondary effect of its effects on protein translation.

FIG. 18A depicts an experimental schematic showing purified testicular sperm, which carry extremely low levels of tRFs, were incubated with caput epididymosomes for 2 hours, and then extensively washed with detergent. Small RNAs were purified from either mock-treated testicular sperm, or reconstituted sperm, and deep sequenced. Pie charts show average levels of various small RNA classes, revealing increased levels of microRNAs and tRFs delivered to testicular sperm by epididymosomes. FIG. 18B shows the delivery of two prominent tRFs to testicular sperm. Taqman q-RT-PCR for the indicated tRFs, with individual replicates plotted (on aa log 2 y axis) relative to the average level present in Mock-treated testicular sperm. FIG. 18C shows the distribution of small RNA changes upon reconstitution. The X axis shows the log 2-fold difference between reconstituted and mock-treated sperm; positive values indicate delivery by epididymosomes. The peak for piRNAs is approximately −0.6, reflecting the assumption in genome-wide normalization of equal numbers of molecules in both samples. Under conditions of RNA delivery, pre-existing RNAs (shown), the piRNAs that predominate in testicular sperm will appear to "decrease" in abundance due to normalization. As such, all values over −0.6 indicate gain of RNA during the fusion protocol. FIG. 18D shows a scatterplot of small RNA abundances from deep sequencing data. The strong diagonal for piRNAs indicates RNAs present in testicular sperm that are not affected by the delivery process. Essentially all RNAs shown either lie along this diagonal, indicating that they are either absent or present in low abundance in caput epididymosomes, or above the diagonal, indicating widespread delivery of many RNA species to testicular sperm during reconstitution.

DETAILED DESCRIPTION

Figure 1A:
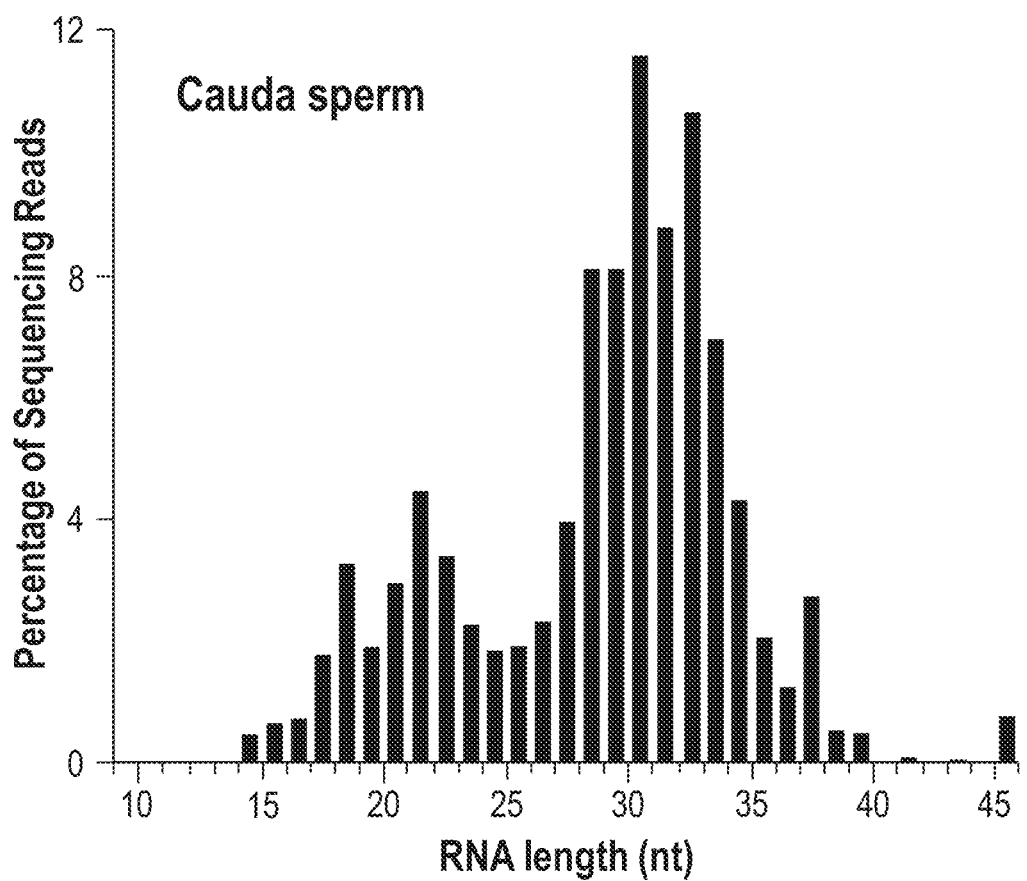

The present disclosure is directed to methods and compositions that can alter sperm molecular content, such that a disease, disorder, or condition that would otherwise be inherited by offspring, are not, or such disease, disorder, or condition severity is reduced.

The inventors discovered that as sperm mature in the male reproductive tract, their molecular cargo changes. Specifically, as sperm move through the epididymis, the small RNA molecule (sRNA) content changes dramatically. The sperm sRNA content mirrors that found in vesicles found in the different regions of the epididymis ("epididymosomes"). For example, a sperm located in the cauda epididymis has a similar sRNA content as a caudal epididymosome.

The inventors have discovered methods of altering the RNA content of sperm, such as to increase the maturity of immature sperm, to "rescue" defective mature sperm that have at least one sRNA defect (e.g., a reduction or absence of at least one sRNA, or at least one aberrant sRNA), and to decrease transmission of epigenetically-transmitted diseases or disorders to progeny. These methods involve contacting the target sperm with vesicles, such as epididymosomes, to alter the sperm RNA content. Such treated sperm can then be used to fertilize oocytes in vitro or in vivo.

I. Definitions

As used in the specification and in the claims, the term "comprising" may include the embodiments "consisting of" and "consisting essentially of" The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 600 to about 2000" also discloses the range "from 600 to 2000." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

As used herein, "treatment" or "treating," is defined as the application or administration of a therapeutic agent to a subject, or application or administration of a therapeutic agent to an isolated tissue, cell line, or cell from a subject. "Therapeutic agents" include vesicles, including epididymosomes.

As used herein, "patient," "individual" or "subject" refers to a human or a non-human mammal. Non-human mammals include, for example, livestock and pets, such as ovine, bovine, porcine, canine, feline and murine mammals. Non-human mammals also include primates. Preferably, the patient, subject, or individual is human.

As used herein, "untreated sperm" means sperm that have not been subjected to the application or administration of a therapeutic agent as described in the disclosed methods. "Treated sperm" means sperm that have been subjected to the application or administration of a therapeutic agent as described in the disclosed methods. In embodiments, an untreated sperm may have been exposed to vesicles in the male reproductive tract, but become treated sperm when exposed to vesicles that are autologous or heterologous in vitro. In some embodiments, the untreated sperm are treated in vivo when exposed to autologous or heterologous vesicles, which can be comprised in a composition, such as a pharmaceutical composition.

As used herein, "vesicle" means extracellular vesicles (EVs) that cells shed from their plasma membrane, or from multivesicular bodies. These vesicles are generally referred to as microvesicles, ectosomes, shedding vesicles, or microparticles, as well as exosome vesicles (or exosomes). Exosomes are extracellular vesicles that originate from multivesicular endosomes (MVEs) that fuse with the plasma membrane. However, circulating extracellular vesicles such as epididymosomes also include microvesicles (MVs). Thus, unless otherwise noted, the term "vesicles" includes MVs and exosomes. A vesicle comprises at least one RNA molecule, such as a small RNA (sRNA). Vesicles that originate from specific tissues or cells can be designated by specific terms, such as epididymosomes, which originate from the epididymis; seminosomes which originate from seminal fluid, and prostasomes, which originate from the prostate. The ExoCarta database (found on the world-wide web at exocarta.org) contains the proteins, lipids, and RNA that have been found in EVs from various sources.

As used herein, "altering the RNA content" means, such as when applied to cells, such as sperm, to add or remove an RNA molecule by treating the cells or sperm. For example, vesicles can be used to deliver RNA cargo to sperm, thus altering the RNA content of the sperm.

As used herein, "increasing sperm maturity" means that after a treatment, the sperm takes on or improves in at least one characteristic that indicates that the sperm has further matured. An increase in sperm maturity is reflective of a healthy sperm that has progressed to the same location or further in the male reproductive tract relative to the untreated sperm.

As used herein, "a defective sperm" means a sperm that lacks at least one characteristic in relation to its maturity by virtue of its location in the male reproductive tract or ejaculate when compared to a healthy ejaculated sperm. The altered characteristic can be a difference in at least one molecule, such as an RNA molecule or a polypeptide. The difference can be the absence of a molecule, the presence of a molecule that is usually absent in healthy sperm, or a changed molecule, such as a mutated or mis-processed molecule. In some embodiments, the at least one molecule is a sRNA. "Rescuing a defective sperm" means to add or subtract the molecule that is different than healthy sperm, or supplying a wild-type molecule of a changed molecule, to the sperm by treating the sperm, so that the sperm resemble healthy sperm in relation to its source of isolation from the male reproductive tract or ejaculate. "Defective mature sperm" means a sperm that appears to have matured by virtue of it completing its journey through the male reproductive tract, but lacks at least one characteristic of mature healthy sperm. A defective mature sperm is not necessarily incapable of fertilizing an oocyte, but may instead transmit a trait, condition, disease, or disorder to a resulting progeny.

As used herein, "epigenetically-transmitted" means a trait, condition, disease, or disorder transmitted by a parent to offspring wherein the acquired trait, condition, disease, or disorder is not the result of a mutation in DNA; that is, the trait is transmitted in violation of Mendelian genetics. In such intergenerational epigenetic inheritance, epigenetic phenotypes are transmitted to at least one generation and may be gender-specific.

As used herein, "healthy sperm" means a sperm that has the characteristics of sperm found in healthy, fertile subjects in relation to its maturity by virtue of its location in the male reproductive tract or ejaculate.

As used herein, "sRNA" means "small RNA" and includes all classes of small RNAs, including: small interfering RNAs (siRNAs), Piwi-interacting RNAs (piRNAs), microRNAs (miRNAs), tRNA fragments (tRF), small nucleolar RNA (snoRNA), small rDNA-derived RNA (srRNA), and small nuclear RNA (U-RNA). Generally, sRNAs are about 200 nucleotides or less in length, such as 40 nucleotides in length, or less. siRNAs are generally double-stranded pairs of RNAs about 20-25 base pairs long, and can participate in the RNA interference (RNAi) pathway (Hannon, G J and J J Rossi. 2004. Nature, 431:371-378). piRNAs are non-coding RNA molecules of about 26-31 nucleotides long and form RNA-polypeptide complexes with piwi proteins. These RNA molecules have been linked to epigenetic gene silencing of "molecular parasites," such as transposons found in germ line cells (Czech, B and G J Hannon. 2016. Trends Biochem Sci, 41: 324-337; Siomi M C, et al. 2011. Nat Rev Mol Cell Biol, 12:246-258). miRNAs are about 19-24 nucleotide long, non-coding RNA molecules. They regulate protein-coding gene expression translationally and post-transcriptionally (Virant-Klun, I., et al. 2016. Stem Cells Int. 2016:3984937). tRFs are fragments of tRNA molecules that are about 28 to 34 nucleotides long, have a wide variety of molecular effects on cells and are found enriched in, for example, sperm (Peng, H., et al. 2012. Cell Res, 22: 1609-1612). snoRNA guide chemical modifications of other RNAs, such as rRNAs, tRNAs, and snRNAs; these small non-coding RNAs fall into two classes, one of about 60-90 nucleotides long ("box C/D"), and another of about 120-140 nucleotides long ("box H/ACA") (Dupuis-Sandoval, F, et al. 2015. Wiley Interdiscip Rev RNA, 6: 381-397). srRNAs map by sequence to rRNA coding regions in the sense direction; coimmunoprecipitate with Argonaute proteins, and are involved in various signaling pathways, and are thought to be about 18-30 nucleotides long (Wei, H, et al. 2013. PLoS One, 8: e56842). U-RNA molecules are about 150 nucleotides long and function to process pre-mRNA in the nucleus (Zhang, L, et al. 2013. Protein Sci, 22: 677-692).

An "aberrant" sRNA is an sRNA molecule that differs from a wild-type sRNA. For example, the sRNA has a changed sequence, such as one or more point mutations, deletions, insertions, translocations; or is chemically modified, etc.

An "artificial RNA" or "synthetic RNA" is an RNA molecule that is synthesized in vitro by any art-accepted method.

As used herein, "stress" means a state of physical, mental or emotional strain or tension in an organism, such as a subject, that results from adverse or demanding circumstances and causes physiological alterations in the organism. The stress is often applied repeatedly or continually. In some embodiments, the stress may last for a period of time. In some cases, the physiological alterations are present after the stress has been applied.

As used herein, "dietary restriction" means a diet that is deficient in one or more components of a healthy diet, such as a vitamin, a nutrient, a micronutrient, a fat, a simple carbohydrate, a complex carbohydrate, and protein, or a calorie deficit (that is, insufficient calories to support the health of an organism) such that the physiology of an organism is altered. In some embodiments, the restriction is repetitive or continual. In some embodiments, the restriction may last for a period of time. In some cases, the physiological change persists after the dietary restriction stops.

As used herein, "overeating" means the condition of an organism consuming more calories than is necessary to maintain the normal health of the organism.

As used herein, "stress-related disease or disorder" means a disease or disorder which symptoms in an organism can be triggered or amplified by the application of stress to an organism. In some embodiments, a stress-related disease or disorder is related to mental health. In some embodiments, the mental health disease or disorder is a form of depression, such as major depressive disorder (also known as major depression or clinical depression), dysthymia, and bipolar disorder (having a depressive phase). Other examples of mental health disease or disorders include those that are anxiety-based conditions, including generalized anxiety disorder, a specific phobia, social anxiety disorder, separation anxiety disorder, agoraphobia, and panic disorder.

As used herein, "metabolic disorder" means a disorder wherein a component of metabolism is absent, up-regulated, or down-regulated when compared to the metabolism of a healthy organism, such as a subject. A metabolic disorder can manifest in many forms. For example, the metabolic disorder can be a hepatic metabolic disorder, which originates in the liver, or affects the expression of a marker of liver-based metabolism, such as Sqle gene expression. A manifestation of a hepatic metabolic disorder includes a reduction in sterol biosynthesis, such as reduced cholesterol biosynthesis. Pancreatic metabolic disorders include type II diabetes.

As used herein, "reduced" means that the substance or activity being measured is present in a lesser amount and/or lesser activity than when compared to that of a healthy organism.

"Healthy" means that the organism, tissue, or cell has the composition and activity of an organism, tissue or cell that falls within the boundaries of wild-type expression, indicative of a non-disease state.

II. Methods

In an aspect, disclosed herein is a method of altering the RNA content of a sperm of a subject, comprising contacting the sperm with a vesicle comprising a sRNA to produce a sperm having an altered RNA content.

In a second aspect, disclosed herein is a method of treating an epigenetically inheritable trait at risk of being transmitted to a progeny of a subject, comprising altering the RNA content of a sperm from the subject by contacting the sperm with a vesicle comprising a sRNA and fertilizing an oocyte with the sperm to produce the progeny.

In embodiments, the sRNA is selected from the group consisting of a siRNA, a miRNA, a piRNA, a snoRNA, a srRNA, a U-RNA, and a tRNA fragment. In further embodiments, the tRNA fragment is selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment, the vesicle is an exosome; in yet further embodiments, the exosome is an epididymosome; the epididymosome can be selected from the group consisting of caput epididymosome, corpus epididymosome, and cauda epididymosome. In other embodiments, the vesicle is a seminosome or a prostasome. In other embodiments, the vesicle is a microvesicle.

In some embodiments, prior to contacting the sperm, the sperm is immature and altering the RNA content increases sperm maturity. In other embodiments, prior to contacting the sperm, the sperm is defective and altering the RNA content diminishes at least one defect. In such embodiments, the defective sperm can comprise a defect selected from the group consisting of a reduced level of sRNA, at least one aberrant sRNA, or absence of at least one sRNA that is present in healthy mature sperm. In an embodiment, the defective sperm comprises a defect in siRNA, miRNA, piRNA, snoRNA, srRNA, U-RNA, and tRNA fragment content. In further embodiments, the tRNA fragment content comprises a defect selected from the group consisting of tRNA-Gly-CCC fragment content, tRNA-Gly-TCC fragment content, tRNA-Gly-GCC fragment content, tRNA-Val-CAC fragment content, tRNA-Glu-CTC fragment content, tRNA-Lys-CTT fragment content, and tRNA-His-GTG fragment content. In other embodiments, the defective sperm comprises a decrease in at least one let-7 species of RNA when compared to a healthy sperm.

In embodiments, after altering the RNA content, the sperm fertilizes an oocyte.

In an embodiment, the subject is a mammal, such as a primate, such as a human.

In embodiments, the sperm that is altered is obtained from the subject's caput epididymis, corpus epididymis, cauda epididymis, vas deferens, testis, or ejaculate. In further embodiments, the sperm is obtained from the subject's caput epididymis, corpus epididymis, or cauda epididymis using microscopic or microsurgical epididymal sperm aspiration (MESA) or percutaneous epididymal sperm aspiration (PESA). In yet other further embodiments, the sperm is obtained from the subject's testis using a technique selected from the group consisting of needle aspiration (TESA), percutaneous or open surgical biopsy (TESE), multibiopsy TESE, microdissection TESE, site-directed TESE after fine needle aspiration mapping, and MicroTESE. Such techniques are routinely used in assisted reproduction.

In embodiments, the subject which sperm is altered is experiencing a condition selected from the group consisting of a stress-related disease or disorder, dietary restriction, and obesity. In an embodiment, the dietary restriction is protein deficiency. In another embodiment, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

In embodiments, the vesicle that is contacted to the sperm is heterologous to the subject. In other embodiments, the vesicle is autologous to the subject. In yet other embodiments, the vesicle comprises a heterologous RNA; the heterologous RNA can comprise a small RNA (sRNA). Such sRNA can be one selected from the group consisting of a siRNA, miRNA, a piRNA, a snoRNA, a srRNA, a U-RNA, and a tRNA fragment. In embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises autologous RNA. Such an vesicle can comprise sRNA that can be selected from the group consisting of a siRNA, miRNA, a piRNA, a snoRNA, a srRNA, a U-RNA, and a tRNA fragment. In the case where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises an artificial (synthetic) RNA. In such vesicles, the sRNA can be selected from the group consisting of a siRNA, miRNA, a piRNA, a snoRNA, a srRNA, a U-RNA, and a tRNA fragment. In the case where the sRNA is a tRNA fragment, then the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises a transgene.

In embodiments, the altered sperm fertilizes an oocyte in vitro. In other embodiments, the sperm is used in intracytoplasmic sperm injection (ICSI). These embodiments can further comprise implanting the fertilized oocyte to a second subject to produce a progeny.

In other embodiments, the altered sperm fertilizes an oocyte in vivo.

In embodiments, prior to contacting the sperm with a vesicle, the sperm are frozen.

Specifically in the second aspect, the epigenetically inheritable trait is a disease or disorder that is a metabolic or stress-related disease or disorder. In some embodiments, the metabolic disease or disorder comprises a glucose or hepatic metabolic disease or disorder. In further embodiments, the hepatic metabolic disease or disorder comprises reduced sterol biosynthesis. In yet further embodiments, the reduced sterol biosynthesis comprises reduced cholesterol biosynthesis. In even further embodiments, hepatic Sqle gene expression is upregulated. In other embodiments, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

In embodiments of this second aspect, the progeny lacks symptoms of the epigenetically inheritable trait. In other embodiments, the progeny has ameliorated symptoms of the epigenetically inheritable trait.

In yet other embodiments of this second aspect, the subject is experiencing a condition selected from the group consisting of a stress-related disease or disorder, dietary restriction, and obesity. In further embodiments, the dietary restriction is protein deficiency. In other further embodiments, the stress-related disease or disorder is selected from the group consisting of major depressive disorder, dysthymia, bipolar disorder, generalized anxiety disorder, a phobia, social anxiety disorder, separation anxiety disorder, agoraphobia, and panic disorder.

Vesicles

Vesicles can be used to treat a subject, organ, tissue, or cell (such as sperm). Vesicles can be used as found in their normal milieu, such as a tissue fluid. In the case of epididymosomes, fluid found in the epididymis contains vesicles and can be directly applied to the target subject, organ, tissue, or cell (such as sperm).

However, in preferable embodiments, vesicles are used at least partially purified. "Purified" means to be substantially free from other components normally associated with the purification target in a native environment. Vesicle purification can be accomplished by many procedures. For example, in the case of cultured cells, differential ultracentrifugation can be used (Raposo, G and W Stoorvogel. 2013. J Cell Biol., 200: 373-383). If cultured cells are used as a source of vesicles, media components, such as serum (e.g., fetal bovine serum), are depleted of EVs before applying to the cells so as to not contaminate the cell vesicle preparation with vesicles of other origins. To separate vesicles from non-membranous particles (such as protein aggregates), the relatively low buoyant density and differences in floatation velocity can be used (Raposo, G, et al. 1996. J Exp Med., 183: 1161-1172; Escola, J M, et al. 1998. J Biol Chem, 273: 20121-20127; Van Niel, G, et al. 2003. Gut, 52:1690-1697; Wubbolts, R, et al. 2003. J Biol Chem, 278: 10963-10972; Aalberts, M, et al. 2012. Biol Reprod, 86:82. In some embodiments, vesicles can be further purified through immunopurification by using a protein of interest found on the surface of the target vesicle. A method of purifying vesicles is also set out in the Examples.

Vesicles can also be isolated using a number of commercially available kits, such as Total Exosome Isolation (Invitrogen (ThermoFisher Scientific); Waltham, Mass.), Exo-Quick-TC™ (System Biosciences; Palo Alto, Calif.), ME™ (New England Peptide; Gardner, Mass.), miRCURY™ (Exiqon; Woburn, Mass.); and Exo-spin™ (Cell Guidance Systems; St. Louis, Mo.), In some embodiments, physical methods can be used to produce nanovesicles that have some of the features of vesicles (Gyorgy, B. et al. 2015.Annu Rev Pharmacol Toxicol. 55: 439-464). For example, cells comprising the target molecules to be transferred to the target subject, organ, tissue, or cell can be extruded through filters, which fragment the cells and generate vesicles (Jang, S C, et al. 2013. ACS Nano, 7: 7698-7710). Alternatively, such cells can be extruded through a microfluidic chamber (Jo, W, et al. 2014. Lab Chip, 14: 1261-1269). Such formed vesicles are similar to endogenous EVs in size, shape, and composition and can deliver RNA molecules (Gyorgy, B. et al. 2015. Annu Rev Pharmacol Toxicol. 55: 439-464). In principle, vesicles can also be formed by sonicating, lysing, electroporating and freeze-thawing cells (Gyorgy, B. et al. 2015. Annu Rev Pharmacol Toxicol. 55: 439-464).

In certain embodiments, vesicles (e.g., epididymosomes) of the invention are between about 50 nm and about 400 nm in diameter, between about 60 nm and about 350 nm in diameter, between about 70 nm and about 300 nm in diameter, between about 80 nm and about 250 nm in diameter, between about 90 nm and about 150 nm in diameter, between about 110 nm and about 180 nm in diameter, between about 240 nm and 360 nm in diameter, or any ranges of diameters or individual diameters between these ranges. In exemplary embodiments, vesicles (e.g., epididymosomes) of the invention are approximately 150 nm in diameter.

In embodiments, vesicles can be loaded with molecular cargo (such as a sRNA), such as by using electroporation or co-incubation (Alverez-Erviti, L, et al. 2011. Nat. Biotechnol. 29: 341-345; El-Andaloussi, S, et al. 2012. Nat Protoc, 7: 2112-2126; Sun, D, et al. 2010. Mol. Ther. 18:1606-1614; Tian, Y H, et al. 2014. Biomaterials, 35:2383-2390). In some embodiments, the molecular cargo includes a transgene. In other embodiments, the molecular cargo includes an artificial (synthetic RNA). In some embodiments, the molecular cargo includes an autologous molecule, such as an RNA molecule (such as a sRNA); in other embodiments, the molecular cargo includes a heterologous molecule.

In some embodiments, vesicles can be modified to incorporate a molecule that targets a tissue or cell-specific molecule; e.g., a molecule that binds to a sperm-specific membrane molecule, such as a protein or a lipid.

In some embodiments, further characterization of the vesicles may be desired to ensure that the targeted vesicles have indeed been purified. Methods such as sizing (although both "true" vesicles as well as MVs can be isolated in a single preparation; size does not necessarily distinguish true vesicles from MVs), immunoblotting, mass spectrometry, and imaging techniques can be used to further characterize isolated vesicles (Raposo, G and W Stoorvogel. 2013. J Cell Biol., 200: 373-383). Imaging techniques include conventional transmission electron microscopy, whole mount transmission electron microscopy, and cryo-electron transmission electron microscopy. In addition, nanoparticle tracing analysis to determine size distribution of the isolated vesicles can be accomplished based on the Brownian motion of vesicles in suspension (Soo, C Y, et al. 2012. Immunology, 136: 192-197). Furthermore, individual vesicles can be analyzed using high resolution flow cytometry methods when the vesicles are immunolabeled (Nolte-'t Hoen, E N. 2012. Nanomedicine, 8:712-720; van der Vlist, E J, et al. 2012. Nat Protoc, 7: 1311-1126).

Sperm Acquisition

In embodiments, untreated sperm, or untreated immature sperm, or untreated defective mature sperm ("sperm") are obtained from a subject, such as from a mammal, such as a primate or human. A mammalian sperm, which may also be referred to as a "spermatid," "spermatozoon" or "spermatozoan," are produced through spermatogenesis inside the testicle through meiotic division. Sperm formed in the testis then enter the caput epididymis, progress through the corpus epididymis region, and finally enter the cauda epididymis. After exiting the testis, sperm mature by structurally and functionally reorganizing the sperm membrane, which maturation results in the acquisition of motility and fertilization capabilities. However, sperm also lose their ability to synthesize proteins (Barkalina, N, et al. 2015. Human Reprod Update, 21(5): 627-639). Epididymosomes fuse with sperm to deliver proteins, including P34H (necessary for fertilization), ADAM-7 (a disintegrin and metalloproteinase), glioma pathogenesis-related I-like protein; epididymal sperm binding protein I (ELSPBPI), and plasma membrane $Ca^{2+}$-ATPase (Barkalina, N, et al. 2015. Human Reprod Update, 21(5): 627-639). Fusion not only changes the protein composition of the sperm, but also its lipid composition (Barkalina, N, et al. 2015. Human Reprod Update, 21(5): 627-639).

During ejaculation, sperm flow from the cauda epididymis through the vas deferens prior to entering the ejaculatory duct. The sperm then pass through the prostate gland, enter the urethra, and exit the body through the urethral opening in the seminal fluid (also referred to as the ejaculate). Sperm for use in the disclosed methods can be retrieved from any point along the reproductive tract from the testis to the ejaculate, including the subject's testis, epididymis (including the caput, corpus, or cauda epididymis), vas deferens, or ejaculate. In the case of in vivo fertilization, the sperm remain in the ejaculate for fertilization of the oocyte.

In one embodiment, sperm can be obtained from a subject's epididymis (including from the caput, corpus, and cauda epididymis) using microscopic or microsurgical epididymal sperm aspiration (MESA) or percutaneous epididymal sperm aspiration (PESA). In another embodiment, sperm can be obtained from a subject's testis using a technique selected from the group consisting of needle aspiration (TESA), percutaneous or open surgical biopsy (TESE), multibiopsy TESE, microdissection TESE, site-directed TESE after fine needle aspiration mapping, and MicroTESE. Such techniques are routinely used in assisted reproduction.

In one embodiment, sperm can be from the same subject or a different subject than the source of vesicles for use in the disclosed methods. In another embodiment, the sperm can be a donor sperm, such as those available from a sperm bank.

The isolated, untreated sperm may comprise a condition such as reduced levels of sRNA, at least one aberrant sRNA, or the absence of at least one sRNA that is present in healthy sperm. In other embodiments, there may be increased levels of an sRNA compared to healthy sperm, or the presence of sRNAs that are not usually present in healthy sperm. For example, untreated sperm can have an absence or decrease in at least one sRNA selected from the group consisting of tRNA-Gly-CCC fragments, tRNA-Gly-TCC fragments, tRNA-Gly-GCC fragments, tRNA-Lys-CTT fragments, and tRNA-His-GTG fragments; or aberrant forms of these molecules. A decrease in a sRNA is one wherein such a decrease has an effect on an offspring, such as in the case of an epigenetically transmitted condition. In some embodiments, the sRNA that is absent, decreased, or is aberrant is a let-7 species of miRNA.

In some embodiments, the sperm that is obtained is from a subject that has experienced some form of stress, including mental stress, dietary restriction, or overeating. For example, the subject may suffer from a protein deficiency. In other embodiments, the subject has a disease or disorder that is a metabolic or stress-related disease or disorder. Such diseases and disorders can be a hepatic metabolic disease or disorder, which can include reduced sterol biosynthesis (such as reduced cholesterol synthesis), or an upregulation or downregulation in hepatic Sqle gene expression. In other embodiments, the stress-related disease or disorder is a mental health disease or disorder, such as depression.

In some embodiments, the sperm is frozen using well-established techniques, such as those used by sperm banks, for later use in the disclosed methods.

Oocyte Fertilization

A mammalian "oocyte," which may also be referred to as an "ovocyte," "immature ovum" or "egg cell" for use in the disclosed methods is produced through oogenesis by meiotic division.

An oocyte for use in in vitro fertilization can be retrieved from a subject by any known method, including aspiration directly from the ovarian follicles. An oocyte for use in in vivo fertilization is not retrieved, but fuses with the sperm within the subject prior to implantation in the uterus.

An oocyte may be fertilized by any known method, including in vivo methods and in vitro methods. In certain embodiments, the method of oocyte fertilization may be in vitro fertilization (IVF). In one embodiment, the oocyte may be fertilized through intracytoplasmic sperm injection (ICSI).

Vesicle Application

For in vitro application, partially or fully purified vesicles can be resuspended in a buffered solution, such as phosphate-buffered saline (PBS) or cell culture media (and if serum is present, it is EV-depleted). Alternatively, the vesicles can be formulated into a pharmaceutical composition comprising, for example, a pharmaceutical excipient or carrier. To contact the target tissue or cells, for example, the vesicles are applied to the tissue or cells, and the components incubated for a sufficient time to permit vesicle fusion and cargo delivery. For example, solutions comprising vesicles can be incubated with the target tissue or cells for minutes to hours to days, such as, in minutes, 1, 2, 3, 4, 5, 6, 7, 8, 9, 10, 15, 20, 25, 30, 35, 40, 45, 50, 55, 60, 120, 180, and 240; such as in hours, 5, 6, 7, 8, 9, 10, 11, 12, 13, 14, 15, 16, 17, 18, 19, 20, 21, 22, 23, 24, 30, 36, 42, and 48; such as in days, 3 and 4. One of skill in the art can ascertain the time to incubate an vesicle-containing composition with the target tissue or cells, adjusting variables of not only time, but also variables concerning the applied concentration of vesicles (often determined by quantifying total protein), temperature (typically physiological temperatures, but above about 4° C.), volume, components of buffered solution used for resuspension, and number of target cells. Vesicles can be applied to the target tissue or cells multiple times.

Alternatively, vesicles can be injected into a subject in a pharmaceutical composition, such as glucose (e.g., 5% glucose) (Cooper, J M, et al. 2014. Mov Disord., 29(12): 1476-1485).

Pharmaceutical compositions comprising vesicles, dosage forms, and dosing, are described in more detail below.

As defined above, vesicles comprise at least one RNA molecule. Such RNA molecule can be a sRNA, such as siRNA, miRNA, piRNA, snoRNA, srRNA, U-RNA, or tRNA fragment (tRF). Such RNA can be heterologous or autologous. For example, in some embodiments, the sperm to be treated are immature, whether by virtue of a biological cause or isolation location, but the vesicles are derived from cauda epididymis of the same subject (e.g., wherein the RNA are therefore autologous in the case of isolating immature sperm based on location), or derived from the cauda epididymis of another subject (thus comprising heterologous RNA), which may be desirable to treat immature sperm from healthy subjects as well as for treating immature sperm from subjects having a biological cause that results in immature sperm. In other embodiments, heterologous RNA is introduced into vesicles isolated from the same subject as the sperm donor. For example, such RNA can be one that is derived from the epididymis, such as the cauda epididymis.

Pharmaceutical Compositions

Pharmaceutical compositions comprising vesicles are expounded on in part, for example, in US 20160060652.

Pharmaceutical compositions that contain vesicles useful in the disclosed methods can comprise a liquid medium. Examples of liquid media include water, physiologically acceptable buffer solutions (phosphate-buffered saline, etc.) and biocompatible aqueous mediums such as propylene glycol and polyoxyethylene sorbitan fatty acid ester. The media is desirably sterile and adjusted to be isotonic to blood or other tissue fluid (e.g., epididymal) if necessary.

Pharmaceutical compositions can comprise a pharmaceutically acceptable carrier. Examples of pharmaceutically acceptable carriers include suspending agents, tonicity agents, buffers and preservatives. Carriers can be used to facilitate formulation and maintaining the dosage form and drug effects.

For example, glyceryl monostearate, aluminum monostearate, methylcellulose, carboxymethylcellulose, hydroxymethylcellulose and sodium lauryl sulfate can be used as suspending agents. Examples of tonicity agents include sodium chloride, glycerin and D-mannitol. Examples of buffers include phosphate, acetate, carbonate and citrate. Examples of preservatives include benzalkonium chloride, parahydroxybenzoic acid and chlorobutanol.

If necessary or desired, pharmaceutical compositions can also comprise a corrigent, a thickener, a solubilizing agent, a pH adjuster, a diluent, a surfactant, an expander, a stabilizer, an absorption promoter, a wetting agent, a humectant, an adsorbent, a coating agent, a colorant, an antioxidant, a flavoring agent, a sweetener, an excipient, a binder, a disintegrant, a disintegration inhibitor, a filler, an emulsifier, a flow control additive, or a lubricant.

Pharmaceutical compositions useful in the disclosed methods can also contain an additional drug without losing pharmacological effects possessed by the vesicles. For example, the pharmaceutical composition may contain an antibiotic.

Information directed to suitable formulations and additional carriers can be found in, for example, Remington "The Science and Practice of Pharmacy" (20th Ed., Lippincott Williams & Wilkins, Baltimore Md.), which is incorporated by reference in its entirety herein.

In some embodiments, a dosage form may be desired. A dosage form of the pharmaceutical composition is not limited and can be any form that does not inactivate the vesicle or its contents. The dosage form of pharmaceutical compositions can be, for example, a liquid, solid or semisolid form. Specific examples of dosage form include parenteral dosage forms such as injections, suspensions, emulsions, creams, ointments, gels and foams. In some embodiments, the dosage form is a vaginal gel or foam.

A "pharmaceutically effective amount" refers to a dose required for the vesicles contained in pharmaceutical compositions to prevent, diminish, or treat the target disease or condition, or alleviate symptoms, in a subject and/or in the subject's offspring (or in some cases, the offspring's offspring). A specific dose differs depending on the disease to be prevented, diminished, and/or treated; the mechanism of action underlying the occurrence of the disease, the dosage form used, information about a subject and an administration route, etc. The range of the pharmaceutically effective amount and a preferred administration route of the pharmaceutical composition that is administered to a human subject are generally set on the basis of data obtained from cell culture assay and animal experiments. The final dose can be determined and adjusted by the judgment of, for example, a physician. Information about the subject to be taken into consideration can include the degree of progression or severity of the disease, general health conditions, age, body weight, sex, diet, drug sensitivity and resistance to treatment, etc.

The pharmaceutical compositions can be administered twice or more at predetermined intervals of time, for example, every hour, 3 hours, 6 hours or 12 hours; every day, every 2 days, 3 days or 7 days; or every month, 2 months, 3 months, 6 months or 12 months.

The administration of the pharmaceutical composition can be systemic administration or local administration, and can be appropriately selected according to the target organ, tissue, or cell location. Local administration is preferred for in vivo treatments because the vesicles can be administered in a sufficient amount to the site (organ, tissue, or cells) to be effective in treatment, but have no influence on other tissues. However, if the vesicles are targeted to a specific organ, tissue, or cell-type (e.g., by virtue of incorporating in the vesicle a protein or lipid that binds a specific molecule on the target organ, tissue, or cell), then systemic administration through, for example, intravenous injection or the like can be used. Blood flow will systemically transport the vesicles, which will then contact the target organ, tissue, or cells.

In the case of administration by injection, the injection site may be a site where the vesicle can exert its functions and attain the purpose of the pharmaceutical composition. Examples of injection sites include intravenous, intraarterial, intrahepatic, intramuscular, intraarticular, intramedullary, intraspinal, intraventricular, percutaneous, subcutaneous, intracutaneous, intraperitoneal, intranasal, intestinal and sublingual sites. In one embodiment, direct administration to the epididymis is preferred.

III. Compositions and Kits

In yet another aspect, disclosed herein are pharmaceutical compositions comprising an vesicle comprising a small RNA molecule (sRNA). In embodiments, the sRNA is selected from the group consisting of a siRNA, a miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment.

In some embodiments, the pharmaceutical composition is a vaginal foam or gel.

In some embodiments, the vesicle is an exosome; in yet other embodiments, the exosome is an epididymosome. In further embodiments, the epididymosome is selected from the group consisting of caput epididymosome, corpus epididymosome, and cauda epididymosome. In other embodiments, the vesicle is a seminosome or a prostasome. In other embodiments, the vesicle is a microvesicle.

In embodiments of this third aspect, the vesicle comprises a heterologous RNA. In further embodiments, the heterologous RNA comprises a small RNA (sRNA). In yet further embodiments, the sRNA is selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises autologous RNA. In such embodiments, the vesicle comprises an sRNA that can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In other embodiments, the vesicle comprises an artificial (synthetic) RNA. In such embodiments, the vesicle comprises an sRNA that can be selected from the group consisting of a siRNA, miRNA, a piRNA, a snoRNA, a srRNA, a U-RNA, and a tRNA fragment. In those embodiments where the sRNA is a tRNA fragment, the tRNA fragment can be selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment. In an embodiment, the vesicle comprises a transgene.

Kits

In some embodiments, components necessary to perform the methods disclosed herein are included in kits. For example, vesicles can be formulated into pharmaceutical compositions and supplied in a vessel for use as a vaginal foam or gel for in vivo use. In other embodiments, vesicles can be supplied in a vessel suspended in a buffer or media for in vitro or in vivo use, such as would be suitable for contacting isolated sperm with the vesicles. In some embodiments, the vesicles incorporate heterologous molecular cargo. In some embodiments, this molecular cargo is an RNA molecule (such as a sRNA) or a transgene.

Reagents included in kits can be supplied in containers of any sort such that the life of the different components are preserved and are not adsorbed or altered by the materials of the container. For example, sealed glass ampules may contain lyophilized components (such as vesicles), or buffers that have been packaged under a neutral, non-reacting gas, such as nitrogen. Suitable buffers include those that maintain the integrity of the vesicles over time. Ampules may consist of any suitable material, such as glass, organic polymers (i.e., polycarbonate, polystyrene, etc.), ceramic, metal or any other material typically employed to hold reagents. Other examples of suitable containers include simple bottles that may be fabricated from similar substances as ampules, and envelopes that may have foil-lined interiors, such as aluminum or alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits can also be supplied with instructional materials. Instructions may be printed on paper or other substrate and/or may be supplied as an electronic-readable medium, such as a floppy disc, CD-ROM, DVD-ROM, DVD, SD card, videotape, audio tape, etc. Detailed instructions may not be physically associated with the kit; instead, a user may be directed to an internet web site specified by the manufacturer or distributor of the kit, or supplied as electronic mail.

EXAMPLES

Example 1—Mouse Husbandry

Mice used in this study were primarily FVB/NJ strains, obtained from Jackson Laboratories (Bar Harbor, Me.). All animal care and use procedures were in accordance with guidelines of the Institutional Animal Care and Use Committee (University of Massachusetts). Animals were raised on one of two diets—defined control diet (AIN-93G; Bio-serv; Flemington, N.J.) or a Low Protein diet based on AIN-93g (10% of protein rather than 19%, remaining mass made up with sucrose)—as previously described (Carone, B R, et al. 2010. Cell 143: 1084-1096). Because it has been observed that in natural matings that paternal dietary effects are substantially less penetrant when using females from our long term mouse colony, the experiments described herein have been restricted to the use of female mice whose parents or grandparents had been obtained from the animal vendor.

Example 2—Epididymosome Isolation

An adult male mouse (8-12 weeks old) was sacrificed using double kill method (Isofluorane treatment followed by spinal dislocation). Next, cauda epididymis was dissected out and placed in a dish containing 1 ml Whitten's media (100 mM NaCl, 4.7 mM KCl, 1.2 mM $KH_2PO_4$, 1.2 mM $MgSO_4$, 5.5 mM Glucose, 1 mM Pyruvic acid, 4.8 mM Lactic acid (hemicalcium), and HEPES 20 mM) pre-warmed at 37° C. The epididymides were then gently squeezed using forceps to isolate the epididymal luminal content. The dish was then placed in an incubator set at 37° C. with 5% $CO_2$ for 15 minutes to allow any remaining epididymal content to release from the tissue. Next, the media containing epididymal luminal content was transferred to a 1.5 ml tube and allowed to incubate for an additional 15 minutes. At the end of the 15 minutes, any tissue pieces or non-motile sperm settled down at the bottom of the tube and all the contents of the tube except for the bottom approximately 50 µl were transferred to a fresh tube. Next, the tube was spun in a tabletop centrifuge at 2000×g for 5 minutes to pellet down sperm. The supernatant, which contained epididymosomes, was then transferred to a fresh tube and centrifuged at 10000×g for 30 minutes at 4° C. to get rid of any non-sperm cells and cellular debris. Supernatant from this spin was then transferred to a polycarbonate thick wall tube (13×56 mm, Beckman Coulter (Brea, Calif.), Catalog number 362305) and centrifuged at 120000×g for 2 hours at 4° C. in a table top ultracentrifuge (Beckman Optima TL) using a TLA100.4 rotor. The pellet from this spin was then washed with 500 µl 1×PBS and centrifuged for another 2 hours at 120000×g at 4° C. Finally, the pellet containing epididymosomes was resuspended in 50 µl ice-cold 1×PBS, transferred to a 1.5 ml tube, and flash frozen in liquid nitrogen.

Example 3—Small RNA Cloning

Total RNA was combined with an equal volume of Gel Loading Buffer II (Ambion; ThermoFisher Scientific; Carlsbad, Calif.), loaded onto a 15% Polyacrylamide with 7M Urea and 1×TBE gel, and run at 15 W in 1×TBE until the dye front was at the very bottom of the gel (approximately 25 minutes for Criterion™ minigels (Bio-Rad; Hercules, Calif.)). After staining with SYBR Gold (Life Technologies; Carlsbad, Calif.) for 7 minutes, and destaining in 1×TBE for 7 minutes, gel slices corresponding to 18-40 nucleotides were then cut from the gel. Gel slices were then ground using a pipette tip or plastic pestle and mixed with 750 µl of 0.3 M NaCl-TE, pH 7.5 prior to incubation with shaking on a thermomixer overnight at room temperature. The samples were then filtered using a 0.4 µm cellulose acetate filter (Costar®; Corning; Corning, N.Y.) to remove gel debris. The eluate was transferred to a new low binding microcentrifuge tube and 20 µg of glycoblue and 1 volume of isopropanol (approximately 700 µl) were added. Samples were precipitated for 30 or more minutes at −20° C.

Size selection of the small RNAs was then followed by the ligation of a 3' adaptor and then a barcoded 5' adaptor as described by Gu et al (2009, Mol. Cell 36: 231-244). The libraries were then converted to DNA using SuperScript III® reverse transcriptase (Invitrogen; ThermoFisher Scientific) and amplified by sequential rounds of PCR, to first add short primer tails and then longer primer tails, providing the products with the correct adaptor sequences for deep sequencing. Libraries were then sequenced by Illumina HiSeq 2000 (Illumina; San Diego; CA) at the University of Massachusetts Deep Sequencing Core (Worcester, Mass.).

Example 4—Normalization and Data Analysis

For each small RNA library, rRNA-mapping reads (which were highly abundant in testis and epididymis samples, but rare in epididymosome and sperm samples) were removed. Remaining reads were mapped to murine tRNAs, to the unique sequences present in the 467 defined pachytene piRNA clusters (Li, X Z, et al. 2013. Mol. Cell 50:67-81), to Repeatmasker (Institute for Systems Biology; Seattle, Wash.) (tRNA entries from Repeatmasker were deleted to avoid duplicating tRNA-mapping reads), to miRbase (Kozomara, A and S Griffiths-Jones, 2011. NAR 39 (Database Issue): D152-D157) and to Refseq (Pruitt, K C D et al., 2014. NAR 42(1): D756-D763) (using RSEM (web link: deweylab.github.io/RSEM/) to separate distinct mRNA isoforms). Non rRNA-mapping reads were normalized to parts per million mapped reads.

Example 5—ES Cell Culture and Transfection

E14 Embryonic Stem Cell (ESC) lines were grown in DMEM (Gibco™; ThermoFisher Scientific), and transfections were carried out in in Opti-MEM™ (Gibco™; ThermoFisher Scientific) in 6 well plates (Fazzio, T G, et al. 2008. Cell 134: 162-174), with 9.5 $cm^2$ wells of ES cells seeded at a density of $2.3 \times 10^5$ cells/mL. One ng of antisense LNA containing oligonucleotides (synthesized by Exiqon; Woburn, Mass.) were transfected using Lipofectamine™ 2000 (Invitrogen, ThermoFisher Scientific) for 16 hours, then ESCs were allowed to recover for 32 hours. Controls included Lipofectamine™ (Fisher Scientific) only (Mock) and anti-GFP shRNA transfections. RNA extraction was performed at the end of 48 hours using the standard TRIzol® (Ambion, Life Technologies; Carlsbad, Calif.) protocol. RNA extracted from mouse ES cells was prepared for hybridization on Mouse GeneChip® 2.0 ST arrays (Affymetrix; Santa Clara, Calif.) using the GeneChip® WT PLUS kit from Affymetrix.

Example 6—In Vitro Fertilization, Embryo Culture, RNA Microinjection, and Single Embryo RNA-Seq In vitro fertilization (IVF) was performed according to Nagy (*Manipulating the Mouse Embryo: A Laboratory Manual* (Cold Spring Harbor Laboratory Press, Cold Spring Harbor, N.Y., ed. 3, 2003)). FVB/NJ mice were used as egg donors and sperm was isolated from males fed dietary regimes as previously described. Fertilization took place in 250 µl of HTF media covered in mineral oil, pre-gassed in 5% $CO_2$ at 37° C.

IVF-derived control zygotes were placed in KSOM medium in 5% $CO_2$ 5% $O_2$ incubator for 2 hours after IVF. Embryos were then washed twice in FHM medium containing 0.1% PVA, and subject to micromanipulation. Embryos were microinjected with either H3.3-GFP mRNA (control group) or H3.3-GFP mRNA+tRF-Gly-GCC antisense RNA (experimental group). RNA concentrations used for microinjections were: 100 ng/µl for H3.3-GFP and 200 ng/µl for tRF-Gly-GCC antisense RNA. The sequence of the tRF-Gly-GCC antisense RNA is 5'GCG AGA AUU CUA CCA CUG AAC CAC CAA UGC 3' (SEQ ID NO:1). After the microinjections, embryos were placed back into culture, and GFP fluorescence was verified at the 2-cell stage. GFP-positive injected embryos were cultured until the 4-cell stage, when they were collected and processed for single-embryo RNA sequencing.

Single embryo RNA-Seq was carried out using the SMART-Seq protocol (Ramskold, S, et al. 2012. Nat. Biotechnol. 30: 777-782; Shalek, A K, et al. 2013. Nature 498: 236-240).

Example 7—Epididymal Delivery of Small RNAs to Immature Sperm

To interrogate the molecular mechanisms underlying transmission of paternal dietary information to offspring, the small (<40 nt) RNA repertoire of mouse sperm were characterized. Sperm were isolated from the cauda epididymis and subjected to several wash steps including a detergent wash with epithelial lysis buffer, yielding preparations that were routinely >99.5% pure as assessed by microscopy. Sperm RNA was isolated, subjected to size selection (<40 nt), and small RNAs were characterized by cloning (with or without "healing" of 3' ends by PNK treatment) and deep sequencing as previously described (Gu, W. et al. 2013. Cell, 151: 1488-1500). The resulting sequencing libraries show a remarkable abundance of approximately 28-32 nt tRNA fragments (tRFs) in mature sperm (approximately 80% of all small RNAs with cloneable 3' ends), as well as less abundant peaks of 19 nt and 22 nt RNAs (FIG. 1A). The tRFs in the dataset were derived from the 5' ends of tRNAs (no evidence was found for persistence of 3' fragments in mature sperm), and untreated RNAs typically exhibit 2-4 predominant 3' ends with a series of lower-abundance products potentially deriving from degradation or alternative cleavage/processing sites (FIGS. 1B-1D). As previously reported (Peng, H et al. 2012. Cell Res. 22:1609-1612), 5' fragments of tRNA-Glu-CTC and tRNA-Gly-GCC were particularly abundant, although the presently described dataset demonstrated that levels of 5' tRFs derived from other tRNA-glycine isoacceptors and from tRNA-valine isoacceptors were comparable to those of tRF-Gly-GCC. 5' tRFs were also highly abundant in cauda sperm obtained from *B. taurus*, revealing that extensive tRNA cleavage in gametes is conserved among mammals.

Example 8—tRNA Fragments are Abundant in the Epididymis

Figure 2A:
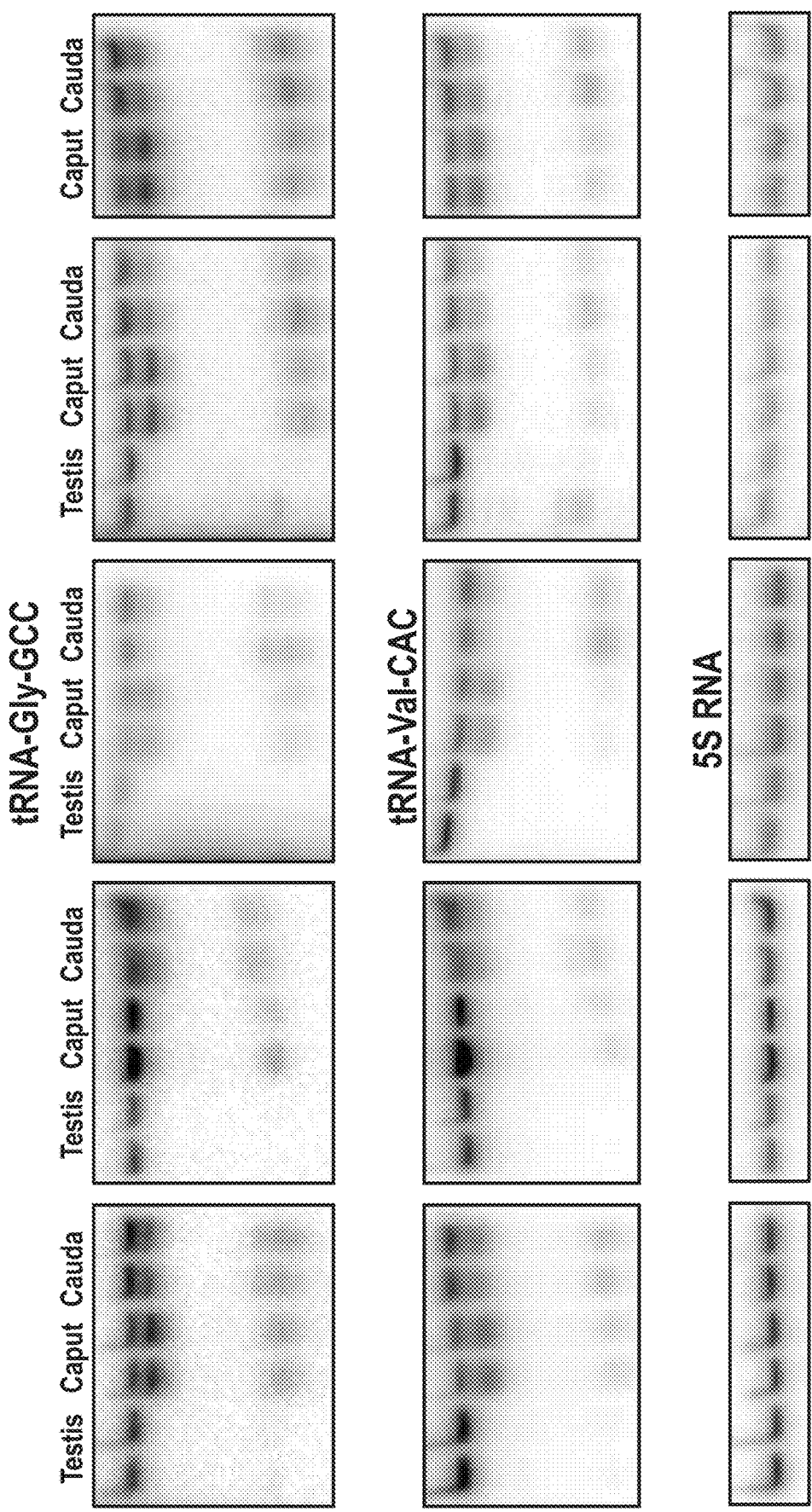
FIGS. 2A-2C show that tRNA fragments are abundant in the epididymis.
Figure 2B:
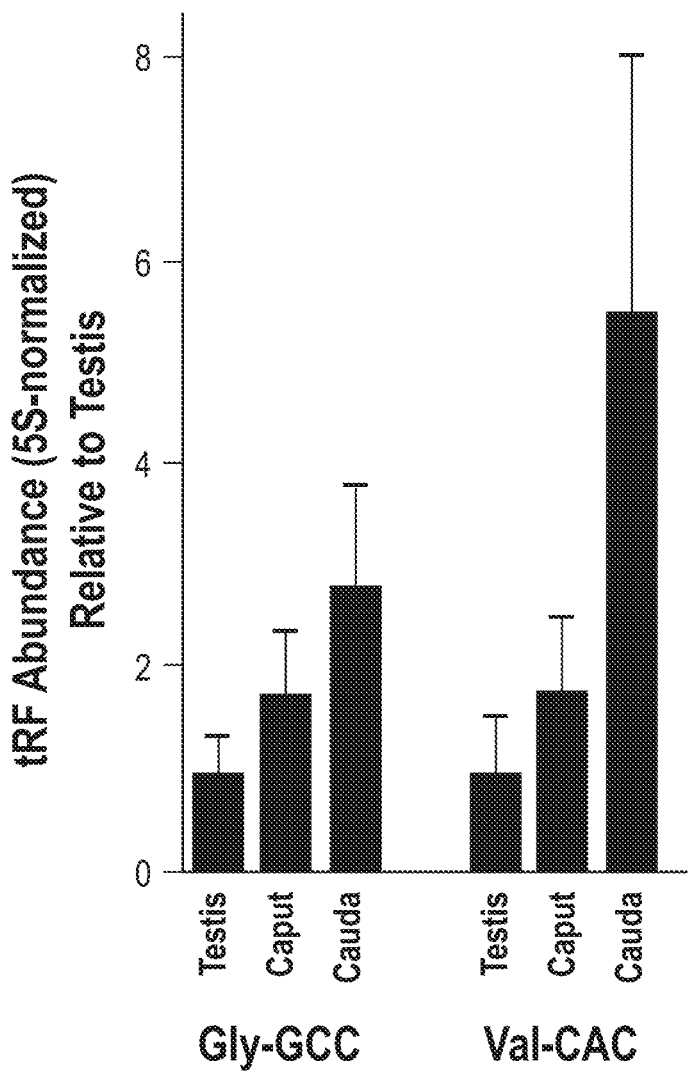
Figure 2C:
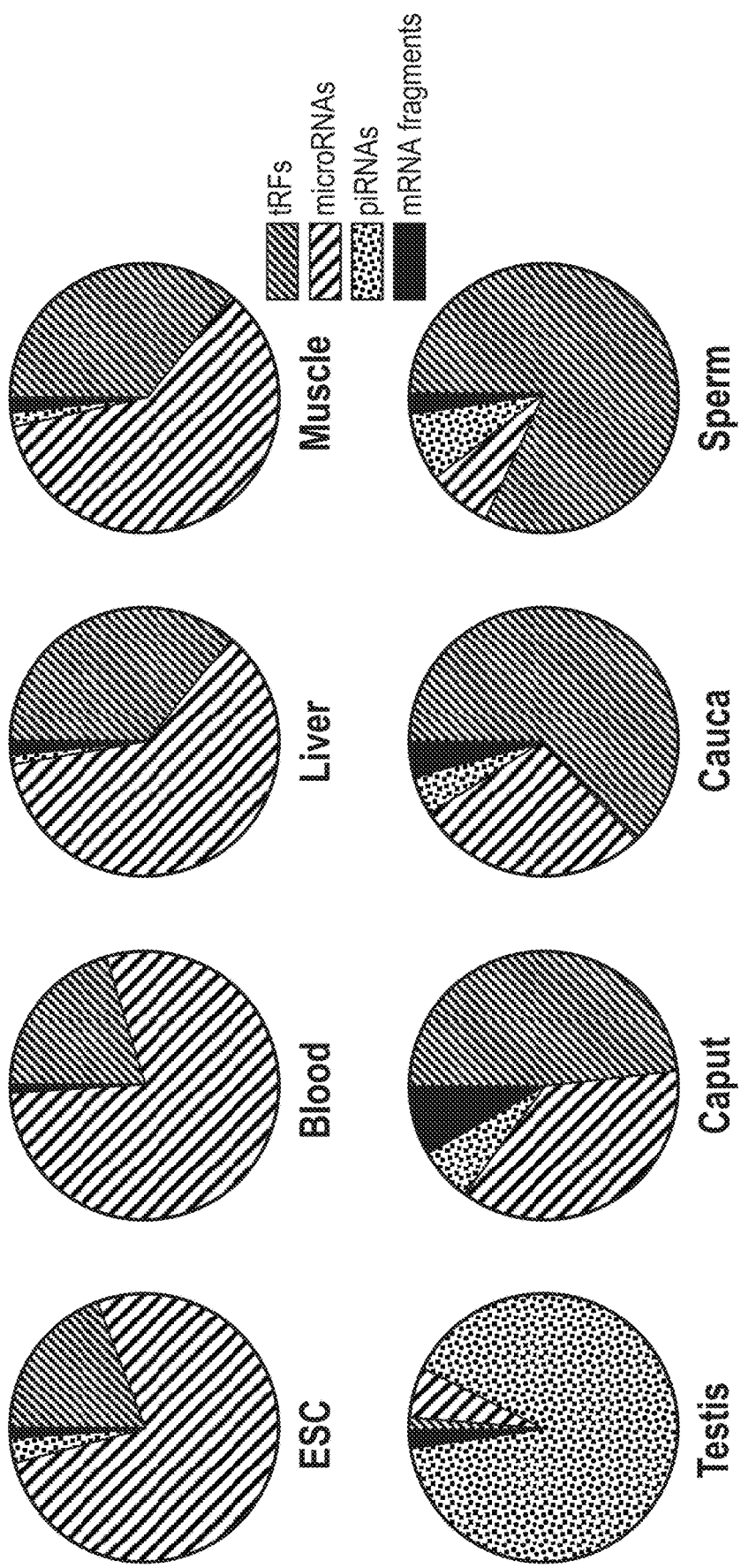

This example shows that tRNA fragments are abundant in the epididymis; the data are presented in FIG. 2. FIG. 2A shows a Northern blot analysis of total RNA isolated from testis, cauda epididymis, and caput epididymis, as indicated. Each panel (except the right-most panel, missing testis samples) shows paired samples in which each of the three tissues was obtained from the same animal. For each pair of samples, the left sample was isolated from a Control animal and right sample was isolated from a littermate consuming a Low Protein diet. The approximately 55-60 nt band observed in epididymis samples for tRNA-Gly-GCC and tRNA-Val-CAC varied somewhat in abundance between samples. This band almost certainly represents a T loop tRNA cleavage product rather than an intact tRNA differing in size from the approximately 75 nt tRNA by virtue of amino acid charging, as (1) it migrates at approximately 55-60 nt, which is too short to be an intact tRNA, (2) this band was observed both when using RNAs isolated under acidic conditions and using RNAs isolated under more basic deacylating conditions (not shown), and (3) it is absent in testis samples. FIG. 2B shows the quantitation of Northern blot data. For the indicated tRNAs, levels of the approximately 30 nt tRNA fragment were quantitated and normalized to 5S RNA abundance. Bars show levels of tRFs in testis, caput epididymis, and cauda epididymis, normalized to testis levels. Error bars show s.e.m. FIG. 2C shows pie charts showing the percentage of small RNAs mapping to the indicated features, for each tissue. rRNA-mapping reads are excluded. Here, piRNAs refer to all small RNAs mapping either to Repeatmasker or to unique piRNA clusters (Li, X Z et al. 2013. Molecular Cell, 50: 67-81).

Example 9—tRNA Processing in the Epididymis

Figure 3A:
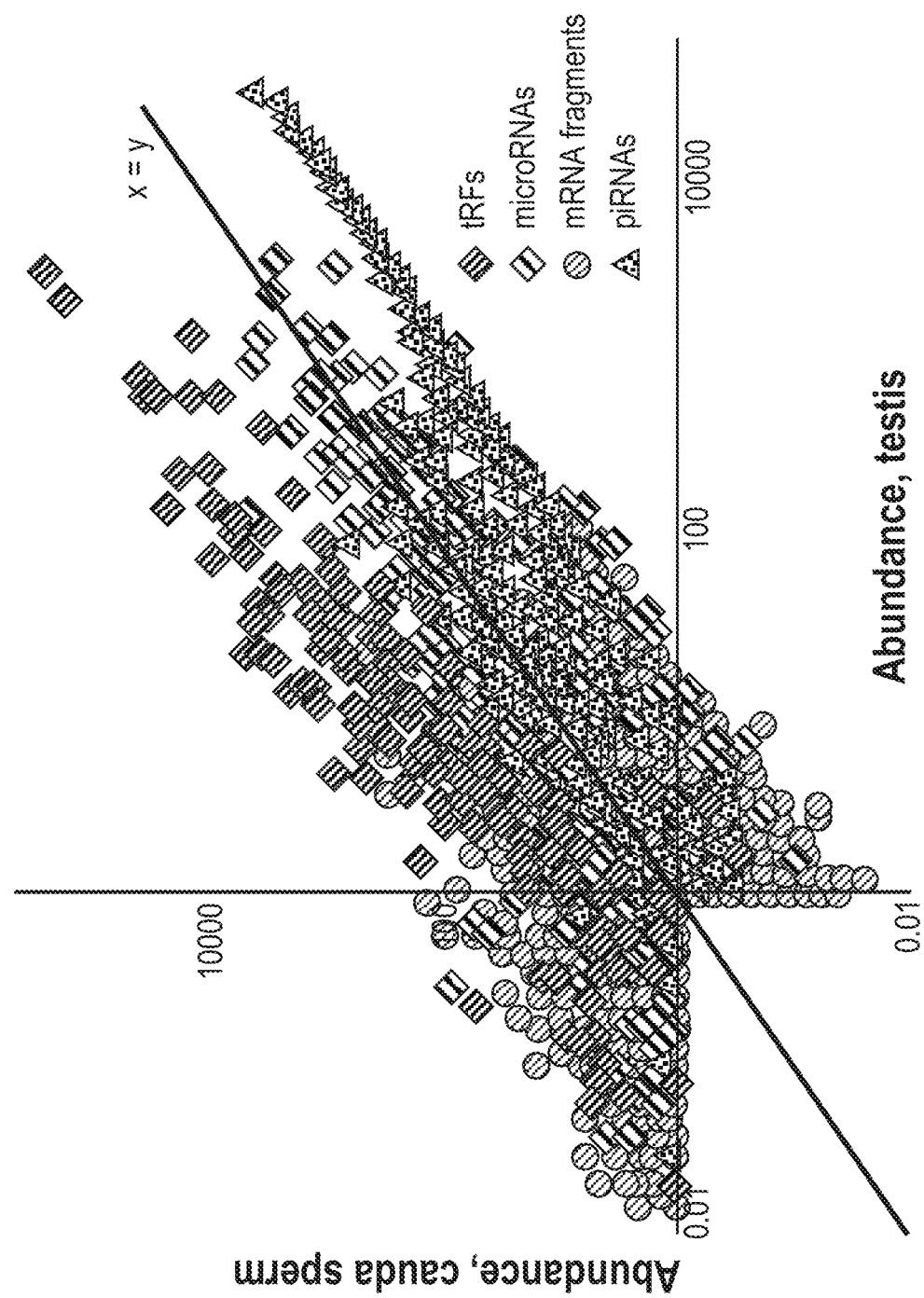
FIGS. 3A-3B show that tRNA cleavage predominantly occurs downstream of the testis.
Figure 4:
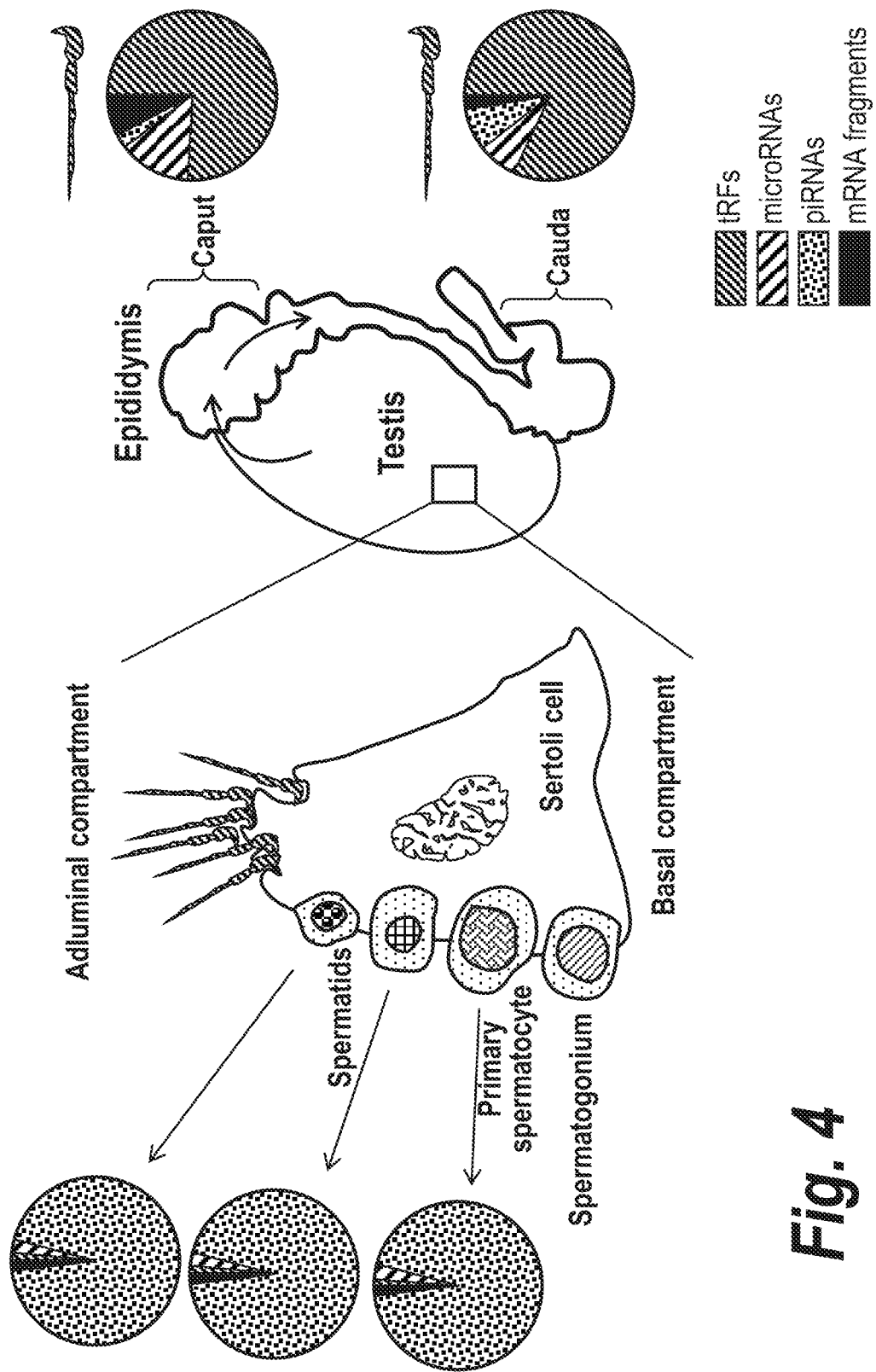
FIG. 4 shows a cartoon showing testicular spermatogenesis and post-testicular maturation in the epididymis. For each purified gamete population, pie charts show the relative abundance of tRNA fragments, microRNAs, piRNAs (defined as reads mapping to either repeatmasker consensus sequences or to unique piRNA clusters), and to Refseq (mRNA fragments), as indicated. Data are shown for three separate fractions of purified testicular germ cells, and for sperm isolated from caput and cauda epididymis, as indicated. Consistent with the low levels of tRNA fragments found in intact testes, spermatocytes and two populations of post-meiotic spermatids carry extremely low levels of tRNA fragments, indicating that the absence of tRNA fragments in intact testis is not a result of contamination by testicular somatic cells.

To explore the biogenesis of tRNA fragments found in sperm, small RNA sequencing data were generated for 18 testis samples from 10-12 week old males, and published data generated from testes of animals at varying ages after birth were reanalyzed (Li, X. Z., et al. 2013. Molecular Cell, 50:67-81). As previously reported (Peng, H et al. 2012. Cell Res. 22:1609-1612), very few small RNAs from testis mapped to tRNAs, with <8% of all <40 nt RNAs (excluding rRNA-mapping reads) mapping to tRNAs (FIG. 3A). Northern blots against 5' ends of tRNAs confirmed barely detectable levels of tRNA cleavage products in testes. The spectrum of specific tRFs also differed between the testis, proximal caput epididymis, and distal cauda epididymis. Similar results were obtained with small RNA profiles of various testicular sperm fractions, including primary spermatocytes, early and late round spermatids, and testicular spermatozoa (FIG. 4). In all four populations very low levels of tRNA fragments were observed, raising the question of where the tRNA fragments present in mature sperm might originate.

In a Northern blot analysis of tRNA cleavage, samples of the epididymis were also included. The epididymis is the convoluted tubular structure in which sperm undergo post-testicular maturation over the course of 1-2 weeks, moving from caput to corpus to cauda epididymis. Curiously, abundant 5' tRFs were identified throughout the epididymis, but not in testes—for both tRNAs analyzed the approximately 30 nt 5' tRNA fragment that was previously sequenced in sperm was observed (Peng, H et al. 2012. Cell Res. 22:1609-1612) and FIG. 1). Levels of tRF-Gly-GCC were similar in the caput and cauda epididymis samples, while tRF-Val-CAC was reproducibly more abundant in the cauda epididymis than in the caput.

Figure 5A:
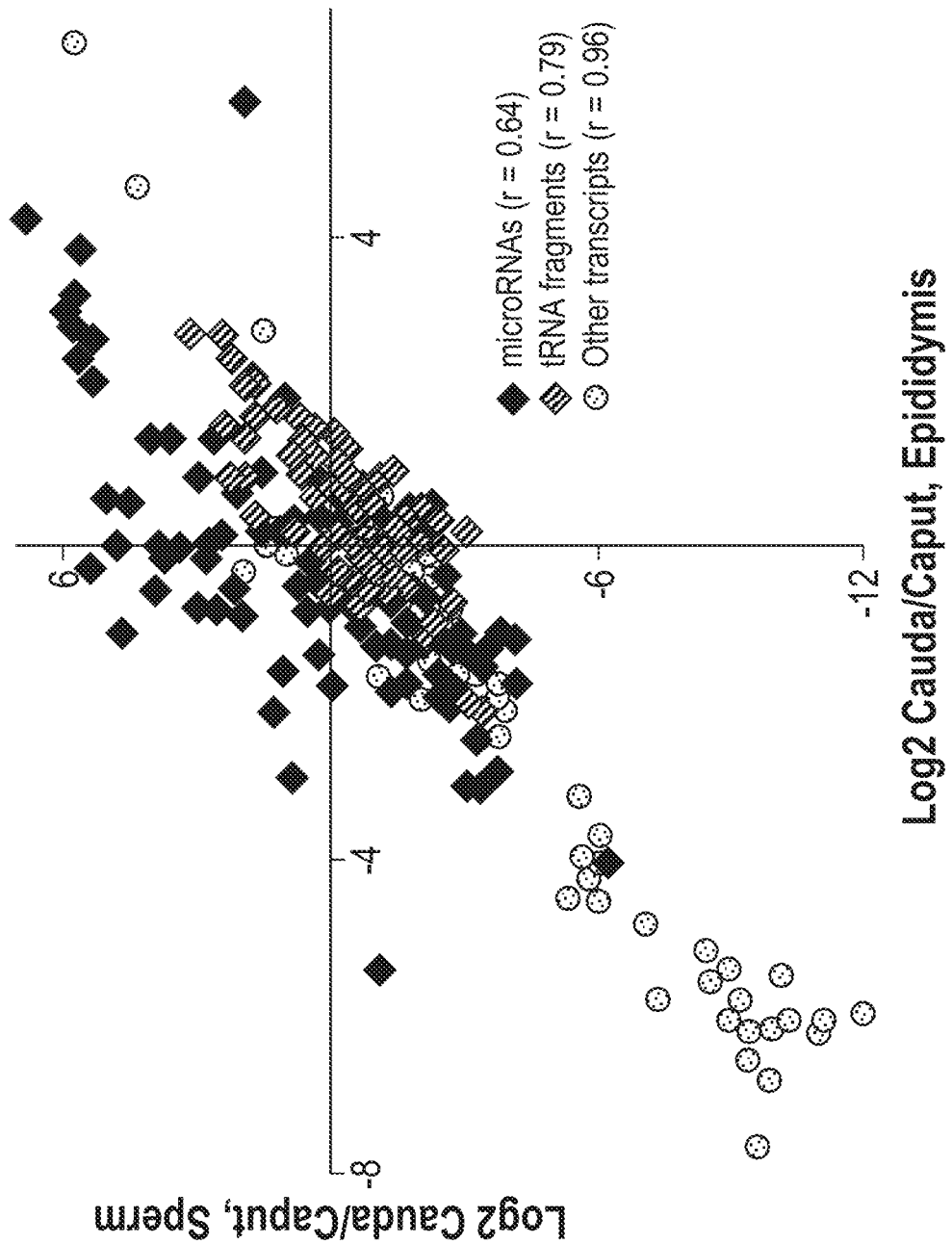
FIGS. 5A-5B show changes in sperm tRF payload during epididymal transit.
Figure 5B:
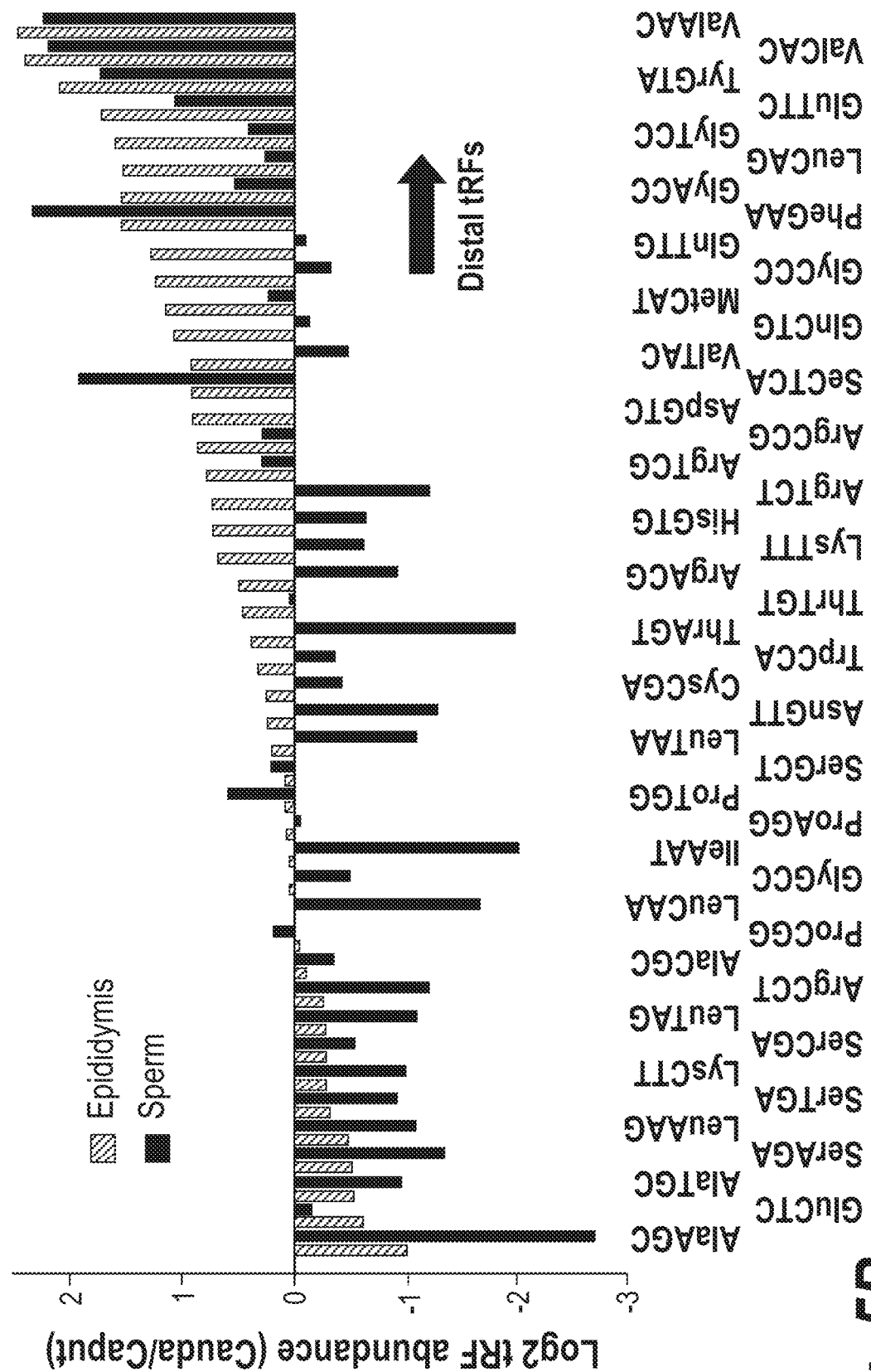

Deep sequencing of small RNAs from caput and cauda epididymal samples confirmed high levels of 5' tRFs in the epididymis. The overall tRF abundance increased from approximately 8% of all small RNA reads (excluding rRNA fragments) in testis to approximately 39% in the caput epididymis to approximately 64% in the cauda epididymis. Results for tRF-Glu-CTC, tRF-Gly-GCC, and tRF-Val-CAC were further validated in additional samples by Taqman. Not only do overall tRF levels increase dramatically more distally in the male reproductive system, but the spectrum of specific tRFs differs between testis, caput epididymis, and cauda epididymis (FIGS. 5A and 5B). For instance, valine tRFs are generally more abundant distally (cauda >caput), whereas levels of various glycine isoacceptor tRFs either peak in the caput epididymis or are high throughout the epididymis (consistent with the described Northern blotting results).

Example 10—Epididymosomes Carry Abundant tRFs that Match the Cauda Sperm RNA Repertoire The finding of robust tRNA cleavage in the epididymis, but not in testis, raises the surprising possibility that the abundant tRFs in cauda sperm might originate from the epididymal epithelium rather than during testicular spermatogenesis. How might such trafficking from the epididymis to maturing sperm occur? During transit through the epididymis sperm gain scores of proteins (Dacheux, J L and F Dacheux. 2013. Reproduction, 147: R27-R42; Sullivan, R, et al. 2013. Reproduction, 146: R21-R35) via fusion with small extracellular vesicles known as epididymosomes (Sullivan, R. et al. 2007. Asian J. Androl. 9: 483-491; Sullivan, R, et al. 2013. Reproduction, 146: R21-R35). Because extracellular vesicles carry functional RNAs in multiple systems (Valadi, H, et al. 2007. Nat. Cell Biol. 9: 654-659; Regev-Rudzki, N, et al. 2013. Cell, 153: 1120-1133; Gibbings, D and O Voinnet. 2010. Trends Cell Biol. 20: 491-501), epididymosomes might be responsible for the dramatic alterations in the sperm RNA payload that occur during epididymal transit.

Figure 6A:
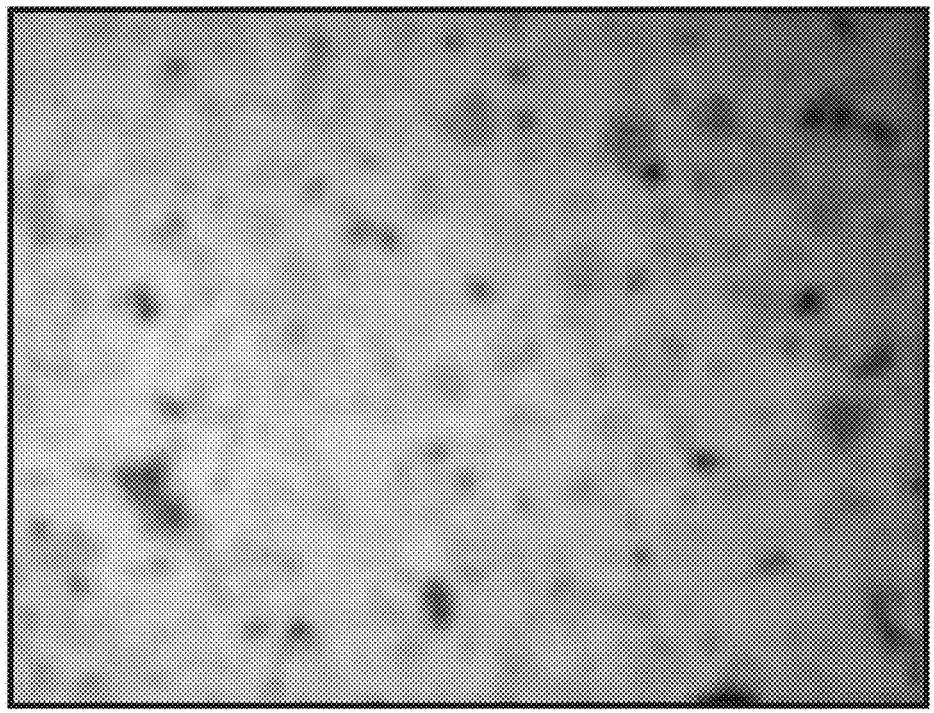
FIGS. 6A-6C show the characterization of cauda epididymosomes.
Figure 6B:
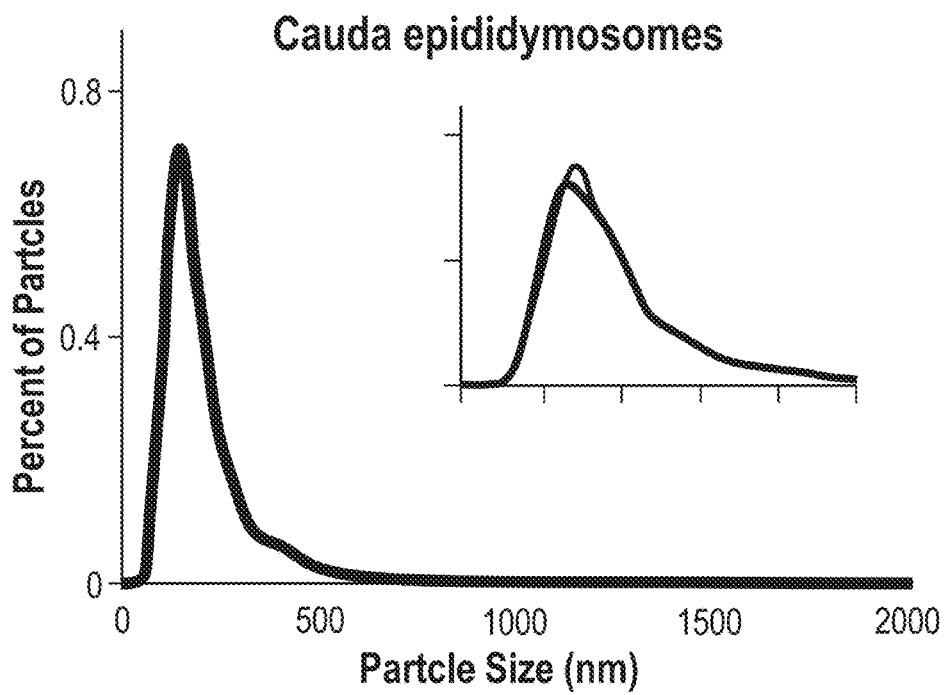

Epididymosomes were purified from the cauda epididymis of 6-12 week old male mice by differential centrifugation. Purified epididymosomes were somewhat heterogeneous in size, with a major size class centered around approximately 150 nm (that occasionally revealed subpeaks of approximately 120 and approximately 170 nm), as well as a far less abundant group of approximately 250-350 nm vesicles (FIGS. 6A and 6B).

Figure 6C:
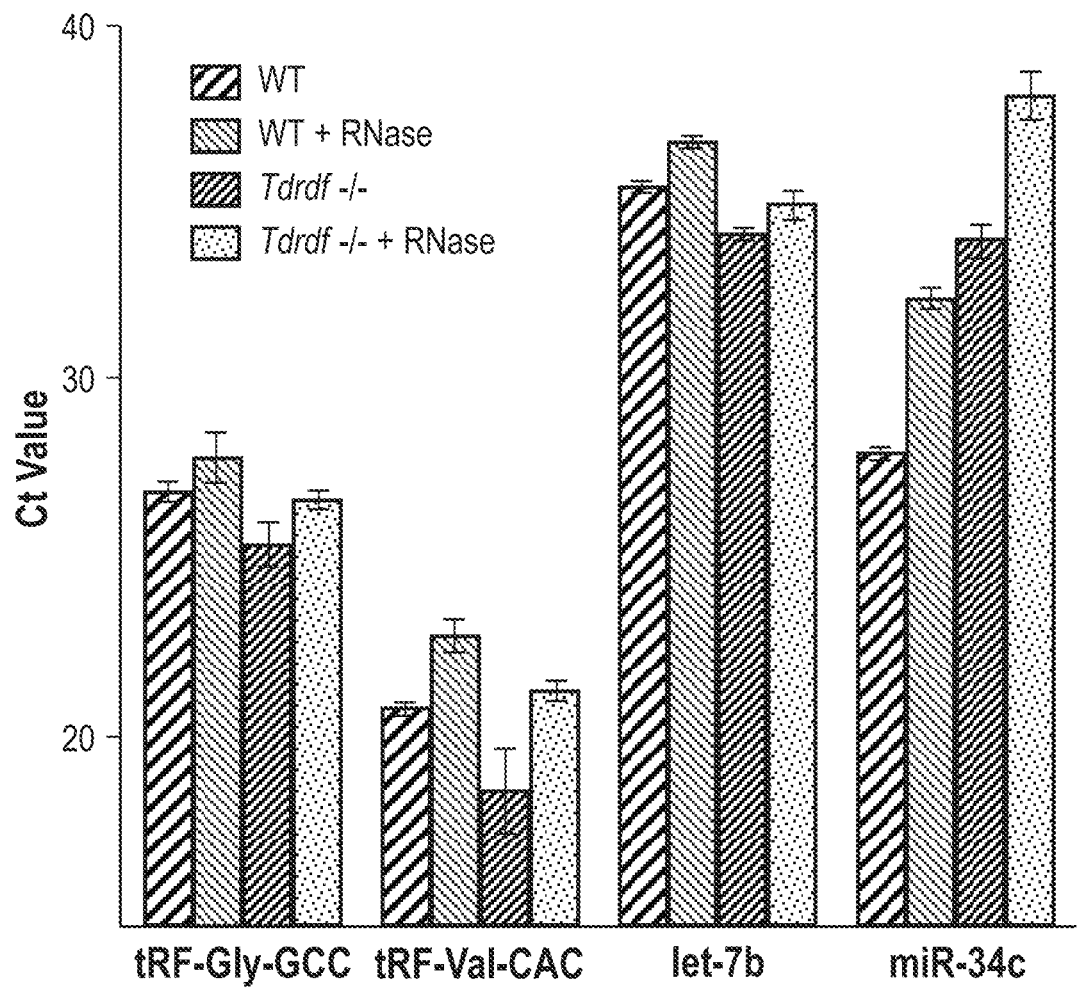
Figure 7:
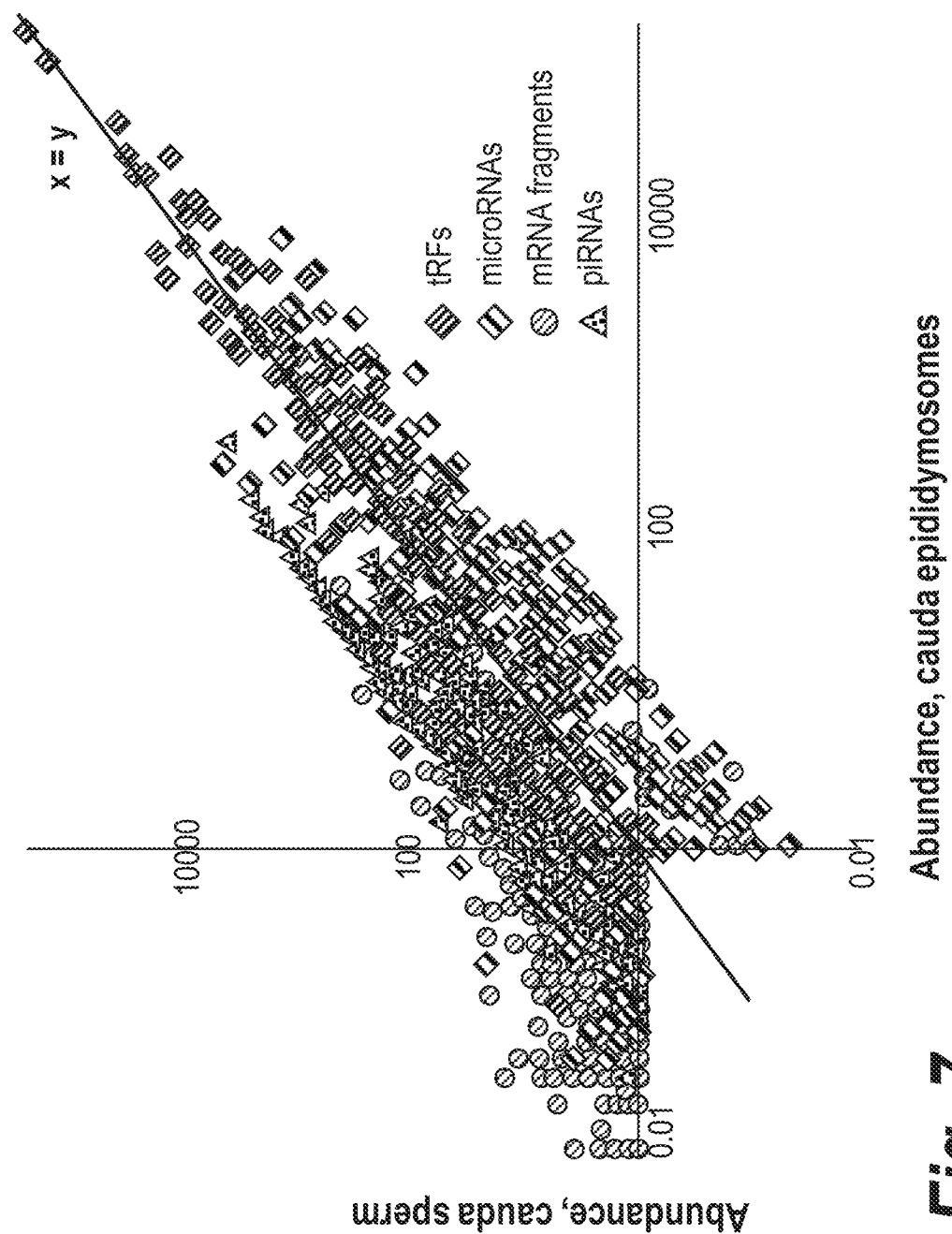
FIG. 7 shows a comparison of small RNA payloads of cauda sperm vs. cauda epididymosomes.

Deep sequencing of small RNA libraries prepared from cauda epididymosome samples (n=15) revealed several size classes of small RNAs, including highly abundant (approximately 87% of total reads) 28-34 nt tRNA fragments as well as lower levels of microRNAs and piRNAs (FIG. 7). RNaseA treatment of epididymosomes prior to RNA extraction had little effect on tRF abundance (FIG. 6C), consistent with these RNAs being present in vesicles or otherwise protected, rather than free in the epididymal lumen. In addition, to ensure that the vesicles purified from the epididymis were not generated from maturing sperm, epididymosomes were isolated from male tdrd1−/− mice (in which spermatogenesis is impaired), confirming high levels of tRFs in these vesicles (FIG. 6C).

Small RNAs found in epididymosomes closely mirrored those found in cauda sperm. For example, the most abundant RNA species in epididymosomes were 5' fragments of tRNA-Glu-CTC, followed by the 5' ends of tRNA-Val-CAC/AAC and tRNA-Gly-GCC/CCC. Overall, the entire RNA payload of mature sperm was remarkably well-correlated (r=0.98) with the RNAs present in purified epididymosomes (FIG. 7). The small RNAs that were enriched in sperm relative to epididymosomes included those mapping to repeat elements or unique piRNA clusters, as well as fragments of mRNAs involved in spermatogenesis (Prm1, for example). These RNAs thus almost certainly reflect RNAs gained during spermatogenesis, but the remaining RNAs, which represented the vast majority of RNAs in cauda sperm, were found at similar levels in sperm and in epididymosomes. Epididymosomes carried a highly similar RNA payload to that found in sperm, suggesting that these vesicles may be responsible for delivering tRNA fragments and perhaps other small RNAs to maturing sperm.

Example 11—Vesicles Carrying tRNA Fragments Originate in the Epididymis

As fluid flow in the epididymis proceeds from testis through the epididymis and onwards to the vas deferens, luminal contents of the cauda epididymis could reflect a mixture of species secreted from a variety of upstream locations. In order to further investigate the origin of tRF-containing vesicles in the reproductive tract, epididymosomes were purified from the caput epididymis (FIGS. 8A-8E). Purified caput epididymosomes had a similar size distribution to that of cauda epididymosomes, although the modal size of cauda epididymosomes was slightly larger than that of caput epididymosomes, and cauda epididymosomes also included larger (250-500 nm) particles. Small RNA populations from caput epididymosomes (n=7) were isolated and subject to deep sequencing as above. Intriguingly, cauda and caput epididymosomes differed markedly in the relative abundance of microRNAs versus tRNA fragments. The relatively low abundance of tRFs in caput epididymosomes strongly argues for an epididymal origin for the abundant tRFs in cauda epididymosomes, as any vesicles originating in the testis should if anything be over-represented in the caput epididymosome samples relative to the cauda.

Beyond these bulk changes in the abundance of general classes of small RNAs, marked differences in the specific RNAs in each epididymosome population were also observed. While not particularly abundant overall, mRNA fragments as a class were comparatively more abundant in caput epididymosomes, with the greatest enrichment for fragments of mRNAs that are highly expressed in the caput epididymis (Johnston, D S. 2005. Biol. Reprod. 73: 404-413), such as Lcn5, Defb12, and Adam28. MicroRNAs were overall more abundant in caput epididymosomes, with individual microRNAs varying in their relative enrichment in the two samples. tRNA fragments varied considerably in relative abundance as well, with cauda epididymosomes gaining abundant tRF-Val-CAC, tRF-Val-AAC, and tRF-Gly-CCC while exhibiting relative "loss" of isoleucine and leucine tRFs. Overall, differences between caput and cauda epididymosomes in small RNA abundance were moderately well-correlated to the analogous differences between epididymal epithelium samples, supporting the hypothesis that epididymosomes from a given luminal region likely originate in the underlying epithelium. Together, these observations strongly support a model in which extracellular vesicles are secreted throughout the male reproductive tract, with different sections of the tract releasing different RNA cargos.

Example 12—Epididymosomes Deliver Small RNAs to Sperm

The strong correlation between the small RNA cargo of epididymosomes and that of cauda sperm, along with published evidence that epididymosomes can fuse with sperm and deliver other macromolecular cargo (Sullivan, R. et al. 2007. Asian J. Androl. 9: 483-491; Sullivan, R, et al. 2013. Reproduction, 146: R21-R35), suggests that epididymosomes are responsible for shaping the RNA payload of maturing sperm. In order to isolate mature sperm that had not yet completed epididymal transit, sperm from the caput epididymis was purified and subjected them to small RNA-Seq. Caput sperm (n=10) carried high levels of tRNA fragments indicating that the dramatic increase in tRNA fragment abundance in sperm relative to testis occurs either very late during testicular spermatogenesis, or during the first approximately 3-5 days of epididymal transit. That said, variation between caput and cauda sperm samples revealed extensive differences in the abundance of specific small RNAs. Examining tRNA fragment dynamics in detail, proximal-distal biases for specific tRFs along the epididymis, and in epididymosomes, were also reflected in tRF dynamics in maturing sperm. Ratios of tRFs (as well as other small RNA classes) between caput and cauda sperm were well-correlated with the caput/cauda ratios observed in epididymosomes and epididymis (FIG. 5). This does not result from artefactual contamination of caput sperm samples with epididymosomes, as sequencing of small RNAs from caput sperm samples isolated with or without a step of washing with detergent revealed that this washing protocol easily removed epididymosome-enriched RNAs.

In all three sample types analyzed—epididymis, epididymosomes, and sperm—key tRFs exhibited consistent biases in their enrichment along the proximal-distal axis of the epididymis. A small subset of tRFs was generally enriched in the proximal epididymis, with most leucine and isoleucine isoacceptors generally being enriched in caput samples of epididymis, epididymosomes, and sperm. In contrast, a dramatic apparent gain of tRF-Val-AAC/CAC between caput and cauda samples was observed, which was validated by Taqman in multiple independent samples. These data support the hypothesis that fusion of caput sperm with cauda epididymosomes results in gain of tRF-Val-CAC and other RNAs, but could also be explained if small RNAs are globally degraded in sperm during epididymal transit, with tRF-Val-CAC and related species being resistant to this degradation.

Figure 9A:
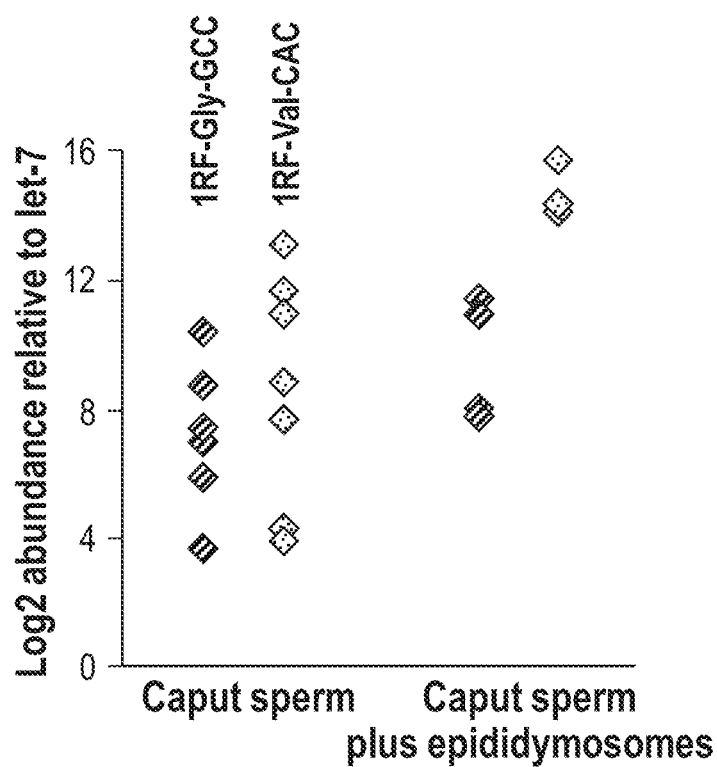
FIGS. 9A and 9B show our ability to deliver small RNAs to immature sperm via fusion with epididymosomes.
Figure 9B:
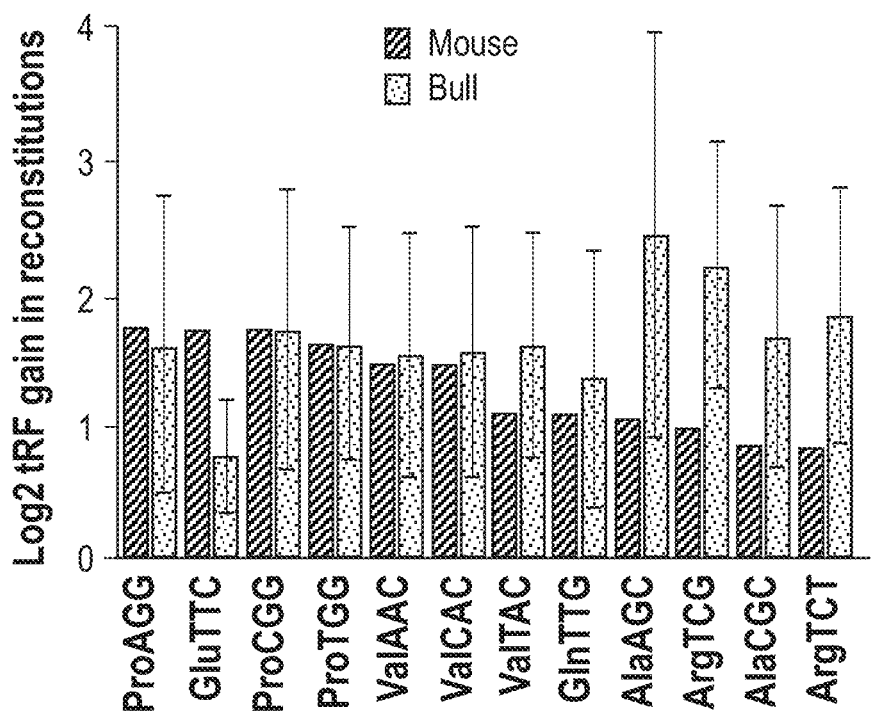

To determine whether epididymosomes can deliver their RNAs to caput sperm, caput sperm were stringently purified over Percoll gradients, incubated them with cauda epididymosomes at 37° C. for 1 or 2 hours, then pelleted and washed the "reconstituted" sperm (FIG. 9). Epididymosomal fusion with caput sperm was observed to be sufficient to deliver both tRF-Val-CAC and multiple other cauda-enriched tRFs to caput sperm (FIG. 9A), confirming that tRF-bearing epididymosomes either are capable of fusing with sperm to deliver their small RNA cargo (Caballero, J N et al. 2013. PLOS ONES 8: e65364) or adhere to caput sperm strongly enough to resist removal by several consecutive washing steps. These results were repeated using the more abundant caput sperm samples obtainable from the bull *B. taurus*, with cauda epididymosome fusion with caput sperm (n=4) resulting in delivery of tRF-Val-CAC and other tRFs to relatively immature caput sperm (FIG. 9B).

Taken together, these experiments are most consistent with a mechanism of RNA biogenesis in mammalian sperm in which tRFs generated in the epididymis are trafficked to sperm in epididymosomes.

Example 13—Functions of Sperm tRNA Fragments in Stem Cells and in Embryos

Next, potential downstream targets of the small RNAs in sperm were considered, initially using embryonic stem (ES) cells as an experimental system amenable to mechanistic analysis. Here, the function of specific tRFs was interfered with using antisense LNA-containing oligonucleotides in ES cell culture, and genome-wide analysis of RNA abundance (using Affymetrix microarrays and RNA-Seq) was carried out to assay the consequences of tRNA fragment inhibition. The majority of antisense oligos had no effect on mRNA abundance, suggesting that the targeted tRFs are not functional in ES cells, or that they exerted regulatory effects that were not assayed by mRNA abundance.

Figure 10A:
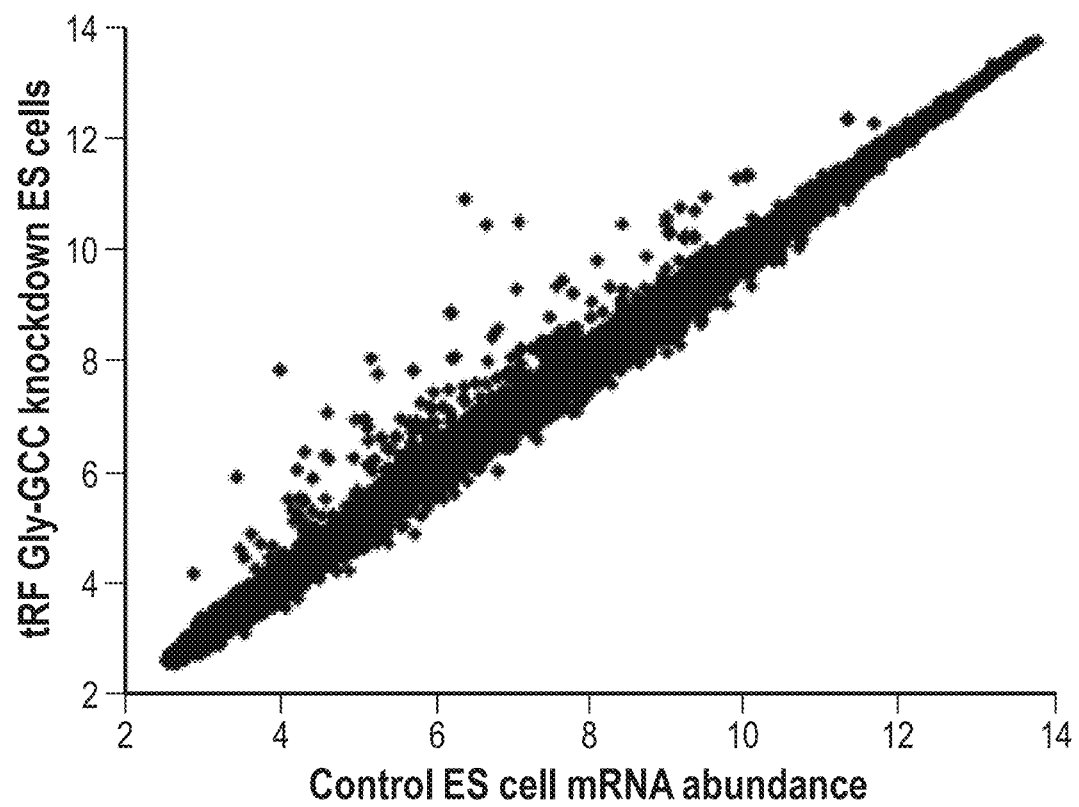
FIGS. 10A-10F show that tRF-Gly-GCC regulates MERVL-driven transcripts in the early embryo.
Figure 10B:
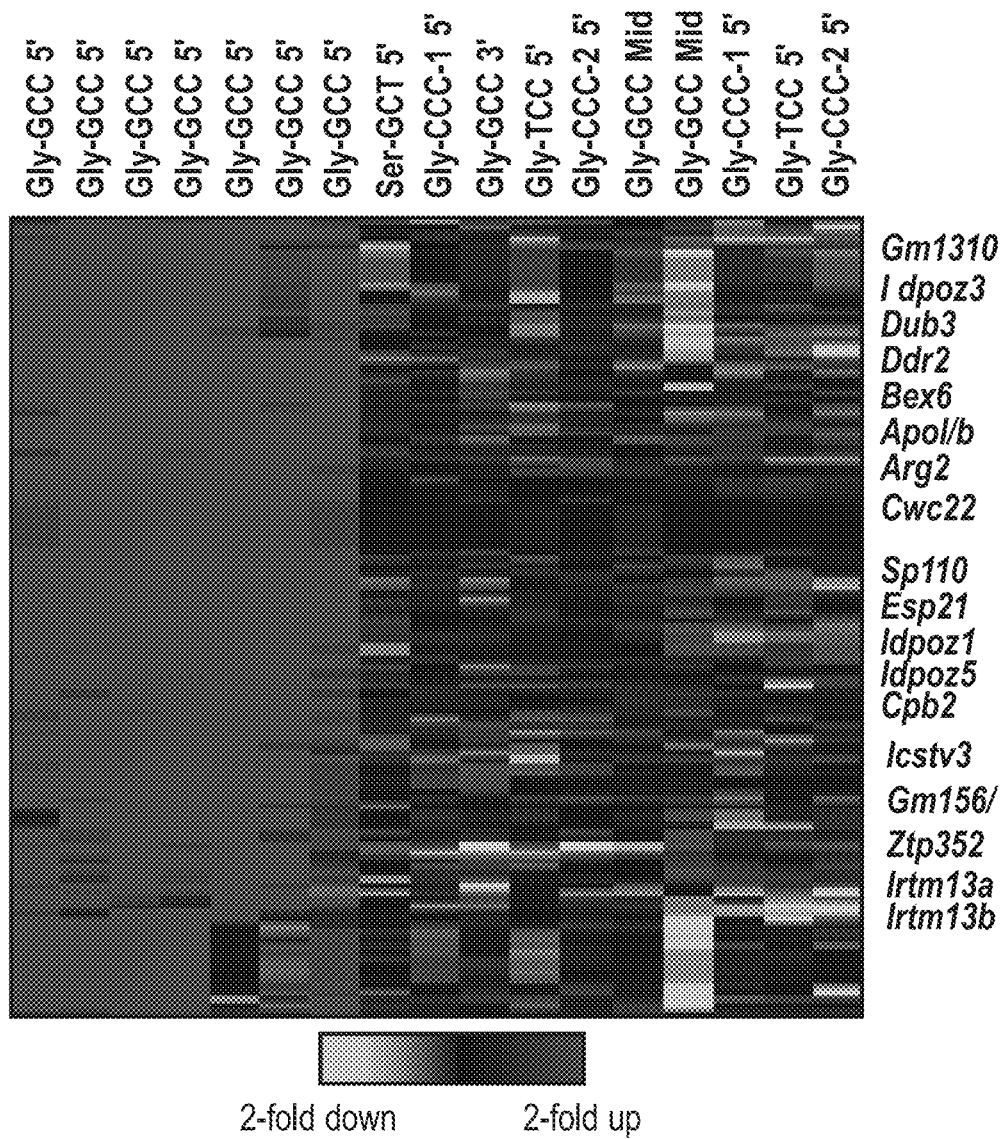
Figure 10C:
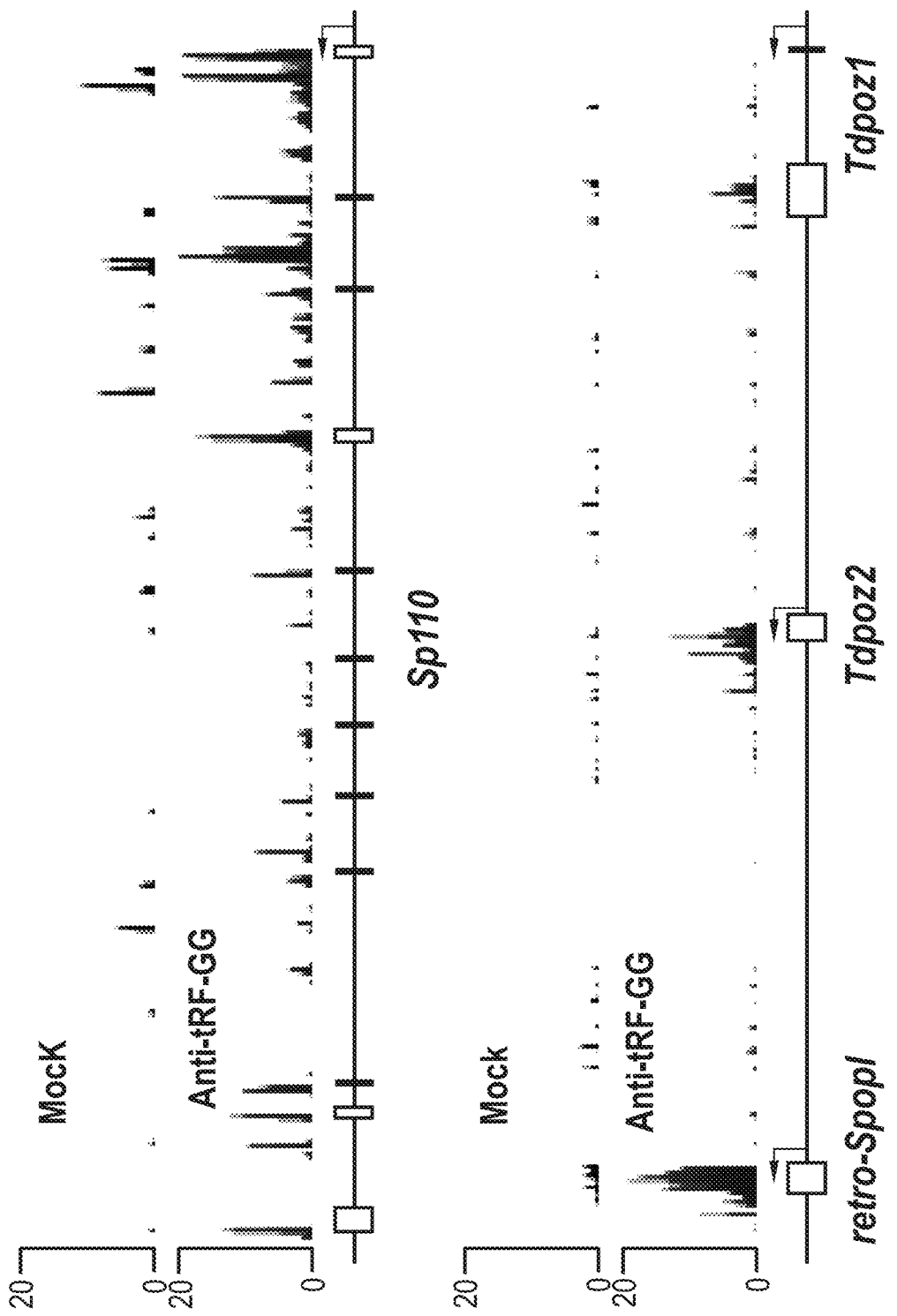
Figure 10D:
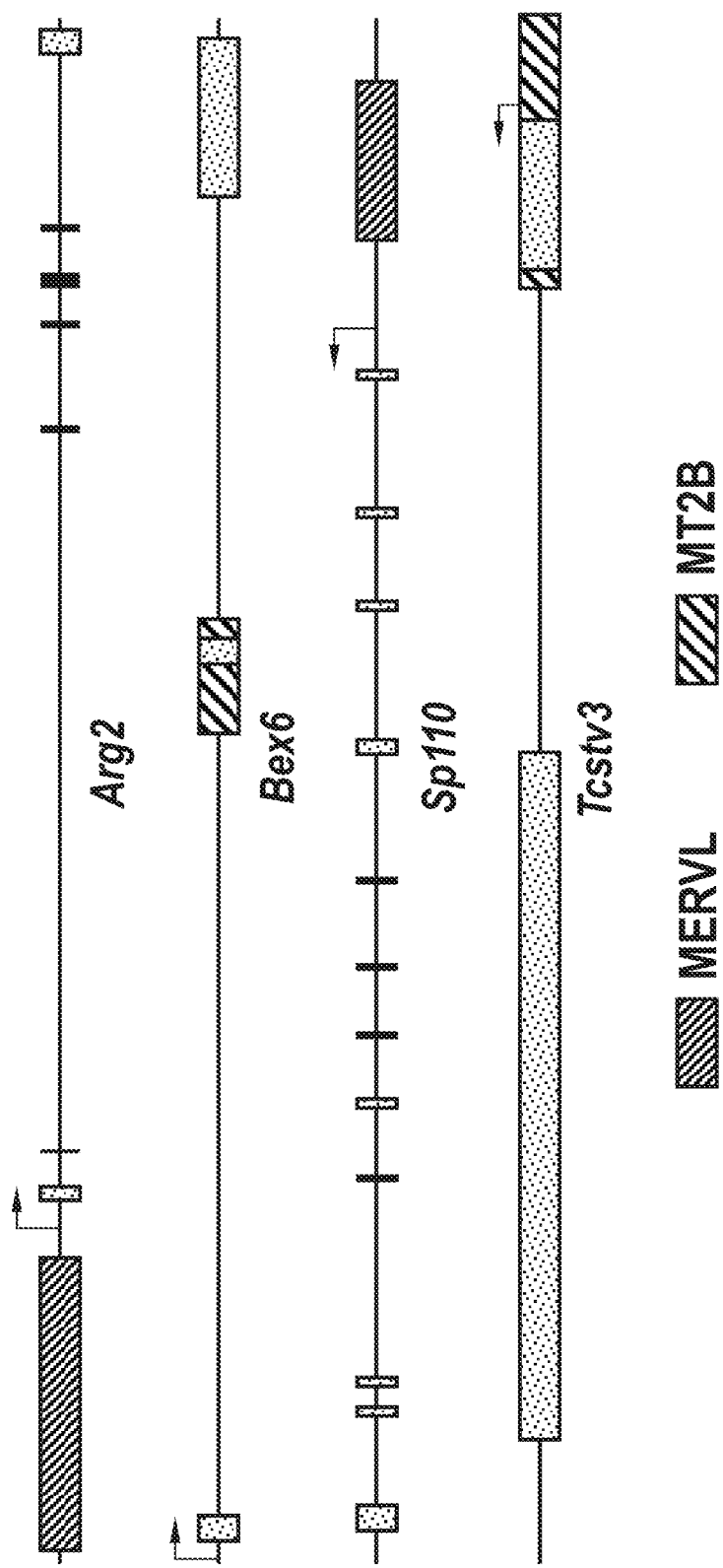

In contrast, interfering with tRF-Gly-GCC function using an LNA-containing antisense oligonucleotide resulted in dramatic upregulation of approximately 50 genes, with several genes being upregulated over 10-fold (FIGS. 10A-10C). Upregulation of these genes was consistently observed by microarray in seven separate transfections, and further confirmed in four additional replicates by RNA-Seq. These genes were unaffected by antisense LNA oligos directed against the 5' end of tRNA-Ser-GCT, the 5' ends of other tRNA-Gly isoacceptors, or against the middle or the 3' end of tRNA-Gly-GCC (FIG. 10B). This last finding strongly suggests that changes in gene expression caused by interfering with the 5' fragment of tRNA-Gly-GCC are unlikely to be an artifact of interfering with the function of the intact tRNA. Surprisingly, all the genes upregulated in tRF-Gly-GCC knockdowns are highly expressed in 2-cell and 4-cell embryos, and have been shown to be regulated by the long terminal repeat (LTR) of an endogenous retroelement known as MERVL (Macfarlan, T S, et al. 2011. Genes Dev. 25:594-607; Macfarlan, T S, et al. 2012. Nature 487: 57-63) (FIG. 10D). Transfection studies using ES cell lines carrying fluorescent reporters driven by the LTR of MERVL revealed a modest increase (approximately 25-40%) in the fraction of "MERVL positive" cells upon tRF-Gly-GCC inhibition, independently confirming the link between tRF-Gly-GCC and the MERVL LTR.

Figure 10E:
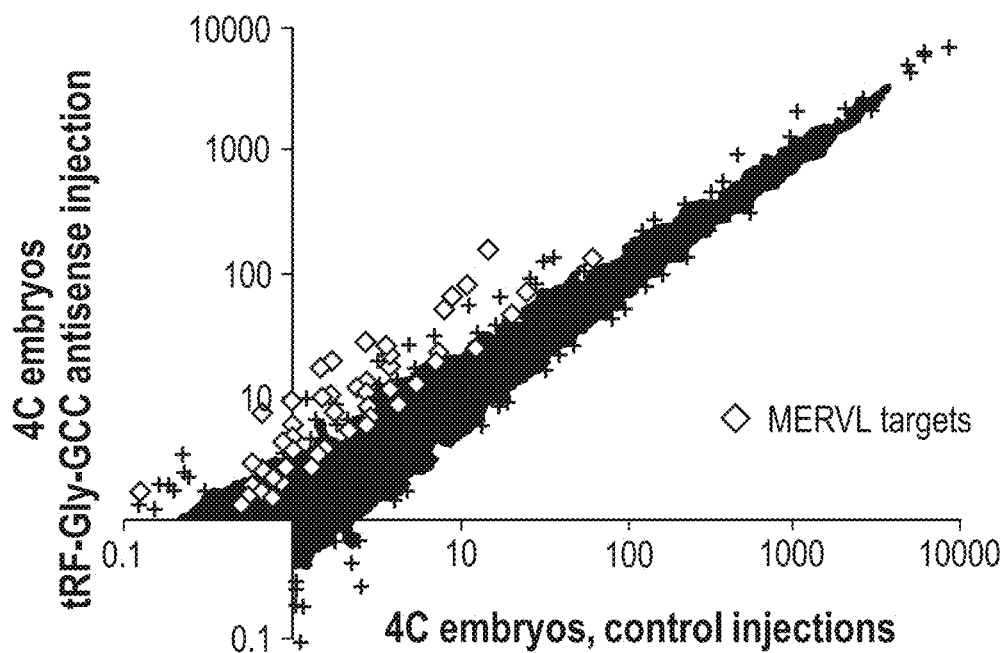
Figure 10F:
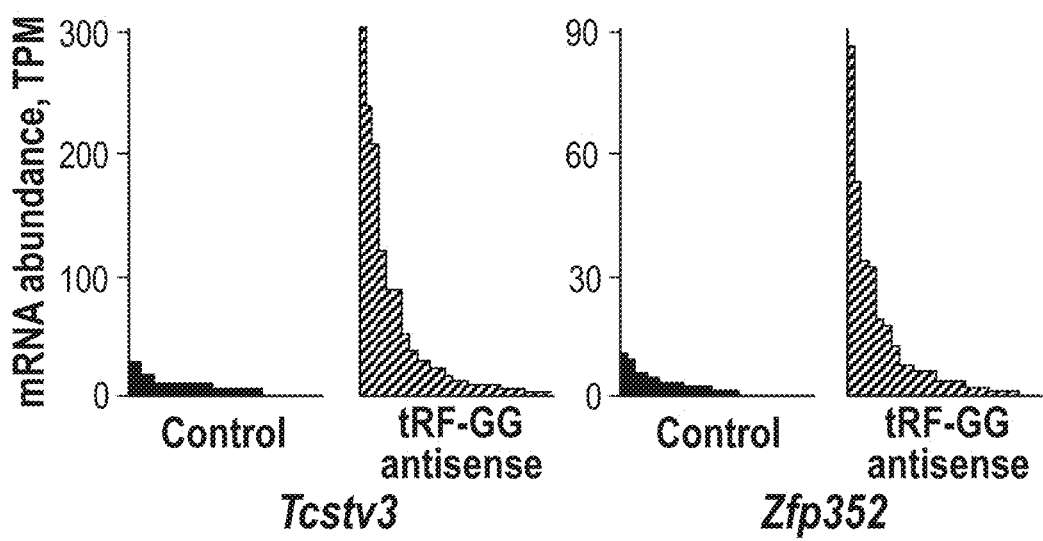

To determine whether the effects of tRF-Gly-GCC inhibition observed in tissue culture also hold in a more physiological context, zygotes (n=27) were microinjected with an antisense oligo directed against tRF-Gly-GCC. These embryos were then allowed to develop to the 4-cell stage and subjected to single embryo RNA-Seq (Ramskold, D., et al. 2012. Nat. Biotechnol. 30: 777-782; Shalek, A K et al. 2013. Nature, 498: 236-240). Strikingly, significant upregulation of 72 transcripts in embryos subject to tRF-Gly-GCC inhibition was observed compared to control embryos (n=28), with the majority of upregulated genes having previously been identified as MERVL targets (Macfarlan, T S, et al. 2012. Nature 487: 57-63) (FIGS. 10E and 10F).

Example 14—Paternal Dietary Effects on Preimplantation Development

This example shows that paternal diet effects preimplantation development. The data are shown in FIGS. 11 and 12. Given the robust connection between a diet-regulated small RNA and a highly specific set of target genes, could tRF-Gly-GCC targets be affected in preimplantation embryos generated using sperm from animals consuming Control or Low Protein diet? Single-embryo RNA-Seq (Ramskold, D., et al. 2012. Nat. Biotechnol., 30: 777-782; Shalek, A K, et al. 2013. Nature, 498: 236-240) of individual embryos cultured to various stages of development robustly clustered embryos by developmental stage (FIGS. 11A-B), with the first two principal components of the dataset representing oocyte-derived transcripts (PC1), and embryonic genome activation (PC2).

Figure 11A:
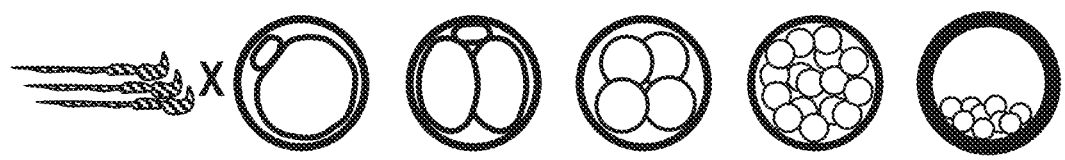
FIGS. 11A-F show paternal dietary effects on preimplantation development.
Figure 11B:
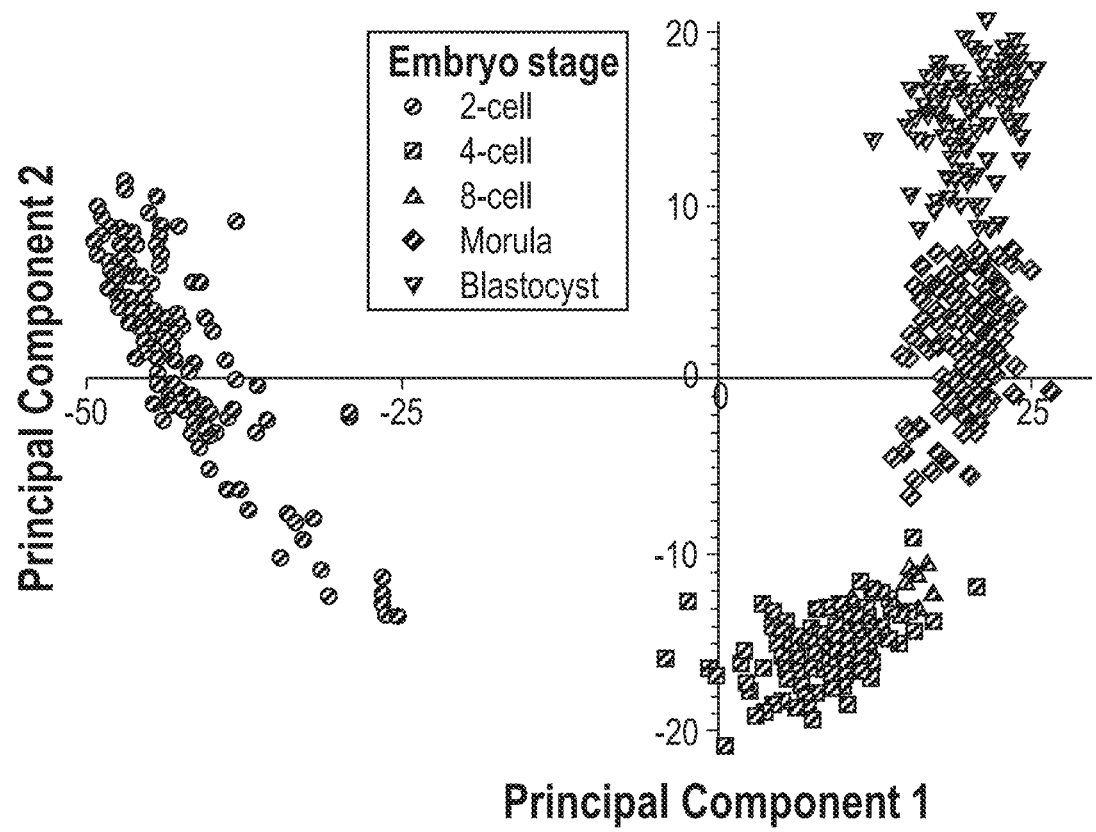
Figure 11C:
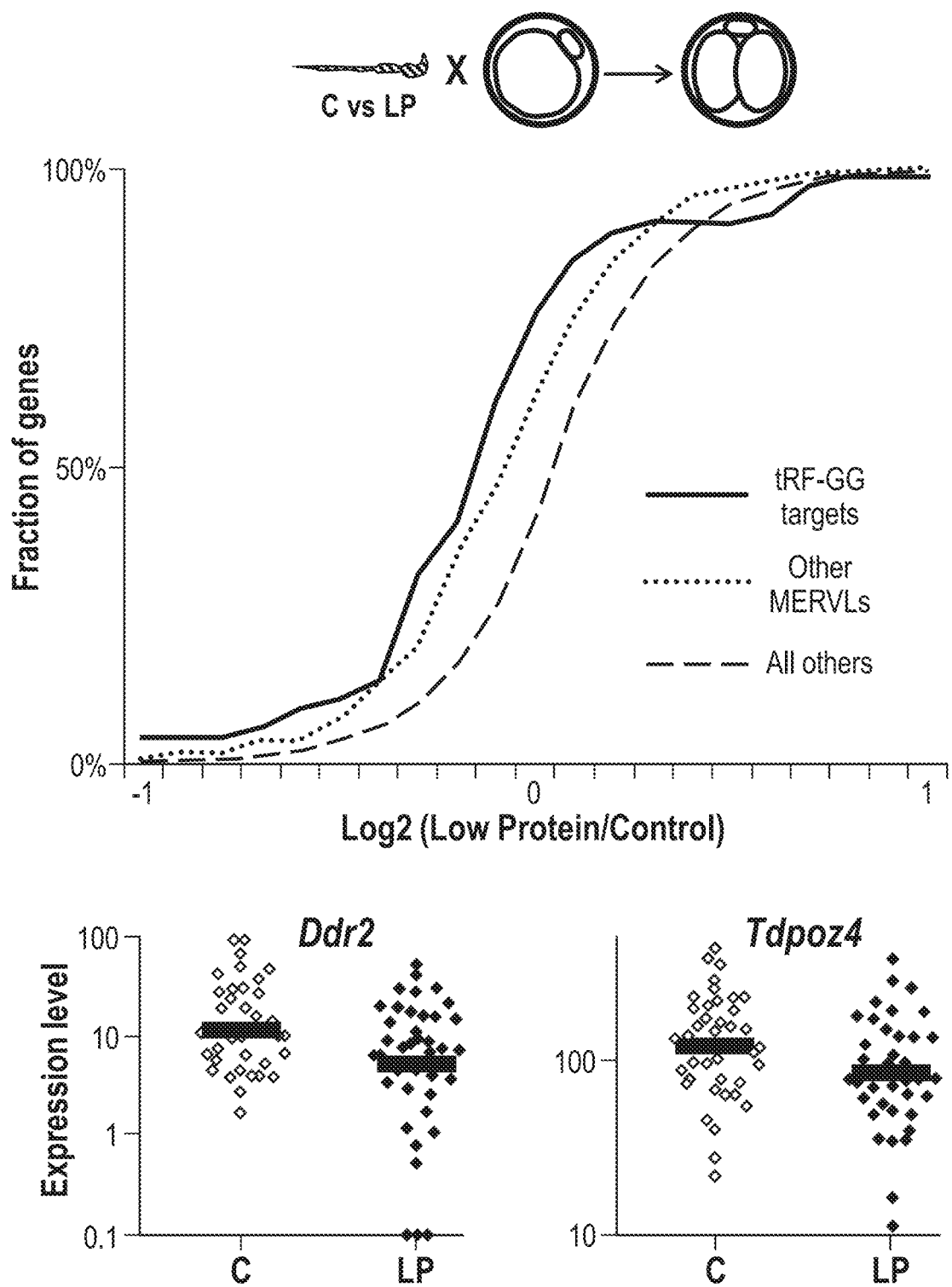
Figure 11D:
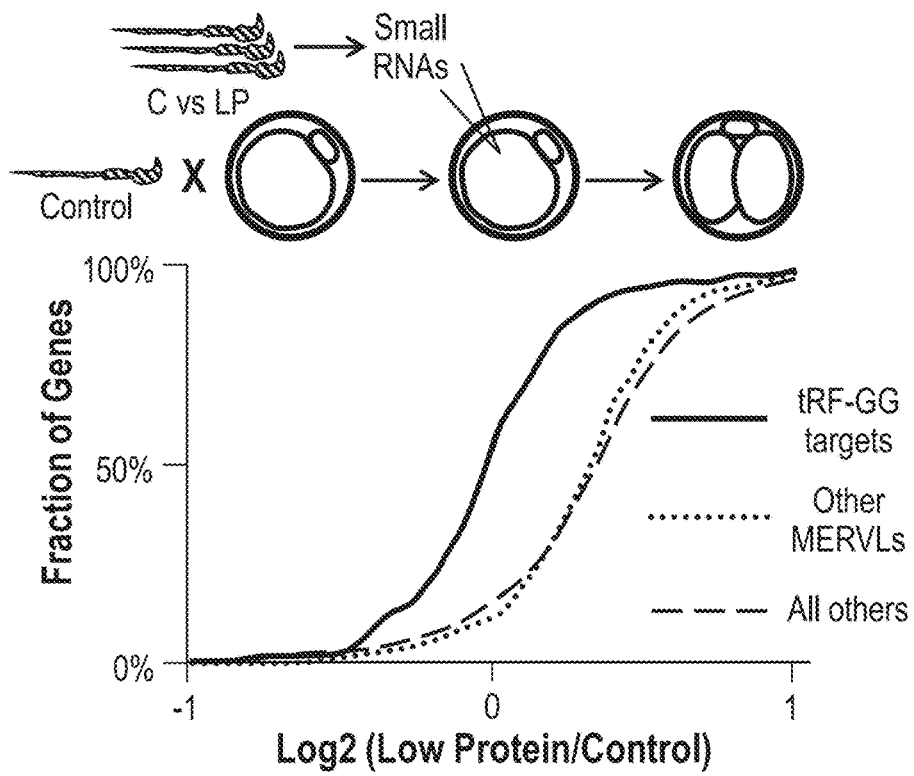
Figure 11E:
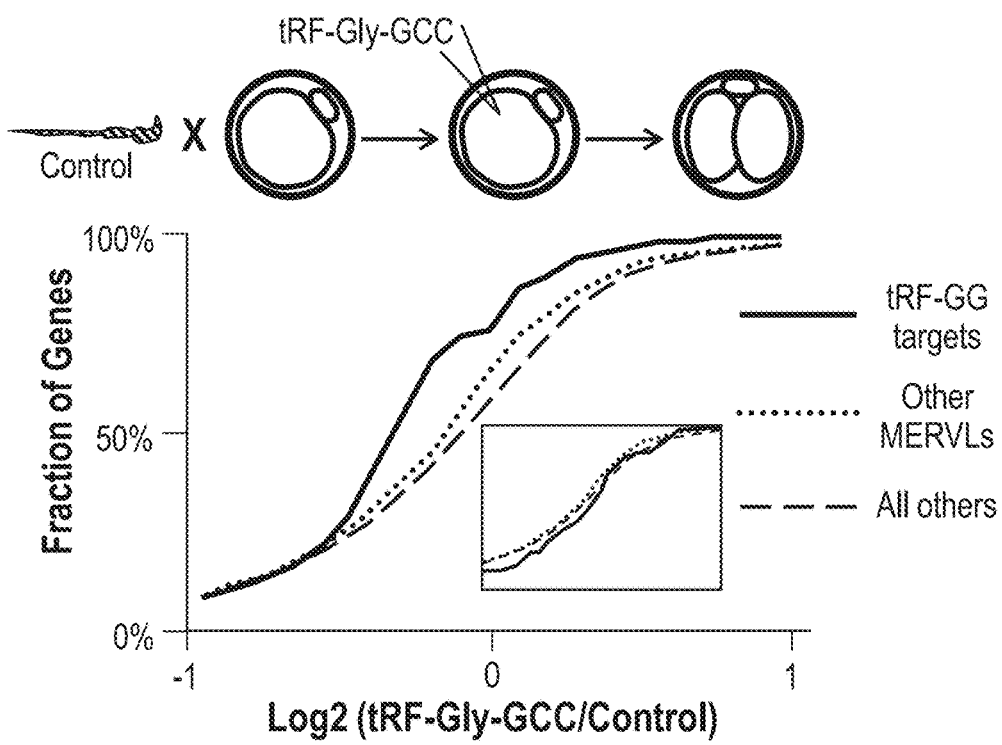
Figure 11F:
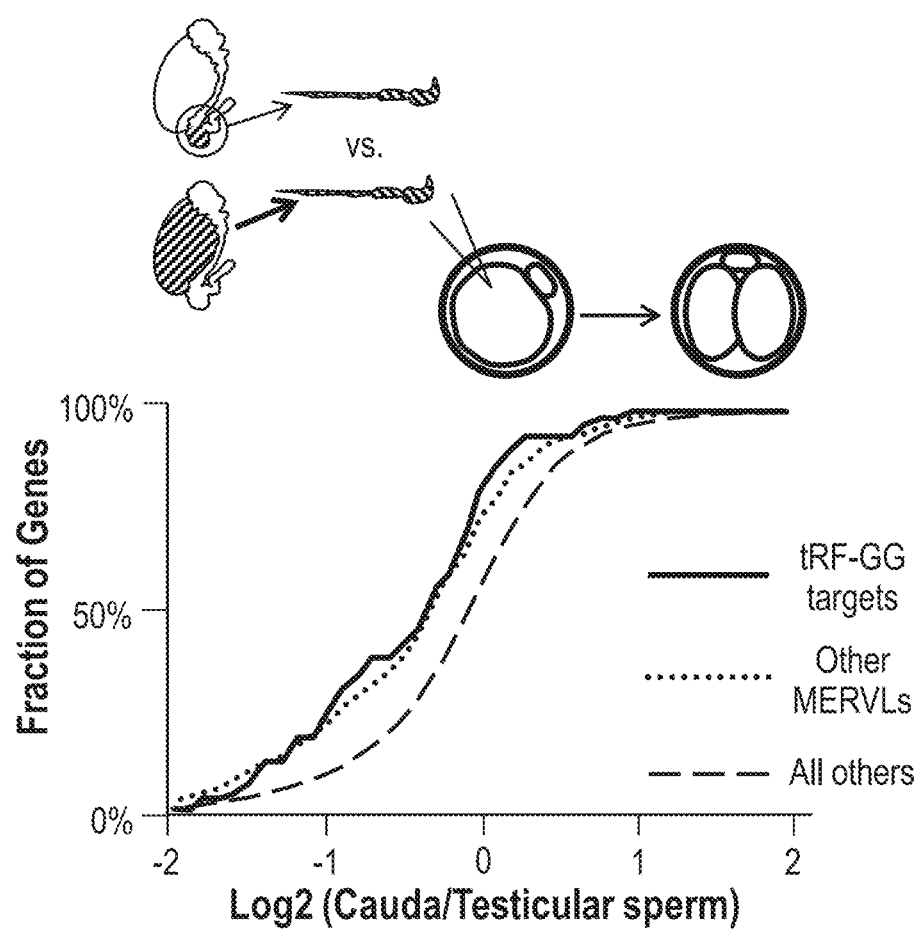

As single embryo RNA-Seq data are not suitable for identification of modest changes in individual mRNAs, consistent changes in larger genesets were searched: the subset of MERVL targets that respond to tRF-Gly-GCC inhibition (FIG. 10) and remaining MERVL targets (Macfarlan, T S, et al. 2012. Nature, 487: 57-63). At the 2-cell stage both tRF-Gly-GCC targets and remaining MERVL targets were downregulated in Low Protein embryos relative to Control (FIG. 11C), consistent with the hypothesis that tRF-Gly-GCC in sperm affects expression of MERVL targets in early embryos. Several independent tests of this hypothesis were carried out. First, control zygotes were injected with <40 nt RNA populations purified from Control and Low Protein sperm, finding that Low Protein RNAs could inhibit tRF-Gly-GCC targets in 2-cell embryos (FIG. 11D) indicating that paternal diet can affect preimplantation gene regulation via RNAs in sperm. Second, further defining the relevant RNA from Low Protein sperm, microinjection of a synthetic tRF-Gly-GCC oligo resulted in repression of MERVL target genes in 2-cell embryos (FIG. 11E). Finally, as tRFs in sperm are gained during epididymal transit, embryos were generated via intracytoplasmic sperm injection (ICSI) using testicular spermatozoa or cauda sperm. Consistent with the higher levels of tRF-Gly-GCC in cauda sperm, embryos generated using cauda sperm expressed MERVL targets at lower levels than embryos generated using testicular sperm (FIG. 11F). Together, these findings all support the hypothesis that tRF-Gly-GCC in sperm is capable of delaying or repressing MERVL target expression in 2-cell embryos.

Lastly, tRF-Gly-GCC is observed to be one of several abundant RNAs regulated by Low Protein diet, and MERVL-driven genes are not the only diet-responsive genes in preimplantation embryos. Most notably, ribosomal protein genes (RPGs) were downregulated in Low Protein embryos, and, correspondingly, Low Protein embryos develop slower than Controls (FIG. 12; discussed below) (Mitchel, M, et al. 2011. Fertil. Steril., 95: 1349-1353).

Figure 12A:
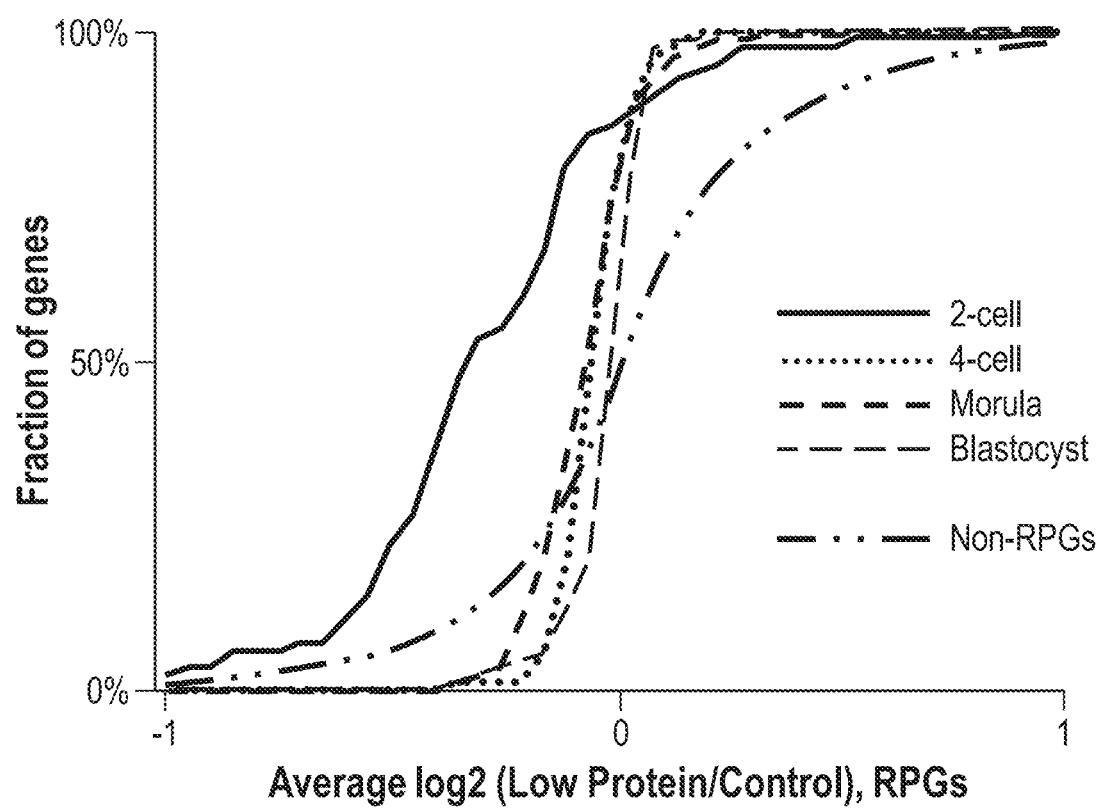
FIGS. 12A-12H show paternal dietary effects on preimplantation development.
Figure 12B:
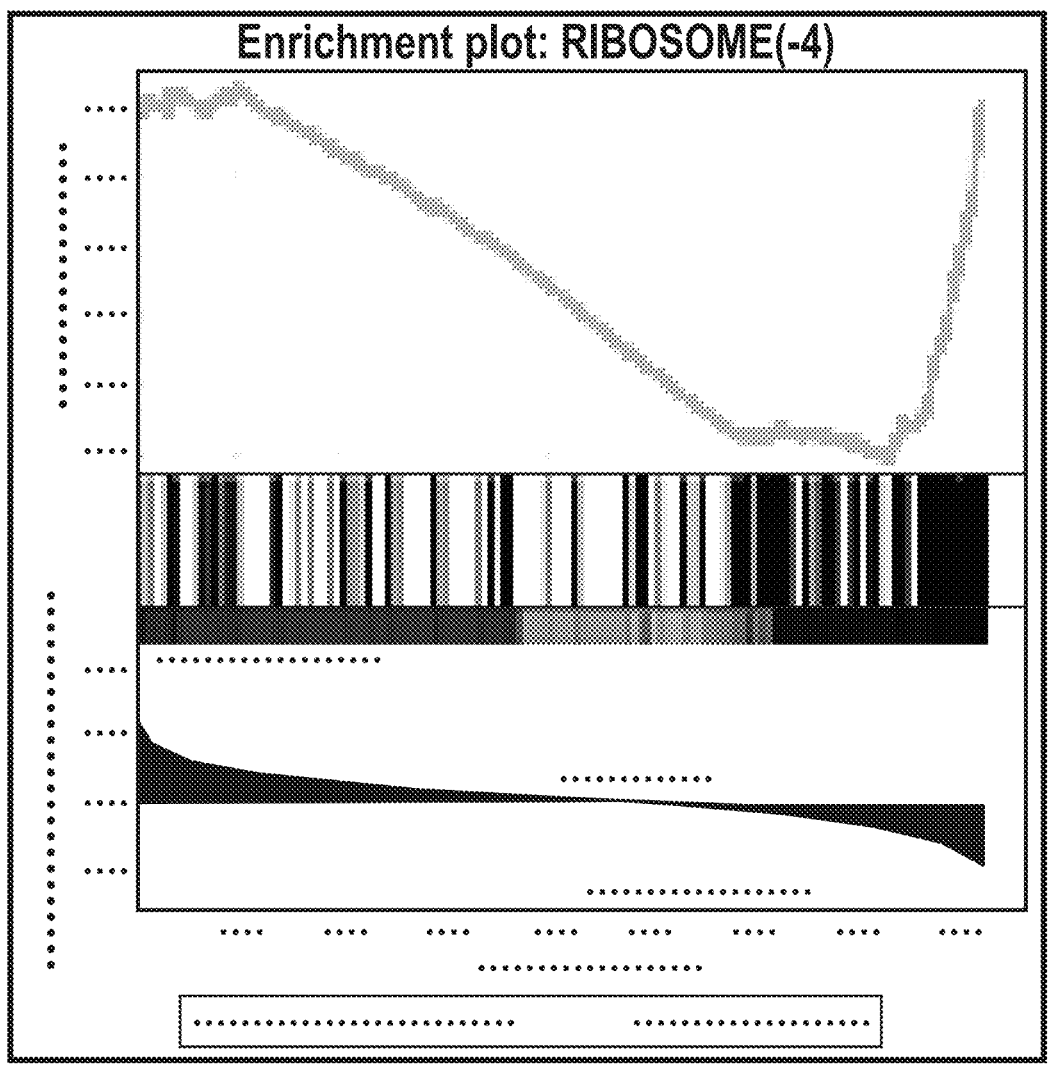
Figure 12C:
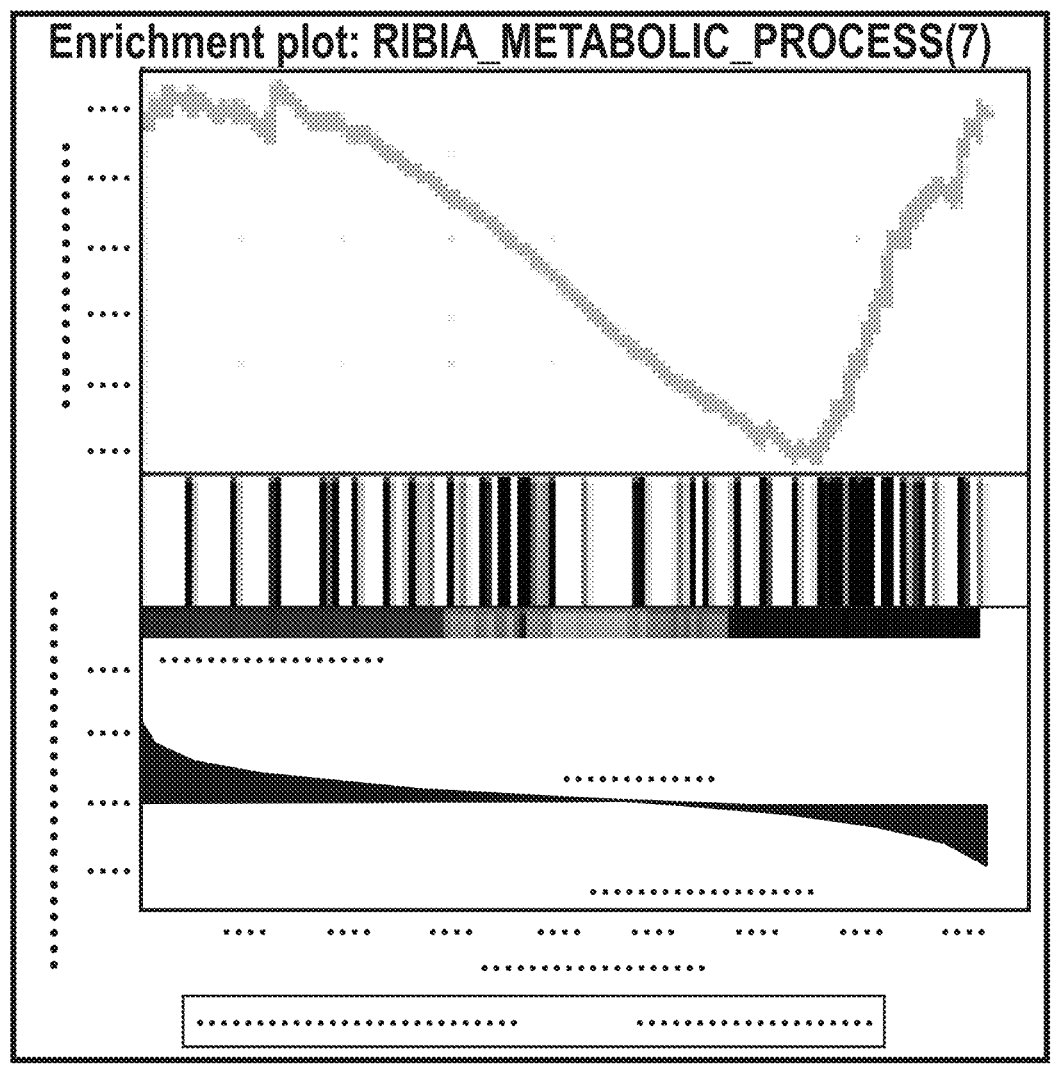
Figure 12D:
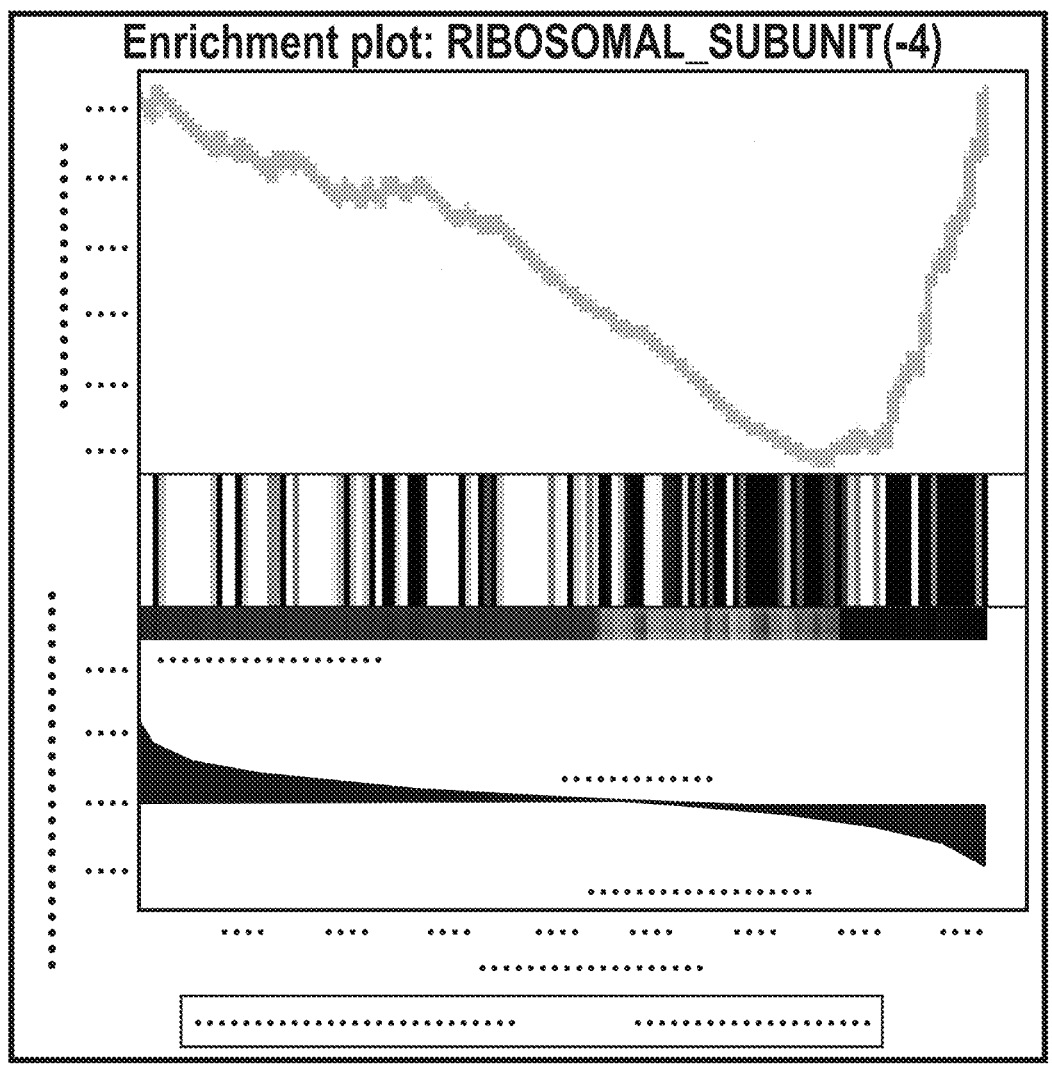
Figure 12E:
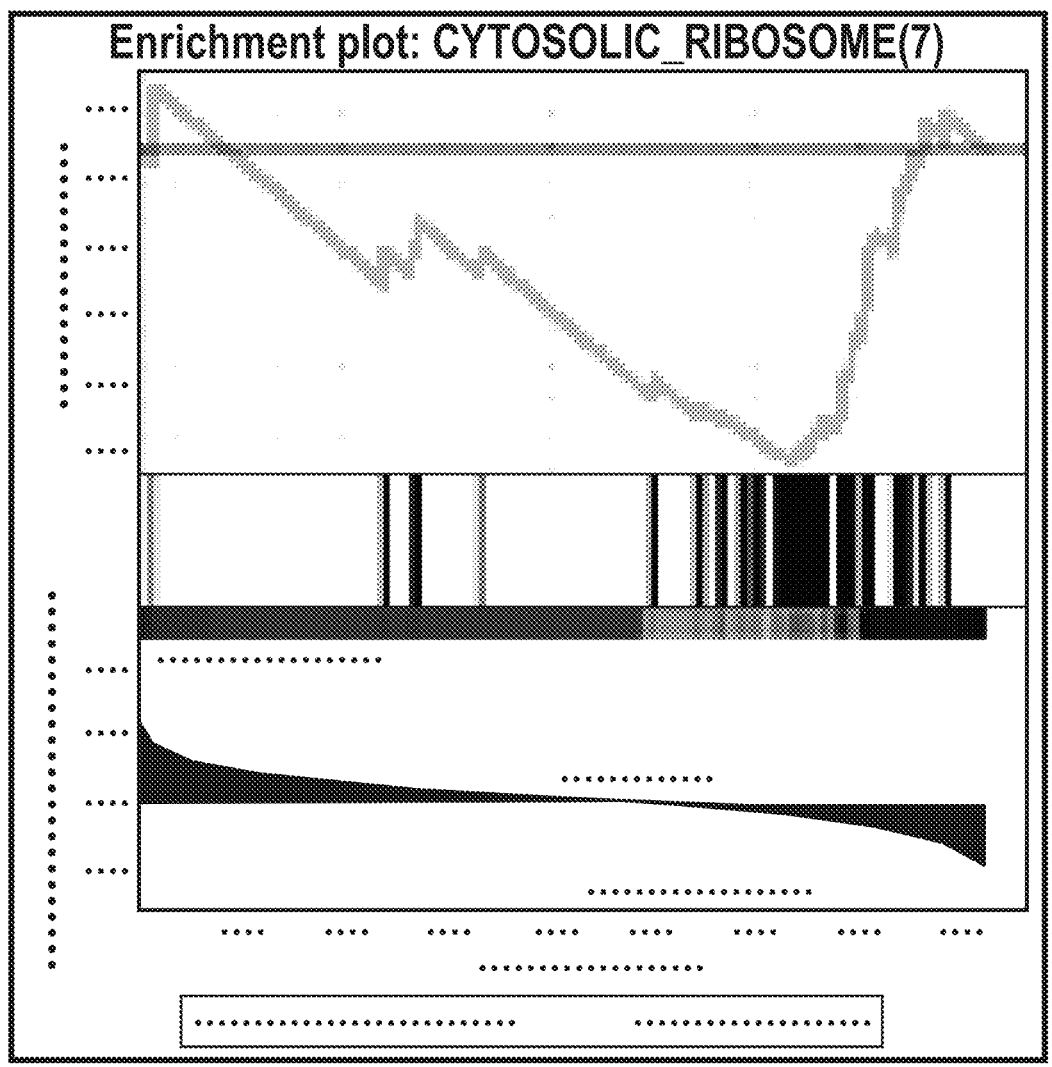
Figure 12F:
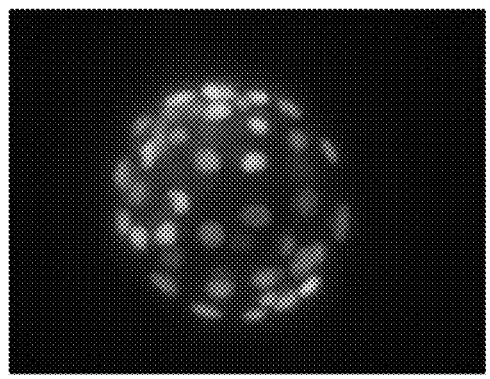
Figure 12G:
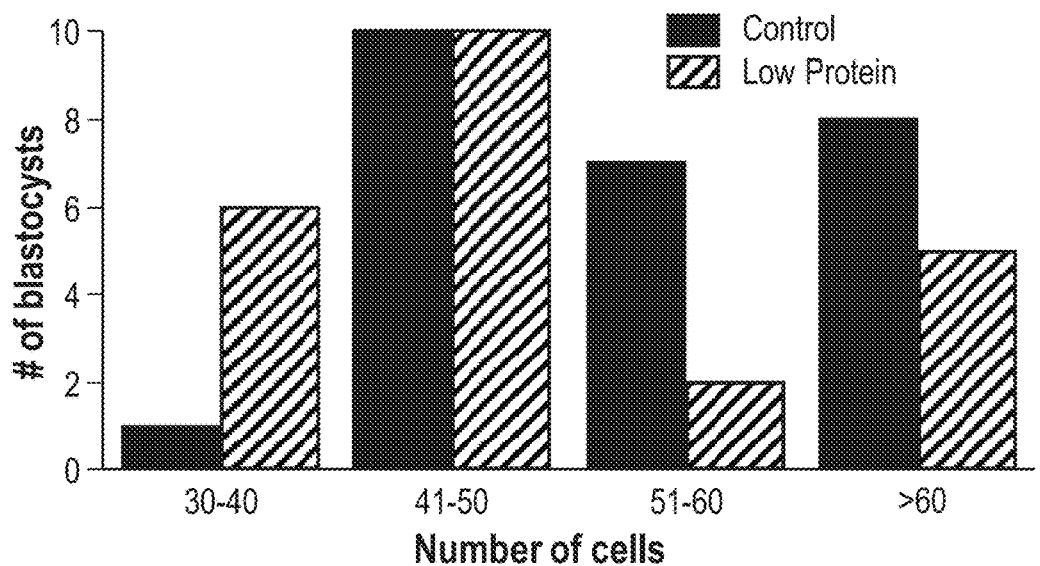
Figure 12H:
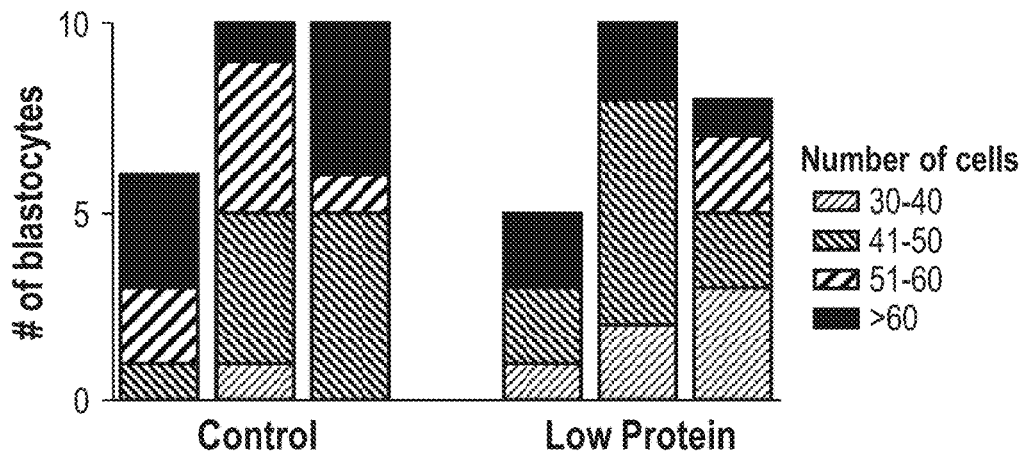

FIGS. 12A-12H show paternal dietary effects on preimplantation development. FIG. 12A shows subjected cumulative distribution plot for all genes encoding ribosomal protein genes. X axis shows the relative expression of these genes in Low Protein IVF embryos, compared to Control. Grey line shows distribution of dietary effects on all non-RPG genes, for all four stages. Left shift at the 2-cell stage shows downregulation of RPGs in Low Protein 2-cell embryos. FIGS. 12B-E show GSEA plots for various sets of genes involved in ribosome biogenesis at the indicated developmental stages. FIG. 12F shows an example image of a blastocyst stained with DAPI and anti-Cdx2 to image total cell number and trophectoderm cells. FIG. 12G shows that Low Protein diet reproducibly alters developmental tempo. FIG. 12H shows aggregated data for three replicate experiments, showing the number of blastocysts with the indicated number of cells, for embryos generated via IVF using Control or Low Protein sperm, as indicated.

Example 15—Dietary Effects on tRNAs in Testes

Figure 13A:
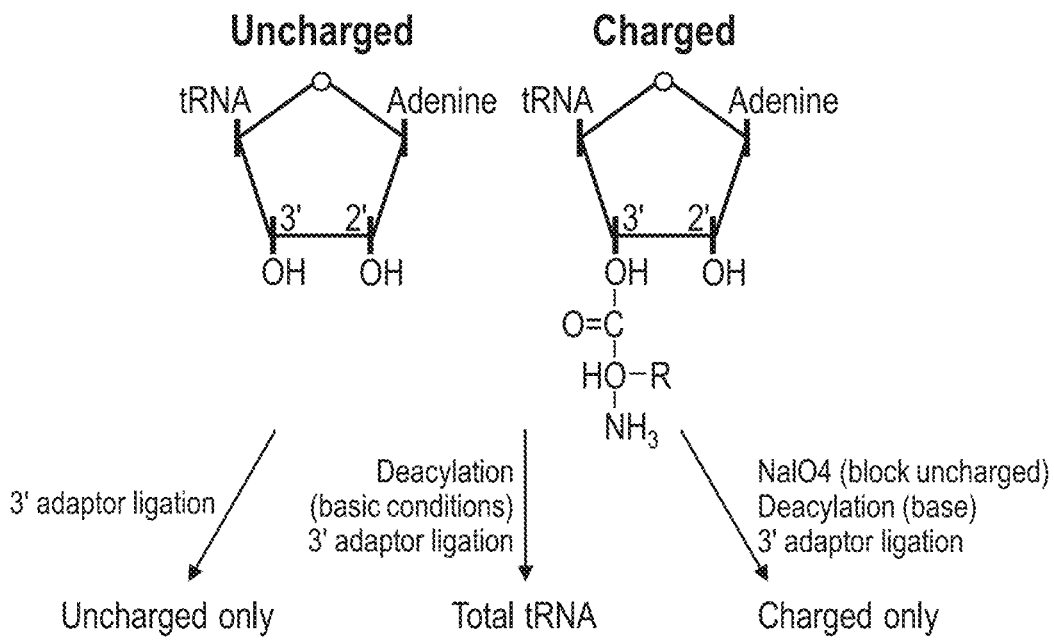
FIGS. 13A-13H show dietary effects on tRNAs in testes.
Figure 13B:
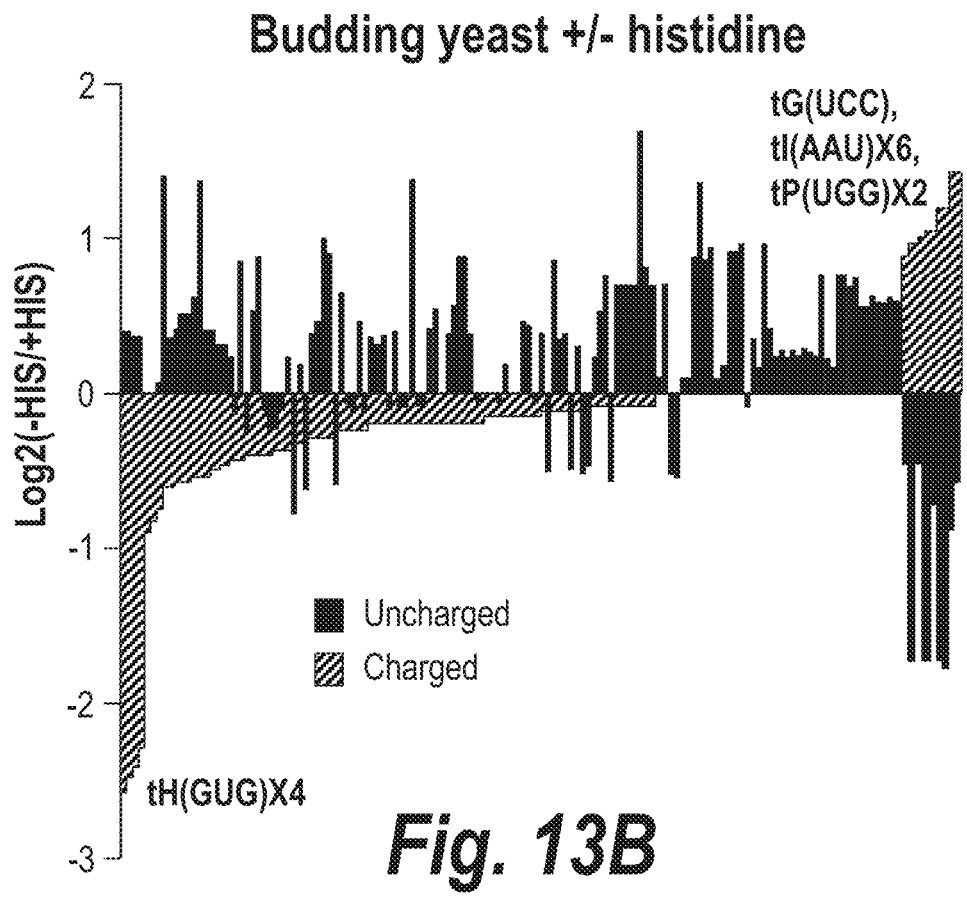
Figure 13C:
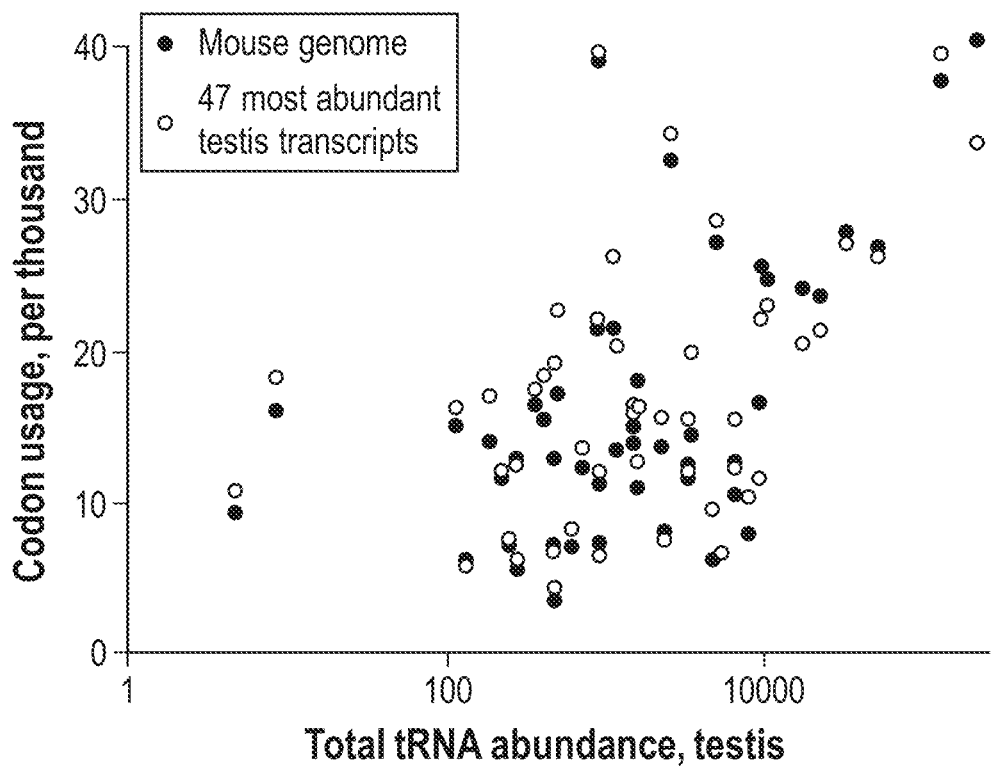
Figure 13D:
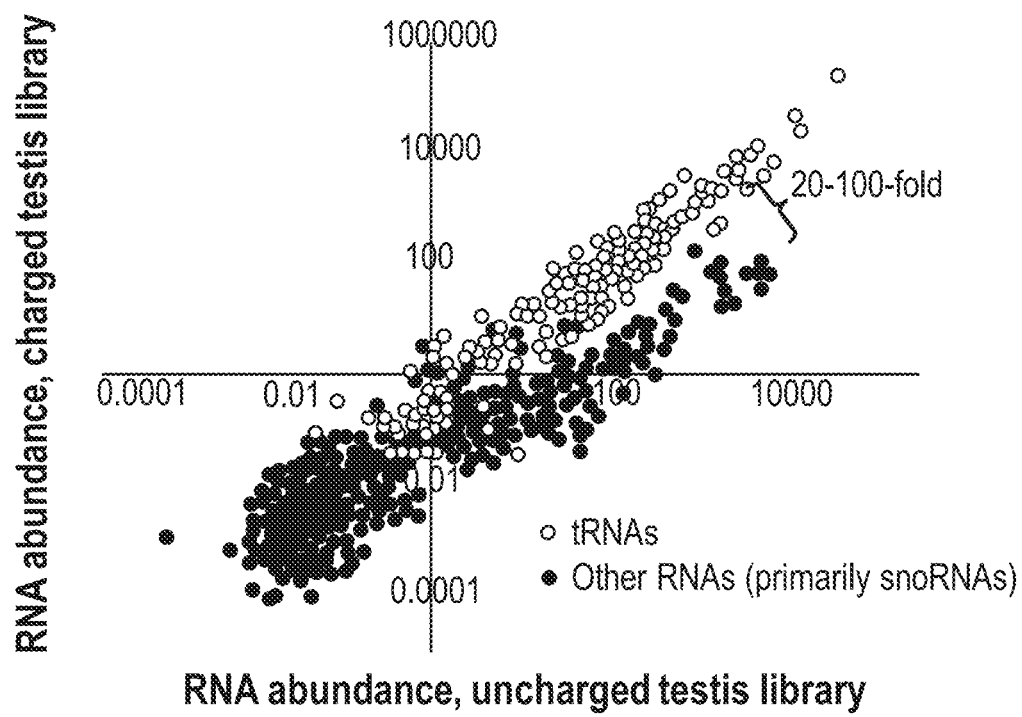
Figure 13E:
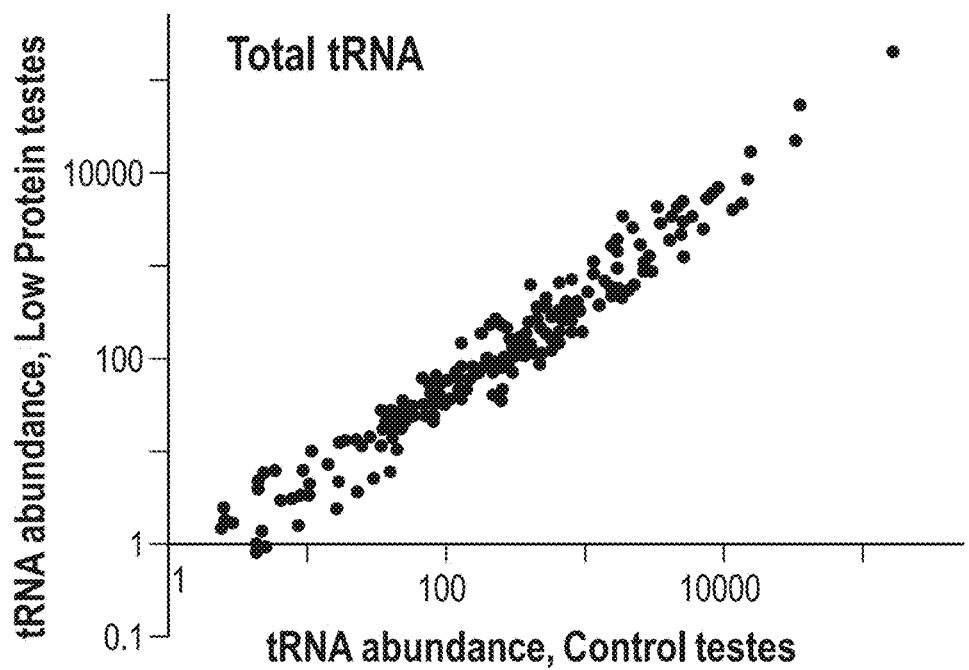
Figure 13F:
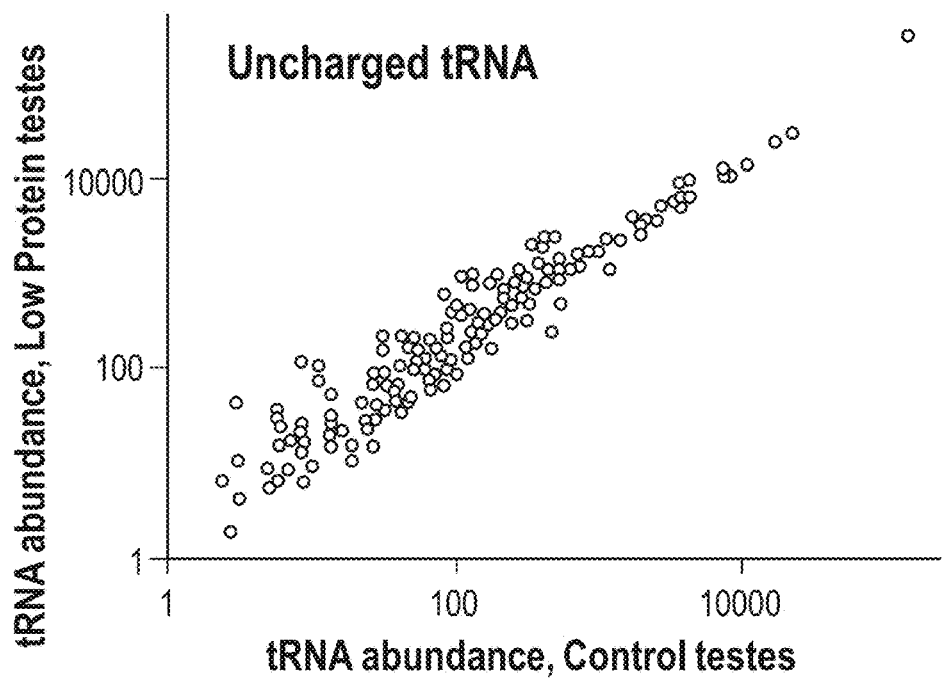
Figure 13G:
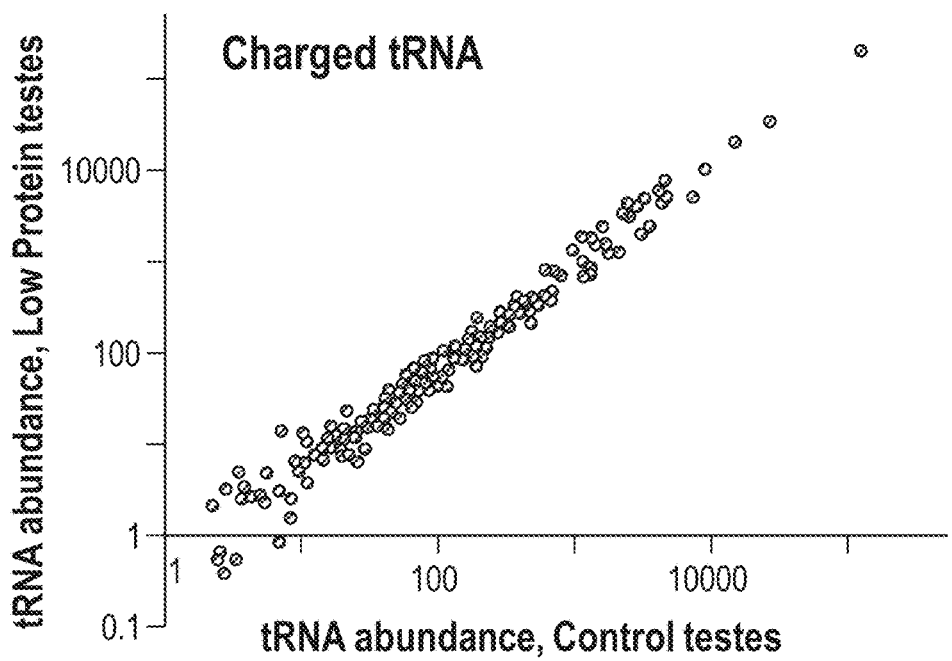
Figure 13H:
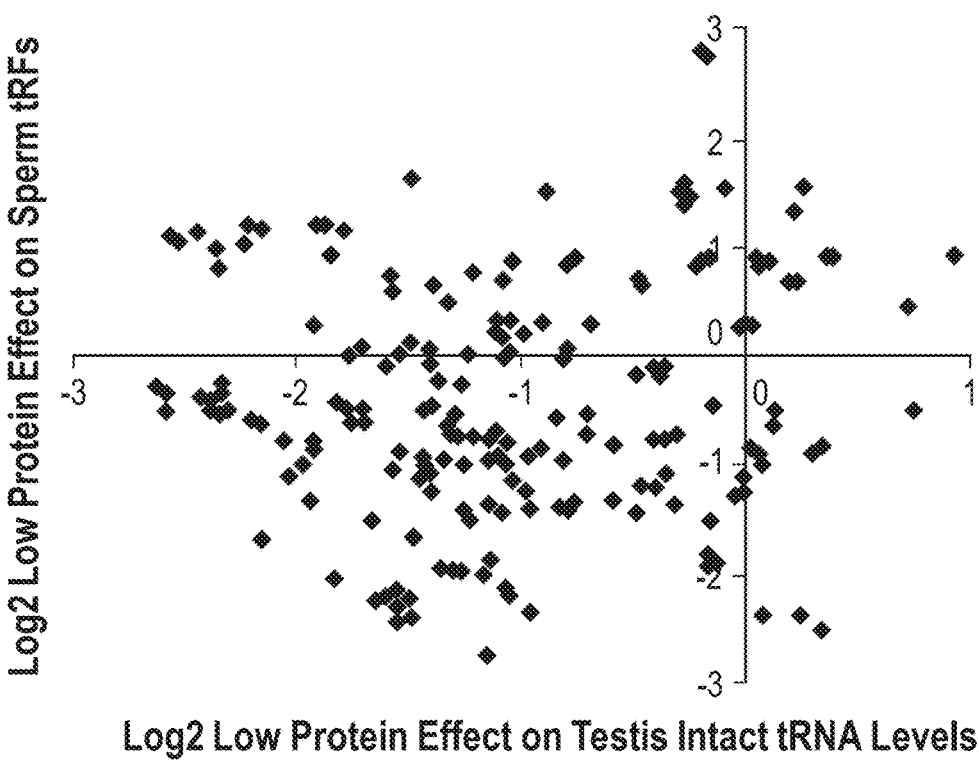

This example shows that when the levels of intact tRNAs are assayed in the testis, there is no correlation between dietary effects on testicular tRNA levels and tRF changes in cauda sperm. The data are shown in FIG. 13. FIG. 13A shows a schematic illustrating assay for tRNA charging analysis. RNA purified from a given tissue was isolated under acidic conditions to preserve charged tRNAs, and subjected to the three treatments shown to enable deep sequencing characterization of charged, uncharged, and total tRNA levels. FIG. 13B shows validation of tRNA charging protocol. Budding yeast grown in the presence (+HIS) or absence (–HIS) of histidine were subjected to the tRNA analysis shown in FIG. 13A. Changes in tRNA abundance for charged and uncharged tRNAs are shown on the y axis, sorted by the change in charged tRNA abundance. As expected, charged tRNA-His levels dropped dramatically after two hours of histidine starvation, while levels of uncharged tRNA-His increased. FIG. 13C shows testicular tRNA abundance correlation with codon bias in the mouse. The x axis shows intact tRNA abundance in testis (total tRNA is shown here but similar results hold for uncharged or charged tRNA datasets) in log scale, and the y axis shows the corresponding codon abundance (in codon frequency/1000) in all murine mRNAs, or in the 47 most-highly expressed mRNAs in testis. Data for testis mRNA abundance is from Carone et al. (Carone, B R, et al. 2010. Cell 143: 1084-1096). FIG. 13D shows validation of tRNA charging analysis. Scatterplot shows abundance of approximately 60-80 nt RNAs in the total RNA protocol (x axis, log scale) compared to abundance of RNAs in the charged tRNA protocol (y axis, log scale). While tRNA levels are broadly consistent between the two protocols (charged/uncharged ratios vary up to approximately 10-fold between individual tRNAs), other RNAs captured in the total RNA protocol, mostly snoRNAs (some of which are of similar size to tRNAs), are approximately 20-100 fold less abundant in the charged tRNA library. FIGS. 13E-G show Low Protein vs. Control effects on tRNA levels for total (FIG. 13E), uncharged (FIG. 13F), and charged (FIG. 13G) tRNA levels in testis. FIG. 13H shows that dietary effects on sperm tRFs are not explained by effects on intact tRNA abundance in testes. Log ratio between Control and Low Protein males is shown for total tRNA levels in testis (x axis) compared to tRNA fragment levels in cauda sperm (y axis).

Figure 14A:
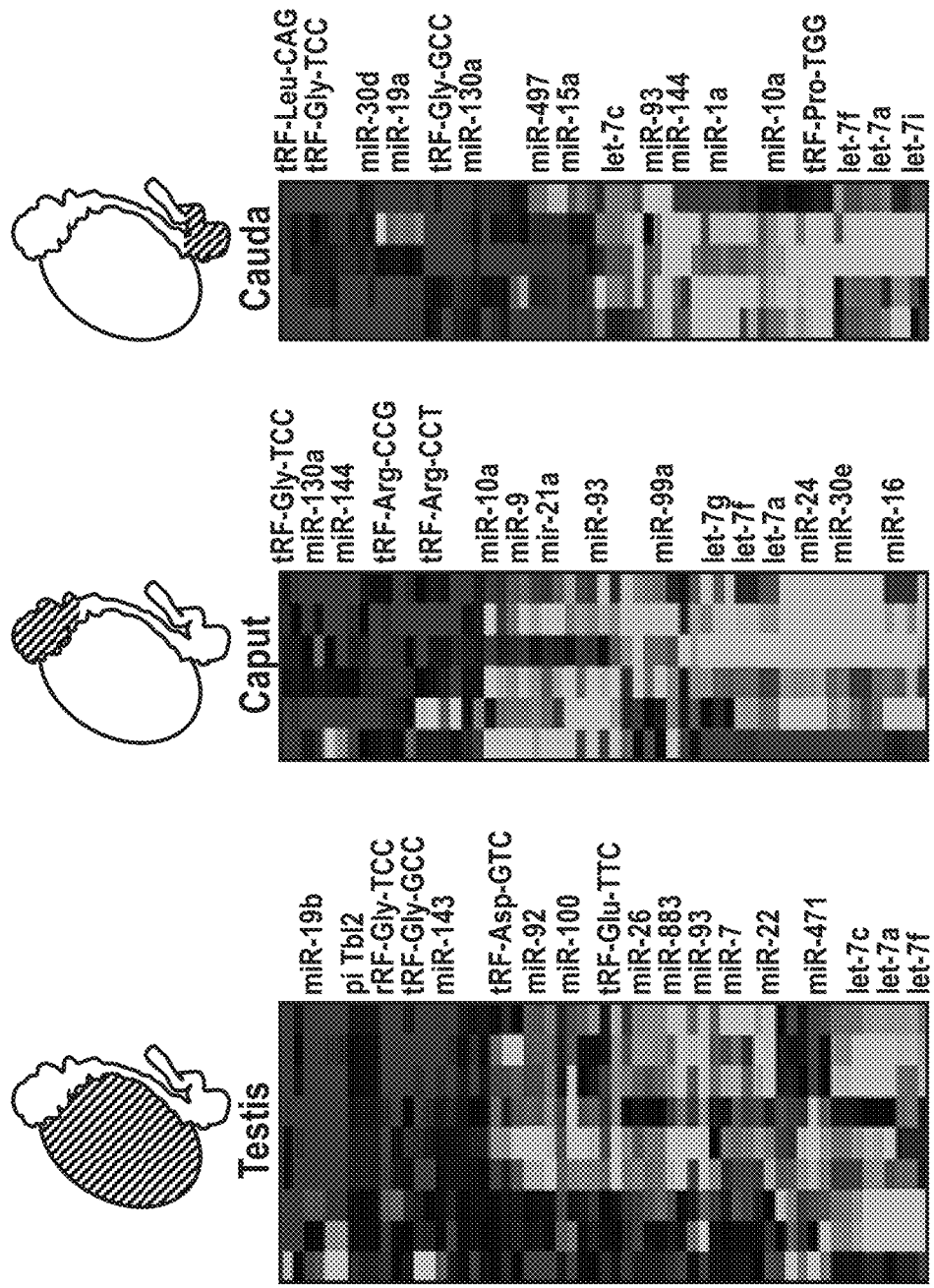
FIGS. 14A and 14B show that there are consistent dietary effects throughout the reproductive tract.
Figure 14B:
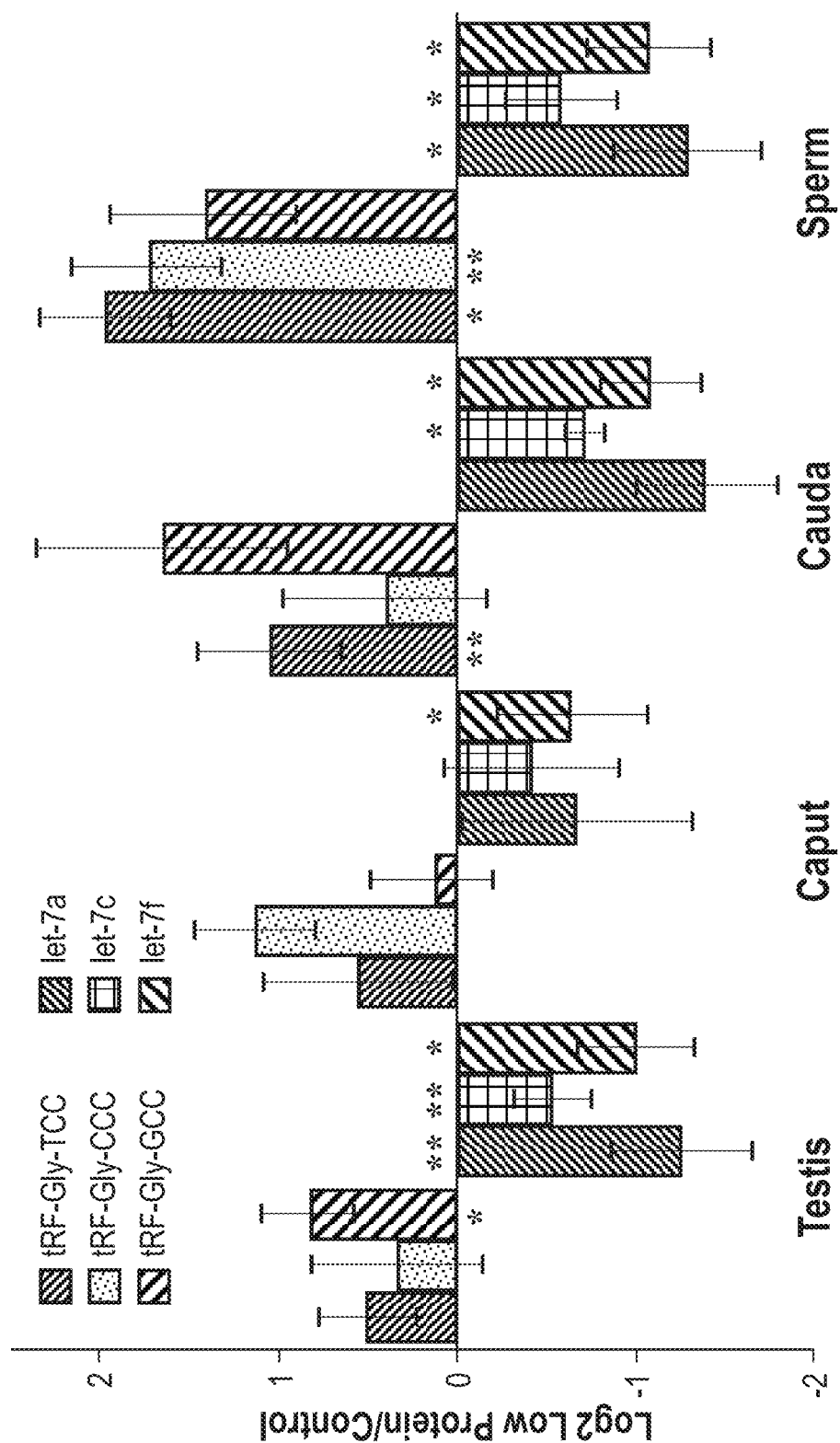

Example 16—Consistent Dietary Effects are Observed Throughout the Reproductive Tract This example shows that there are consistent dietary effects throughout the reproductive tract. The data are presented in FIG. 14. FIG. 14A shows the dietary effects on small RNA abundance in testes and caput and cauda epididymis samples. Each heatmap shows log 2 of Low Protein/Control RNA abundance for a pair of samples, showing RNAs (rows) that exhibit consistent dietary effects across >75% of samples. FIG. 14B shows the coherent dietary effects on tRF-Gly and let-7 family members throughout the male reproductive tract. For each RNA, bars show average and standard error of the mean for Low Protein effects on the abundance of the RNA species in the indicated tissue. Changes with a nominal p value of <0.05 (paired t test, not corrected for multiple testing) are indicated with asterisks.

Example 17 RNA Populations in Caput Sperm

Figure 15A:
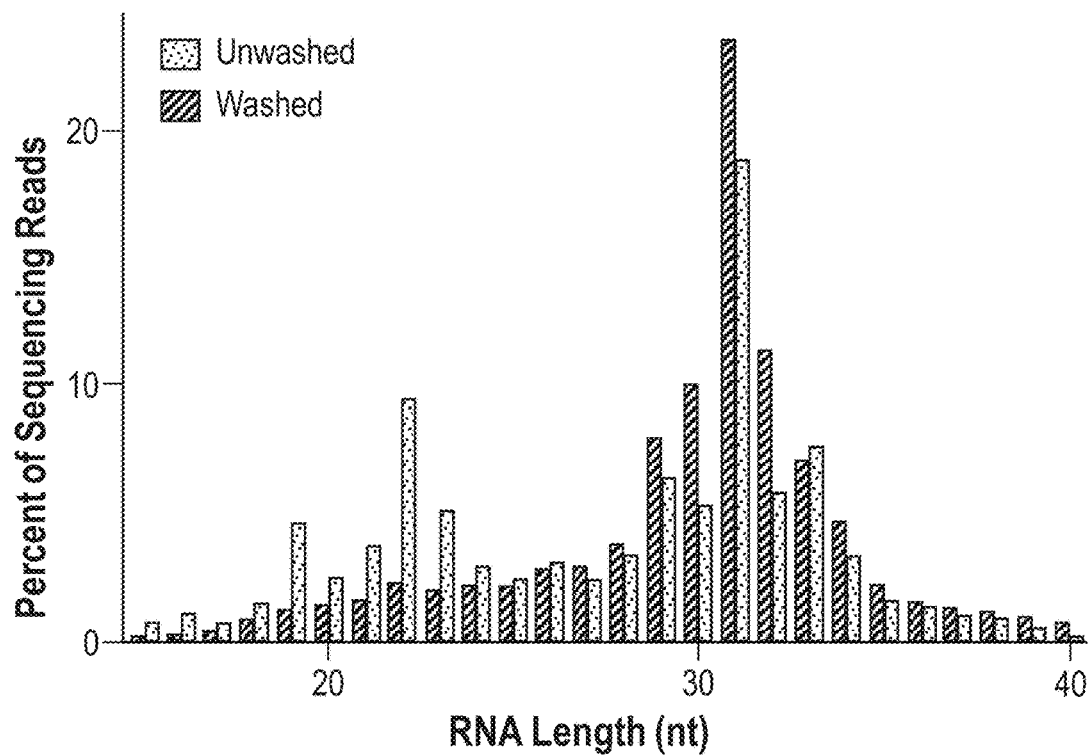
FIGS. 15A-15F show RNA populations in caput sperm.
Figure 15B:
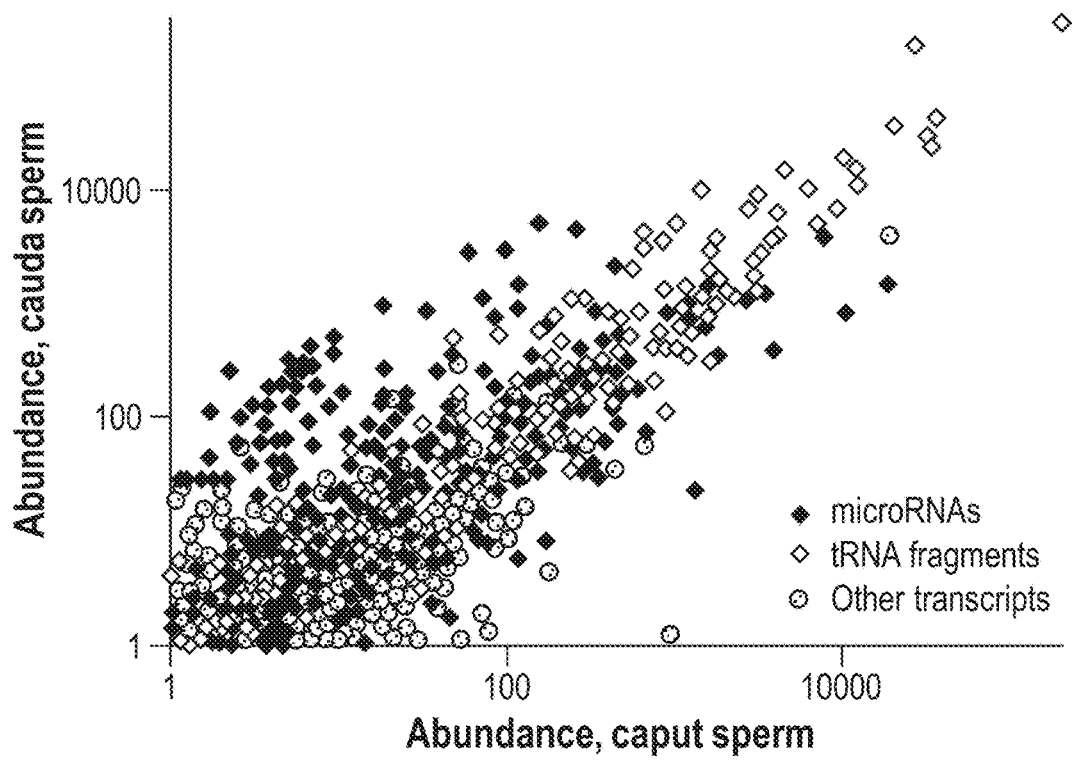
Figure 15C:
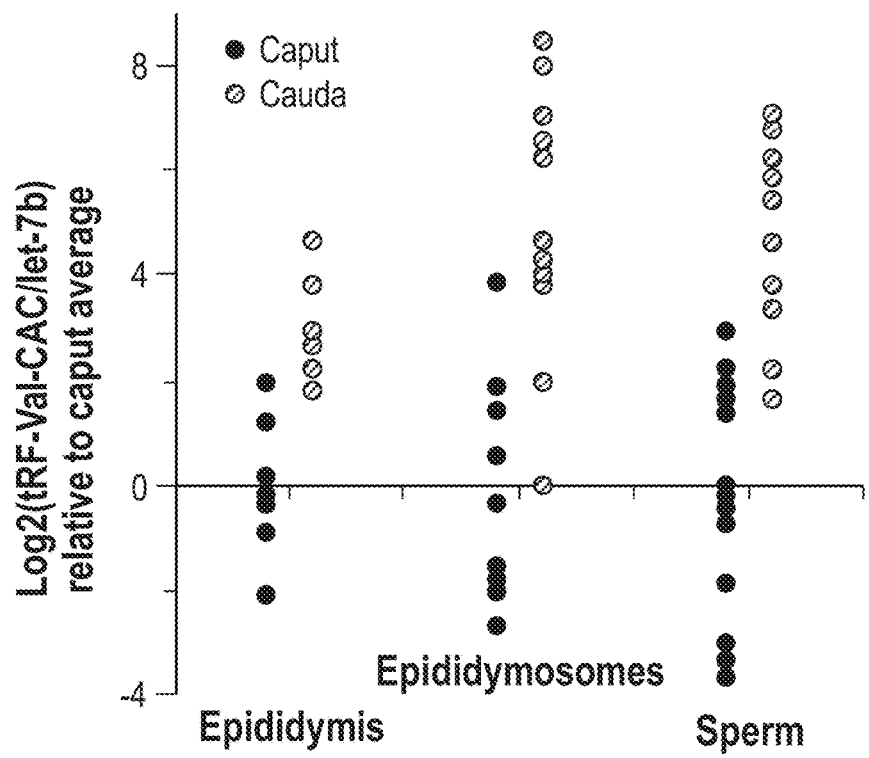
Figure 15D:
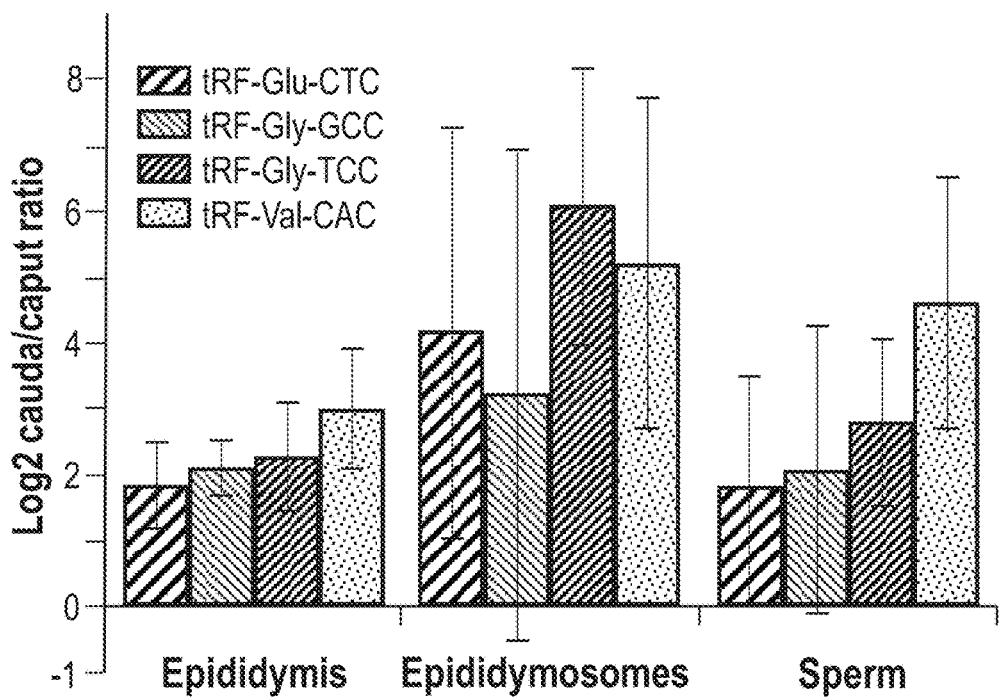
Figure 15E:
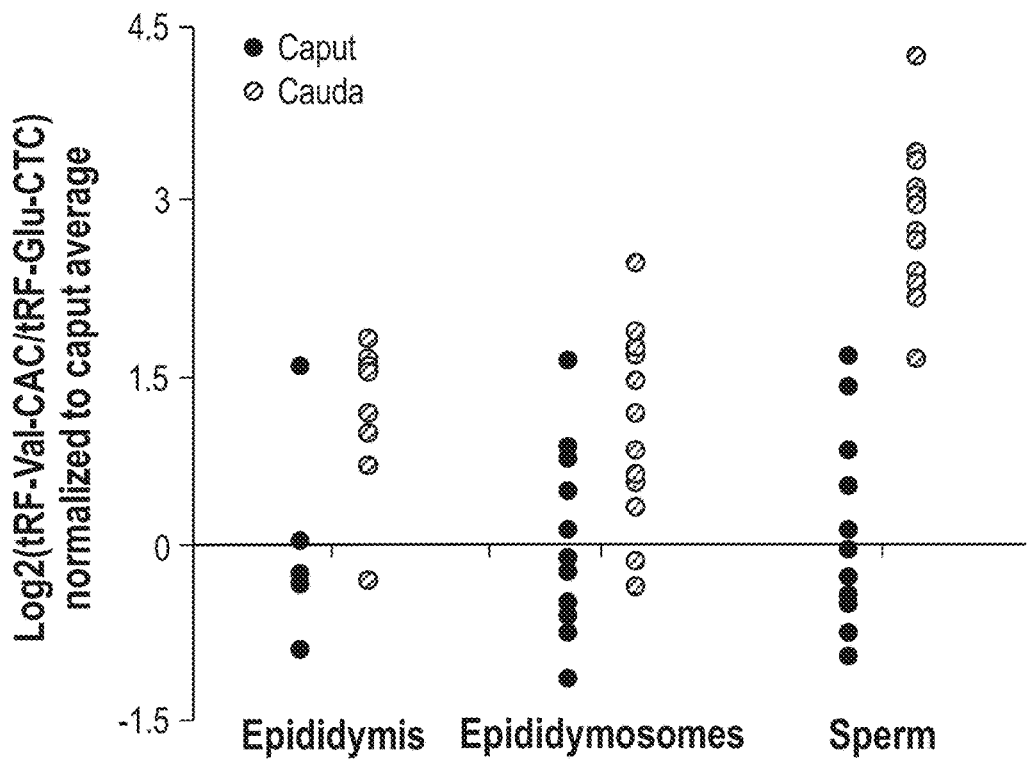
Figure 15F:
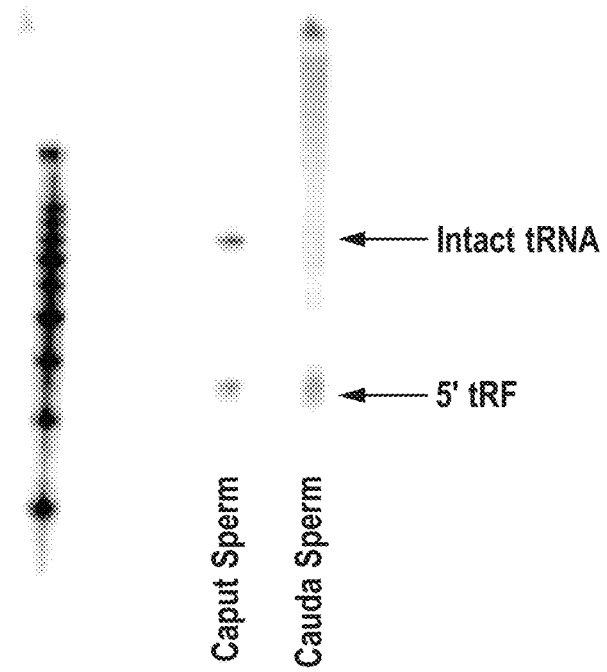

In this example, the RNA populations in caput sperm are detailed, showing that the RNA payload of caput sperm differs substantially from that of cauda sperm. The data are shown in FIG. 15. FIG. 15A shows that unwashed caput sperm are contaminated with RNAs abundant in caput epididymosomes. Caput sperm were isolated with and without washing with an epithelial cell lysis buffer. RNA isolated from unwashed caput sperm included numerous microRNAs that were most abundant in caput epididymosomes. FIG. 15B shows a comparison of small RNA payloads of cauda vs. caput sperm for all RNA species with an abundance of at least 1 ppm in both sperm populations. These changes in RNA abundance could result from extant RNAs from caput sperm being degraded during further transit through the epididymis, or from small RNAs being gained via processing or trafficking during post-testicular maturation. FIG. 15C shows the proximal-distal biases observed for epididymis (x axis) were recapitulated in cauda vs. caput sperm samples (y axis). For clarity only RNAs are shown with at least 50 ppm abundance in at least one of the four sample types (cauda or caput, sperm or epididymis) are shown. The correlation coefficient for each RNA class is shown adjacent to its label. FIG. 15D shows that there is a gain in all four tRFs from caput to cauda. Data for the four tRFs indicated was normalized to let-7b, and here the average cauda/caput difference for each tissue is shown plus/minus the standard deviation. Similar results were obtained using miR-21 as a normalized control. In addition, nearly-identical results were obtained using Taqman assays for the 23, 27, or 29 nt variants of tRF-Gly-GCC (only data for 27 nt is shown). These data are consistent either with a general gain of tRFs from caput to cauda samples of all three tissue types—epididymis, epididymosomes, and sperm—or loss of let-7 or miR-21. FIG. 15E shows that tRF-Val-CAC is strongly cauda-enriched. Data from FIG. 15D are shown with tRF-Val-CAC normalized to tRF-Glu-CTC rather than to microRNAs. Northern blots performed against the 5'end of tRNA-Gly-GCC for samples of bull caput sperm and bull cauda sperm, show that caput sperm carry intact tRNAs (FIG. 15F).

Example 18—Dietary Information is Carried in Sperm

This example shows that metabolic gene expression is altered in offspring generated via in vitro fertilization (IVF) using sperm obtained from animals consuming a control or low-protein diet. Despite the potential for IVF and embryo culture to obscure paternal effects on offspring metabolism, it was found that, compared with control IVF offspring, IVF-derived offspring of males consuming a low-protein diet exhibited significant hepatic up-regulation of the gene encoding the cholesterol biosynthesis enzyme squalene epoxidase (Sqle). These results are shown in FIG. 16.

Figure 16A:
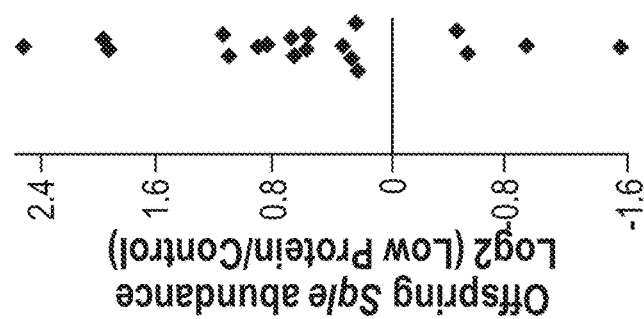
FIGS. 16A-16C show that dietary information is carried in sperm.
Figure 16B:
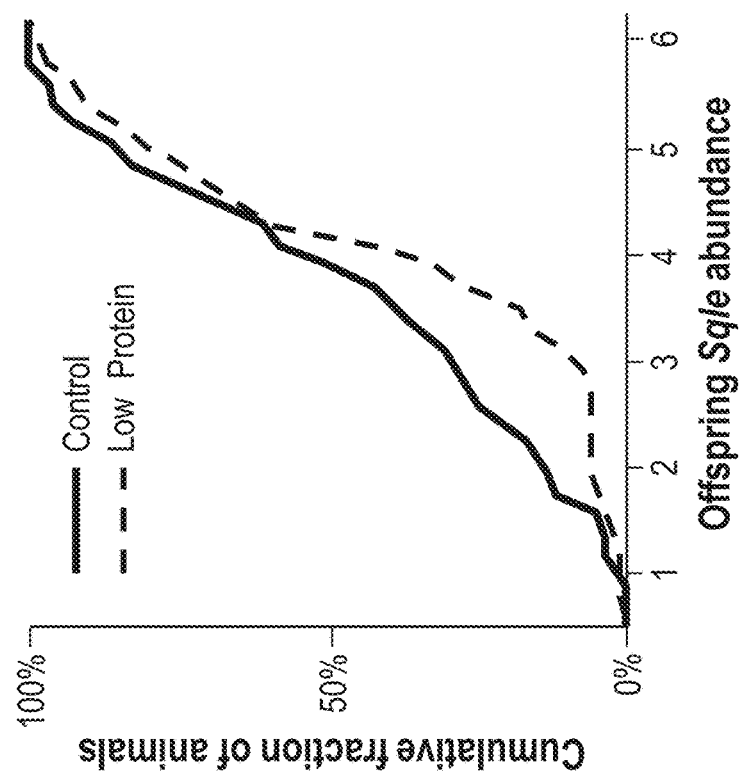
Figure 16C:
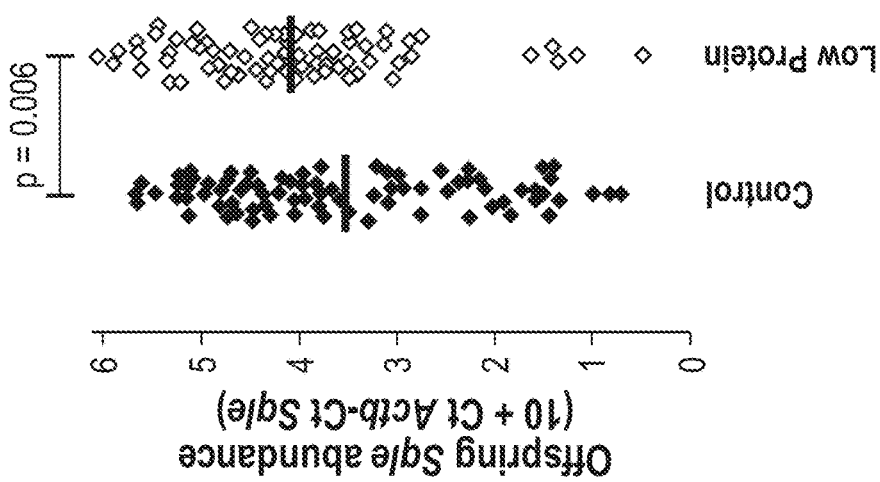

FIGS. 16A-16C show that dietary information is carried in sperm. FIG. 16A shows the sperm from males consuming Control or Low Protein diet which were used to fertilize oocytes gathered from Control females. Two-cell stage embryos were then implanted into pseudopregnant females and allowed to develop to birth. At 3 weeks of age, offspring were sacrificed (n=92 for Control, n=86 for Low Protein), and livers were harvested for analysis of Sqle, a gene previously shown to be upregulated in offspring of Low Protein males relative to Control males Carone et al., Cell 2010; 143: 1084-1096). Sqle levels (normalized to Actb) are shown for all offspring as individual points, with horizontal lines showing mean expression. FIG. 12B shows the cumulative distribution of Sqle expression for all offspring generated using Control or Low Protein sperm, as indicated.

FIG. 16C shows consistent litter effects. Here, Sqle levels were averaged for all offspring of a given litter. As sperm samples were always obtained from male siblings split to different diets, litter pairs resulting from paired fathers were compared, with each dot representing the ratio of Sqle expression between appropriately paired litters.

Example 19—Mechanistic Basis for tRF-Gly-GCC Regulation of MERVL Targets

Figure 17A:
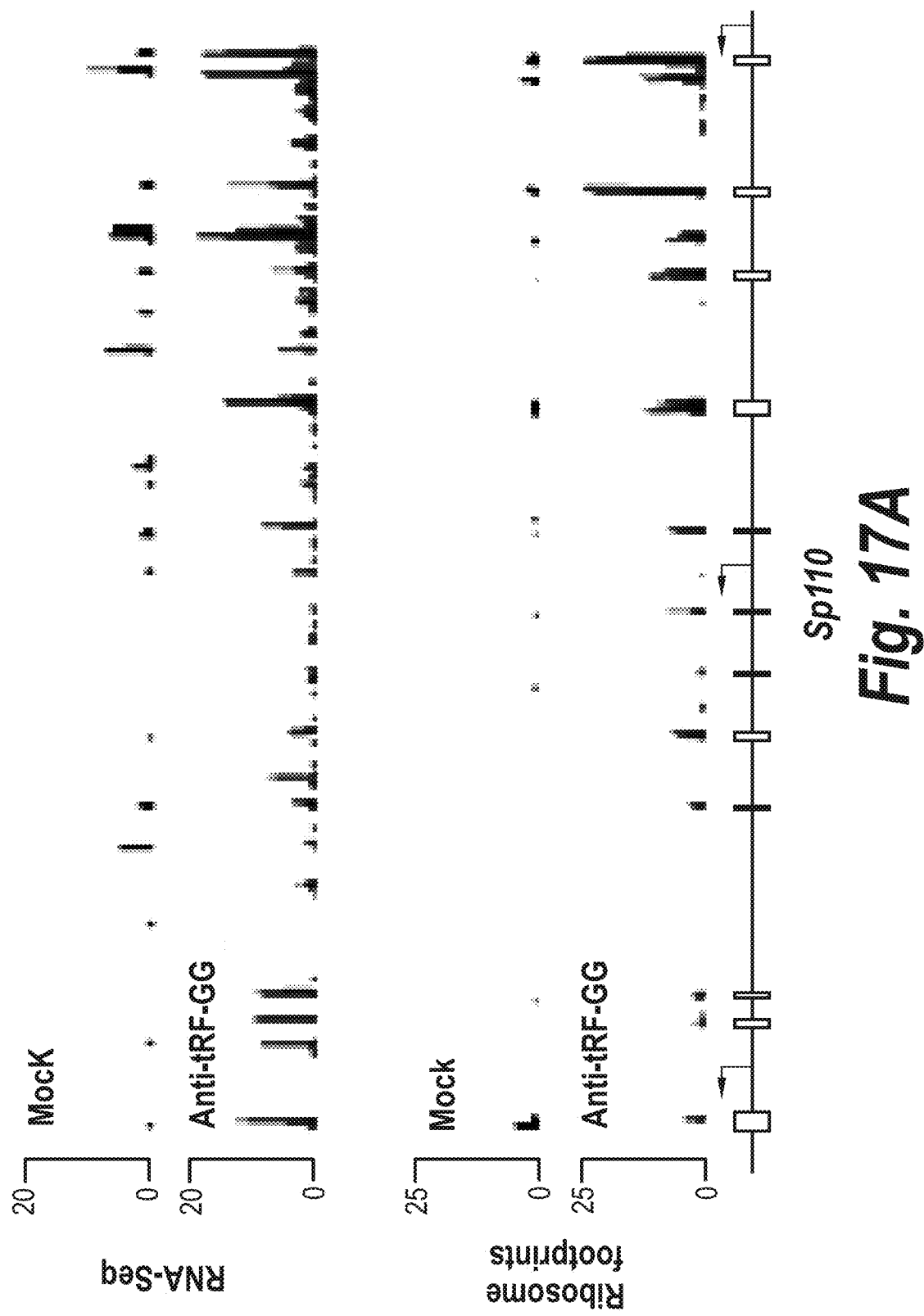
FIGS. 17A and 17B show the mechanistic basis for tRF-Gly-GCC regulation of MERVL.
Figure 17B:
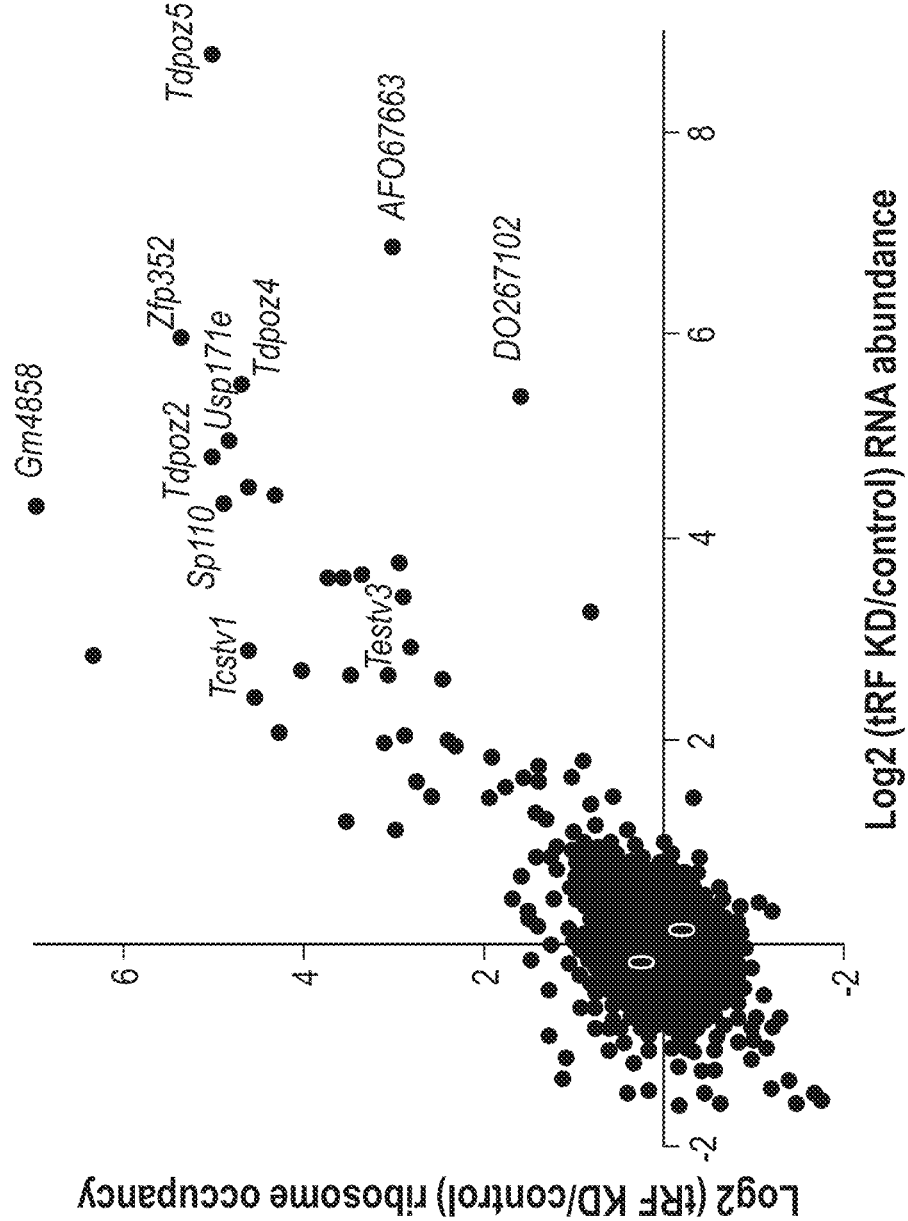

This example provides data supporting the mechanistic basis for tRF-Gly-GCC regulation of MERVL targets. The data are shown in FIG. 17. FIGS. 17A-B show the mechanistic basis for tRF-Gly-GCC regulation of MERVL. FIG. 17A shows RNA-Seq and ribosome footprinting data for Sp110. Genome browser view shows aggregated data for four independent replicate ES cell transfections with shRNAs targeting GFP, and an antisense oligo targeting tRF-Gly-GCC. FIG. 17B shows that RNA abundance and ribosome footprinting data are highly correlated. Scatterplot shows the effect of tRF-Gly-GCC inhibition, expressed as the log 2 of the median of the four LNA transfections divided by the median of the eight control replicates (four mock, four GFP KD). Genes exhibiting a 2-fold difference between GFP KD and mock, and genes with maximum abundance of <2 FPKM in any individual replicate, were excluded from this scatterplot.

Example 20—Observations from Examples 1-19

Figure 3B:
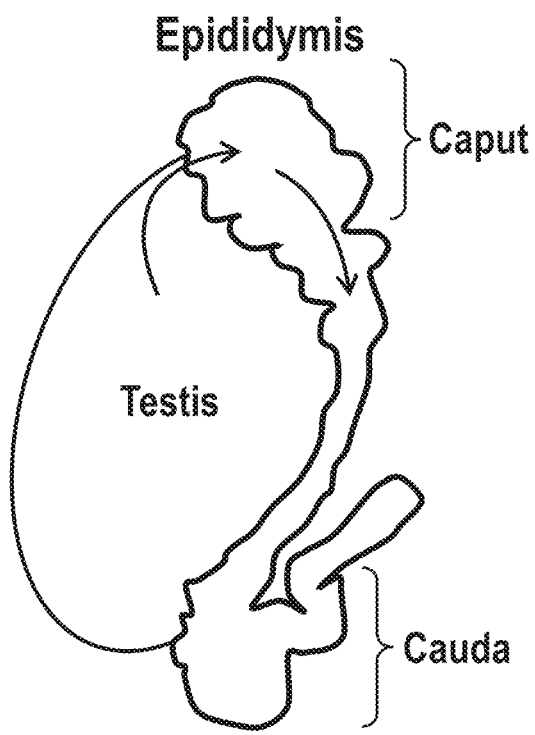

The results from the previous examples show (1) that effects of paternal diet on offspring are mediated via information found in sperm (FIG. 15), (2) that diet alters the level of small RNAs, including specific tRNA fragments, throughout the male reproductive tract and in mature sperm (FIGS. 1 and 7), and (3) that tRNA fragments can regulate expression of transcripts driven by endogenous retroelements (FIGS. 8-9). The data also uncover the temporal dynamics of small RNA biogenesis during post-testicular maturation (FIGS. 2-4), and strongly suggest a role for epididymosomes in transmitting small RNAs from somatic cells of the epididymis to maturing gametes.

A Role for Epididymosomes in Small RNA Trafficking to Sperm

Perhaps the most surprising hypothesis raised from the results of these Examples is that epididymosomes deliver a payload of small RNAs to maturing sperm. The idea that epididymal cells are partly responsible for the RNA payload of sperm is compelling given the increasing number of organisms in which gametogenesis involves a key role for small RNA communication between germ cells and somatic support cells (Bourc'his, D and O Voinnet. 2010. Science, 330: 617-622). Four observations support the hypothesis. First, extremely low levels of tRNA fragments were found in the murine testis, instead observing increasingly abundant tRFs throughout the epididymis. Moreover, during epididymal transit, levels of a number of tRFs increase in sperm between the proximal and distal segments. Second, the small RNA payload of purified epididymosomes is a remarkable match for the small RNAs found in cauda sperm. In the very unlikely case that sperm tRNA fragments do not originate in the epididymis, this observation would then either be an astonishing coincidence if epididymosomal RNAs serve no regulatory function, or more likely would hint at potential regulatory roles of epididymosomal RNAs in lumicrine signaling or signaling to the female reproductive tract (Bromfield, J J, et al. 2014. Proc. Natl. Acad. Sci. USA, 111: 2200-2205; Vojtech, L, et al. 2014. Nucleic Acids Res., 42: 7290-7304). Third, fusion of purified epididymosomes with caput sperm in vitro delivers tRNA fragments to the resulting "reconstituted" sperm, demonstrating that the epididymosomes bearing tRFs either can fuse with caput sperm or very stably adhere to sperm. Finally, although the major small RNAs (glycine tRFs and let-7) that respond to diet in mature sperm are also diet-regulated in the testis (as well as the epididymis), other diet-responsive small RNAs in sperm only exhibit dietary responses in epididymis but not in testis.

Dietary Effects on Small RNAs in Mammalian Sperm

The key changes in small RNA observed in sperm of animals raised on Low Protein diet are observed throughout the male reproductive tract. Generally, at least five levels at which diet could exert effects on the levels of a given tRF in sperm can be identified, by influencing: (1) intact tRNA abundance, either via transcription or stability, (2) tRNA cleavage, regulated potentially by tRNA charging status or by dietary signaling to tRNA-modifying enzymes such as Dnmt2 or Nsun2, (3) tRF stability, (4) tRF sorting into epididymosomes, or (5) sperm fusion with epididymosomes—this category includes dietary regulation of fusion-related cell surface proteins, but also mechanisms involving changes in sperm maturation time or epididymis luminal flow rate that could affect how long sperm spend in different parts of the epididymis. At present, dietary effects on tRF processing, stability, or trafficking appear to be the most likely scenario for at least a subset of diet-regulated tRFs.

tRF Regulation of an Endogenous Retroelement

Figure 8B:
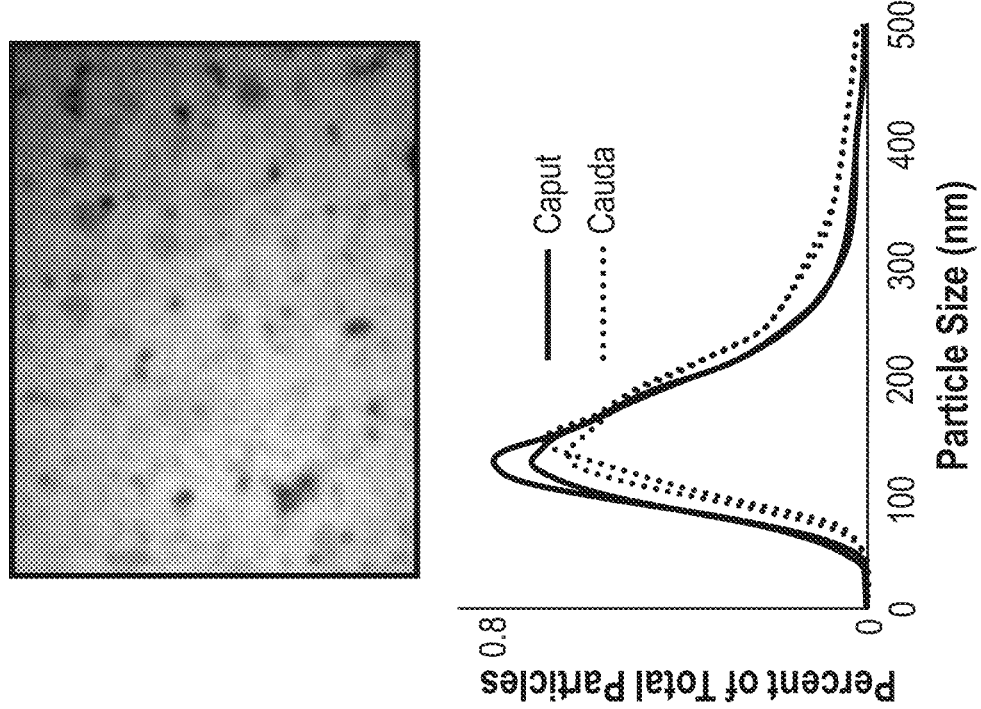
FIGS. 8A-8E show the characterization of caput epididymosome preparations.
Figure 8A:
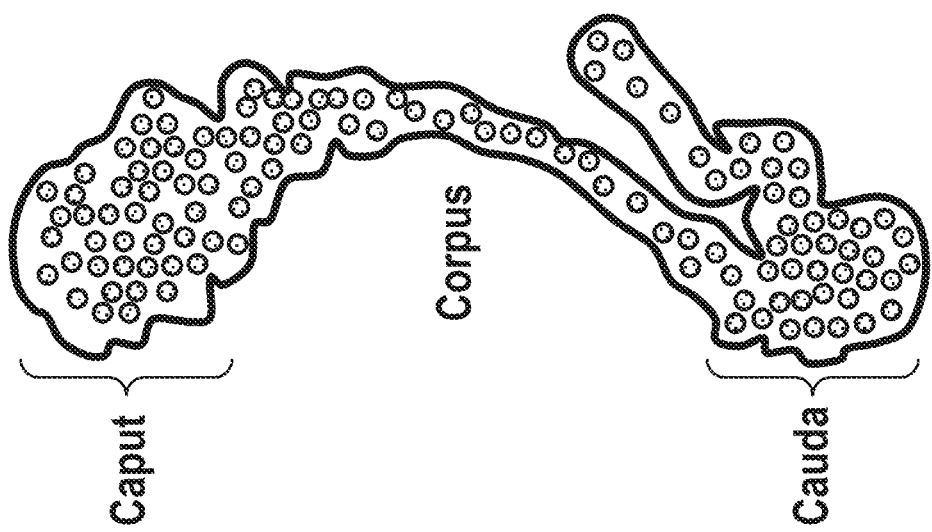
Figure 8C:
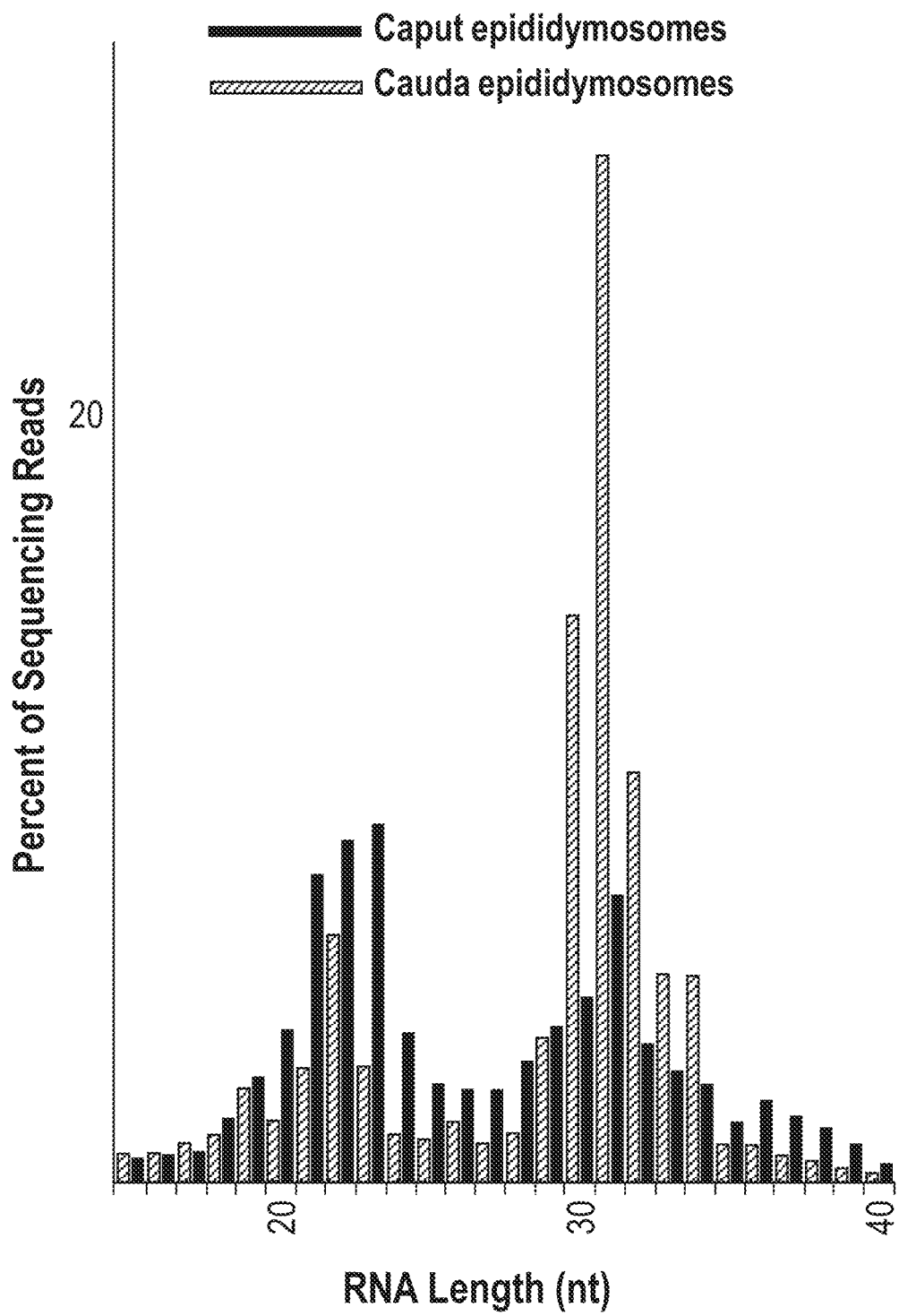
Figure 8D:
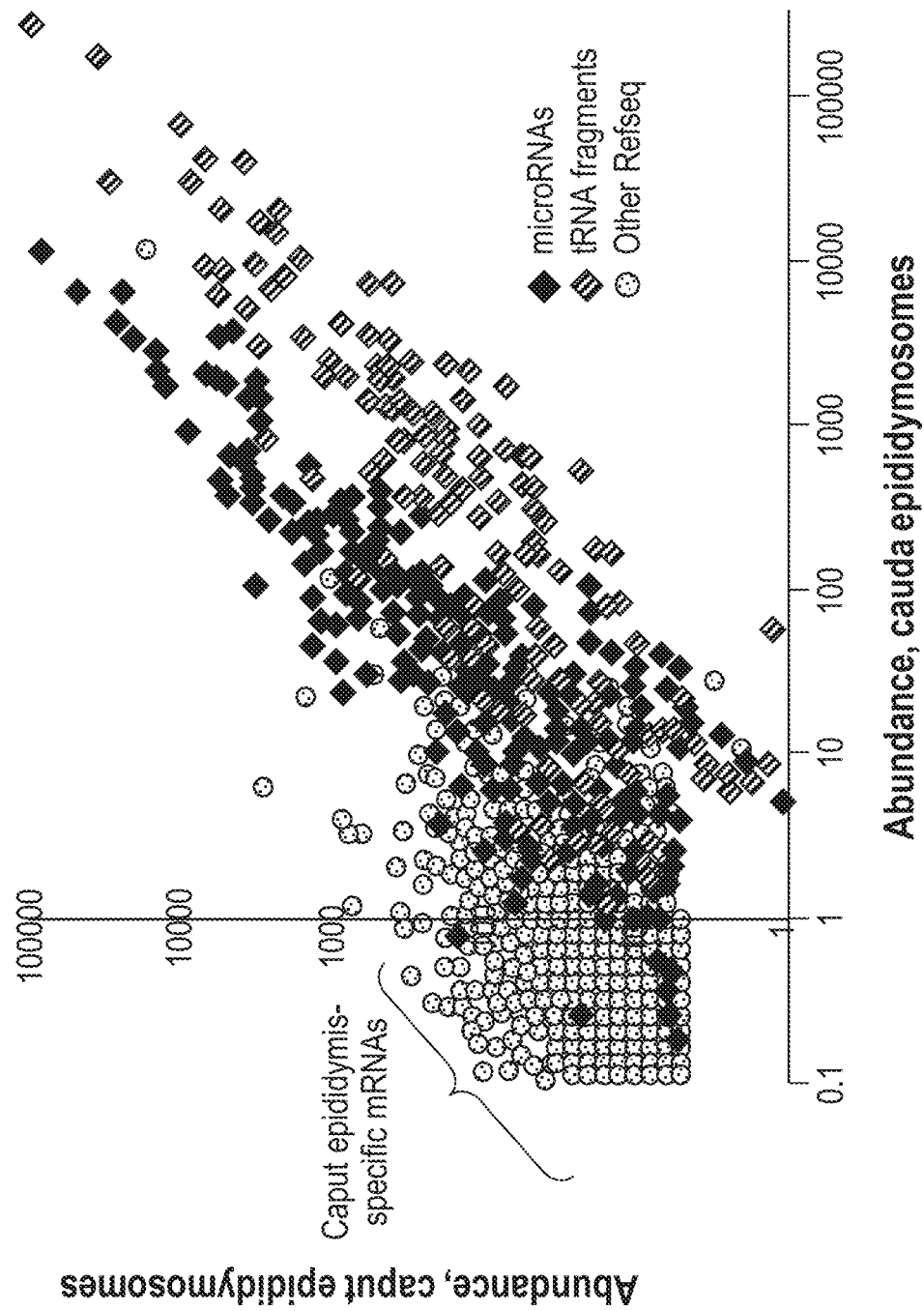
Figure 8E:
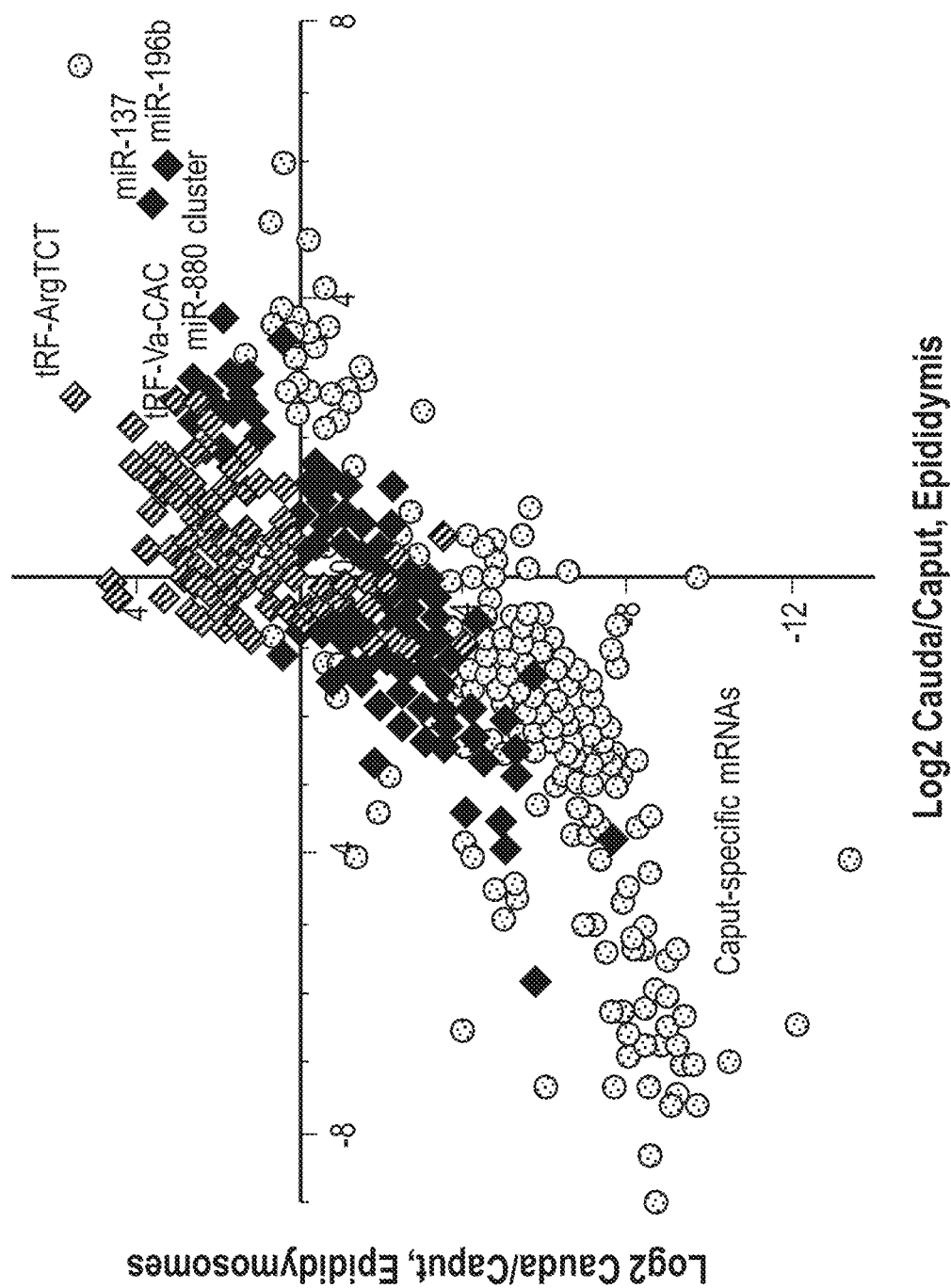

How might diet-regulated small RNAs in sperm have the ability to impact the phenotype of offspring? tRF-Gly-GCC was the focus of these studies thanks to its readily apparent role in altering mRNA abundance in ES cells—other abundant tRFs such as tRF-Gly-TCC may play roles in regulation of genes not expressed in ES cells, or may exert regulatory effects that are not apparent in mRNA abundance measures (e.g., on translation), and it will be interesting to determine whether these other abundant tRFs in sperm have effects on preimplantation development. tRF-Gly-GCC is extremely unlikely to be uniquely responsible for the effects of paternal Low Protein diet on offspring cholesterol metabolism, as let-7 and many other small RNAs change abundance in Low Protein sperm, and many more genes (such as RPGs) change in preimplantation embryos fertilized using these sperm than just MERVL target genes (FIG. 8E). Thus, we feel the likeliest scenario is that paternal dietary effects are analogous to complex disease genetics, with multiple separate factors each contributing a fraction of the quantitative phenotype.

Inhibition of tRF-Gly-GCC, but not related tRFs, results in dramatic derepression in both ES cells and in early embryos of a subset (approximately 50 of approximately 500) of transcripts that are regulated by dispersed LTRs of the endogenous retroelement MERVL (Macfarlan, T S, et al. 2011. Genes Dev., 25: 594-607). Moreover, embryos generated using sperm from Low Protein males reveal significant changes in MERVL target mRNA abundance (FIG. 10), consistent with the idea that tRFs delivered by sperm could affect gene regulation in the early embryo. The mechanistic basis for the observed effects of tRF-Gly-GCC on repression of MERVL LTRs is of interest—although tRNAs nearly universally act as primers for retroelement replication, homology-driven tRF regulation of MERVL is unlikely here as (1) MERVL utilizes tRNA-Leu, not tRNA-Gly, to prime reverse transcriptase, (2) many of the genes in our dataset are associated with isolated LTRs and appear to lack the adjacent tRNA "primer binding sequence", (3) primer binding sequences for ERVs typically have homology to the 3' end of tRNAs, not the 5' end, and (4) transfection of the antisense LNA to tRF-Gly-GCC does not affect levels of tRNA-Leu fragments in ES cells. Shown in these examples is that regulation of MERVL targets is unlikely to be a secondary effect of altered translation of MERVL regulators by tRF-Gly-GCC, while reporter assays show that removing the MERVL LTR from its genomic context—many of the tRF-Gly-GCC targets are found in large chromosomal regions with many MERVL LTRs nearby—does not completely eliminate the ability of the LTR to respond to tRF-Gly-GCC inhibition.

The MERVL regulon provides an intriguing connection to offspring metabolism. MERVL-driven genes are highly expressed in totipotent early embryos (Kigami, D, et al. 2003. Biol. Reprod., 68: 651-654), but a small fraction of otherwise pluripotent embryonic stem cells also express the MERVL program, and MERVL positive cells are functionally totipotent (Macfarlan, T S, et al. 2012. Nature, 487: 57-63). It is well known that alterations in placental function (as induced by uterine artery ligation or caloric restriction) lead to altered cholesterol and glucose metabolism in offspring (Rando, O J and Simmons, R A. 2015. Cell, 161: 93-105). It is hypothesized that tRF-Gly-GCC regulation of the MERVL program could alter the tempo of early development, or alter cell fate allocation in the early embryo. While there was no significant difference in the percentage of Cdx2-positive cells between Control and Low Protein embryos (73+/−5% vs. 71+/−7%), Low Protein embryos consistently exhibited delayed growth relative to Control embryos. Interestingly, altered growth kinetics in early embryogenesis have been shown to occur in response to paternal obesity, which also has been linked to offspring metabolism (McPherson, N O, et al. 2013. PLoS One, 8(8)e71459).

Future studies will shed further light on the role of the epididymis in sensing environmental conditions, on the mechanistic basis for regulation of RNA levels in sperm, and on effects of tRNA fragments on preimplantation development and placentation.

Example 21—Caput Epididymosomes Deliver Small RNAs to Testicular Spermatozoa

The Examples described herein demonstrate that testicular spermatozoa have scarce levels of tRFs, and caput sperm are highly abundant in these small RNAs. Epididymosomes secreted by the epithelium of cauda epididymis have been found to have similar RNA payload as that of the mature sperm and can deliver small RNAs to the relatively "immature" caput sperm (see, e.g., Sharma et al., Science 2016; 351(6271): 391-396).

Figure 18A:
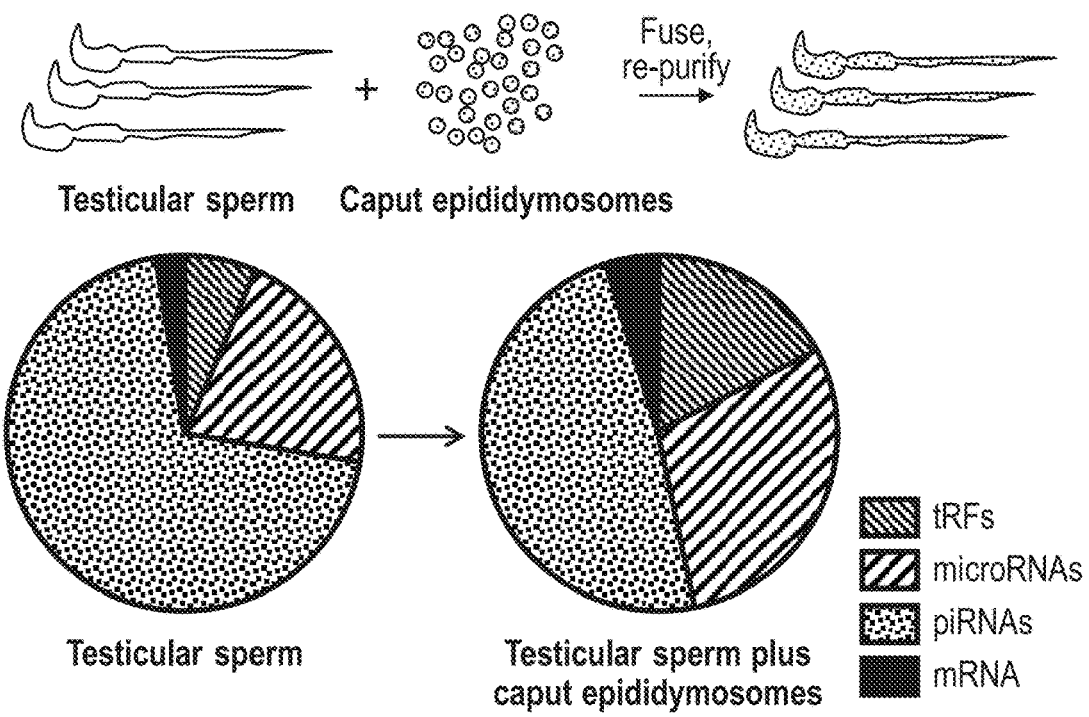
FIGS. 18A-18D show the reconstitution of small RNA delivery to testicular sperm.

To test whether tRFs and other small RNAs are delivered to testicular sperm upon entry into epididymis via fusion with epididymosomes present in the caput epididymis, testicular spermatozoa were reconstituted by fusing them with caput epididymosomes (FIG. 18A). Testicular spermatozoa were incubated with caput epididymosomes for two hours and then purified by multiple washes to isolate "reconstituted" spermatozoa. Next, the levels of specific small RNAs in reconstituted spermatozoa were examined using TaqMan qRT-PCR assays.

Figure 18B:
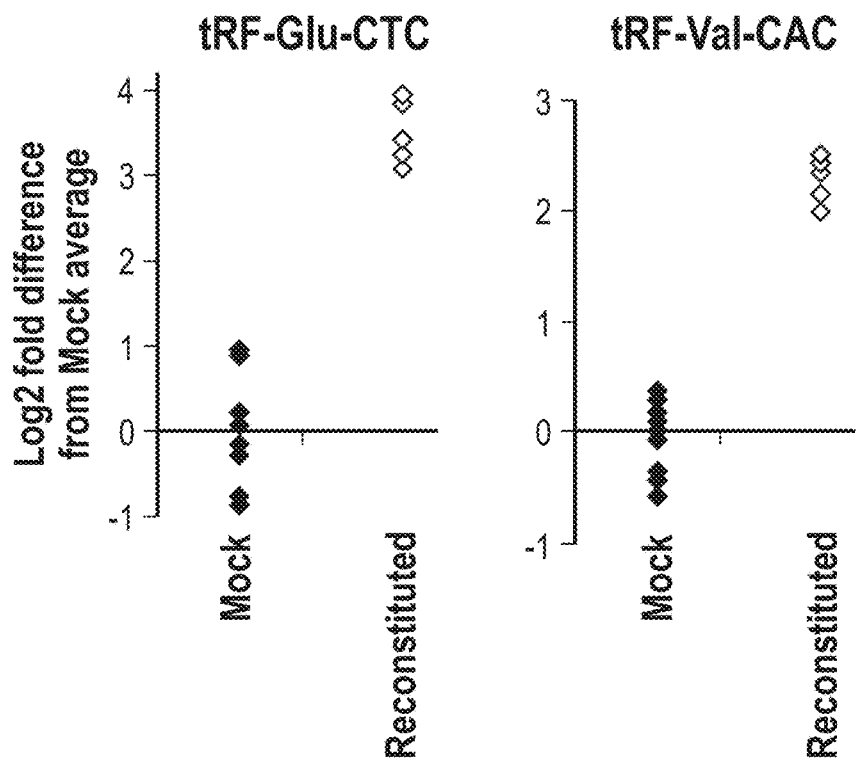
Figure 18C:
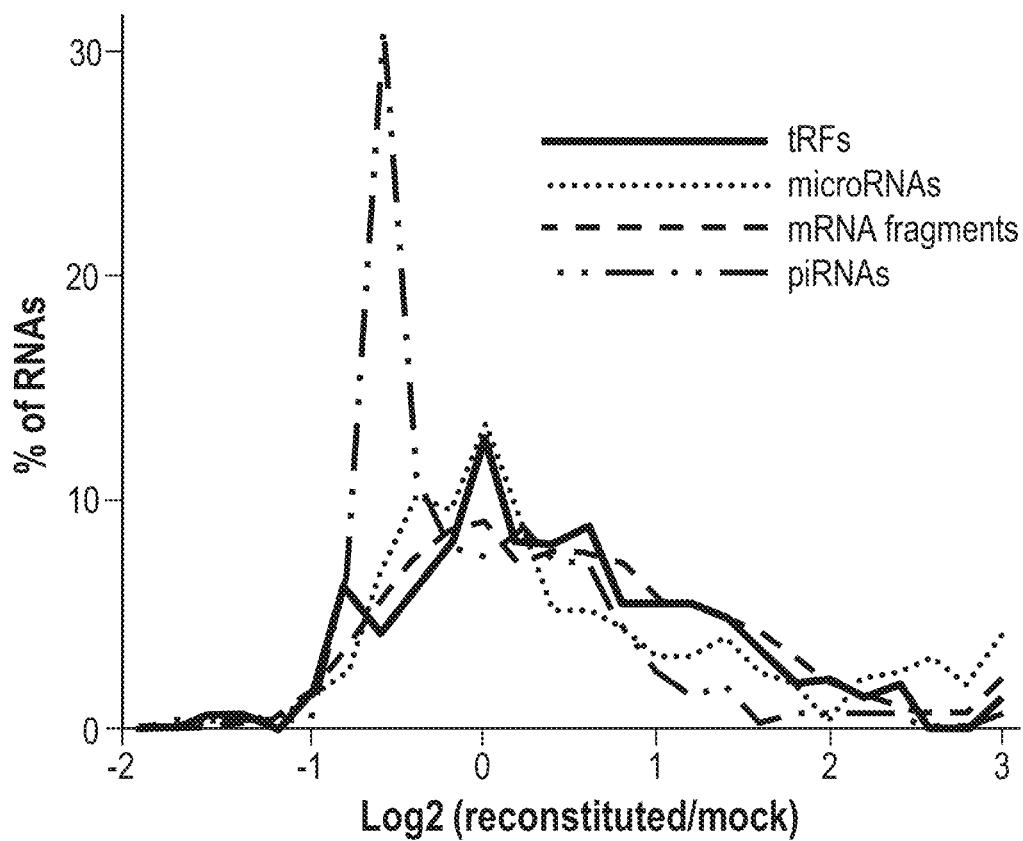
Figure 18D:
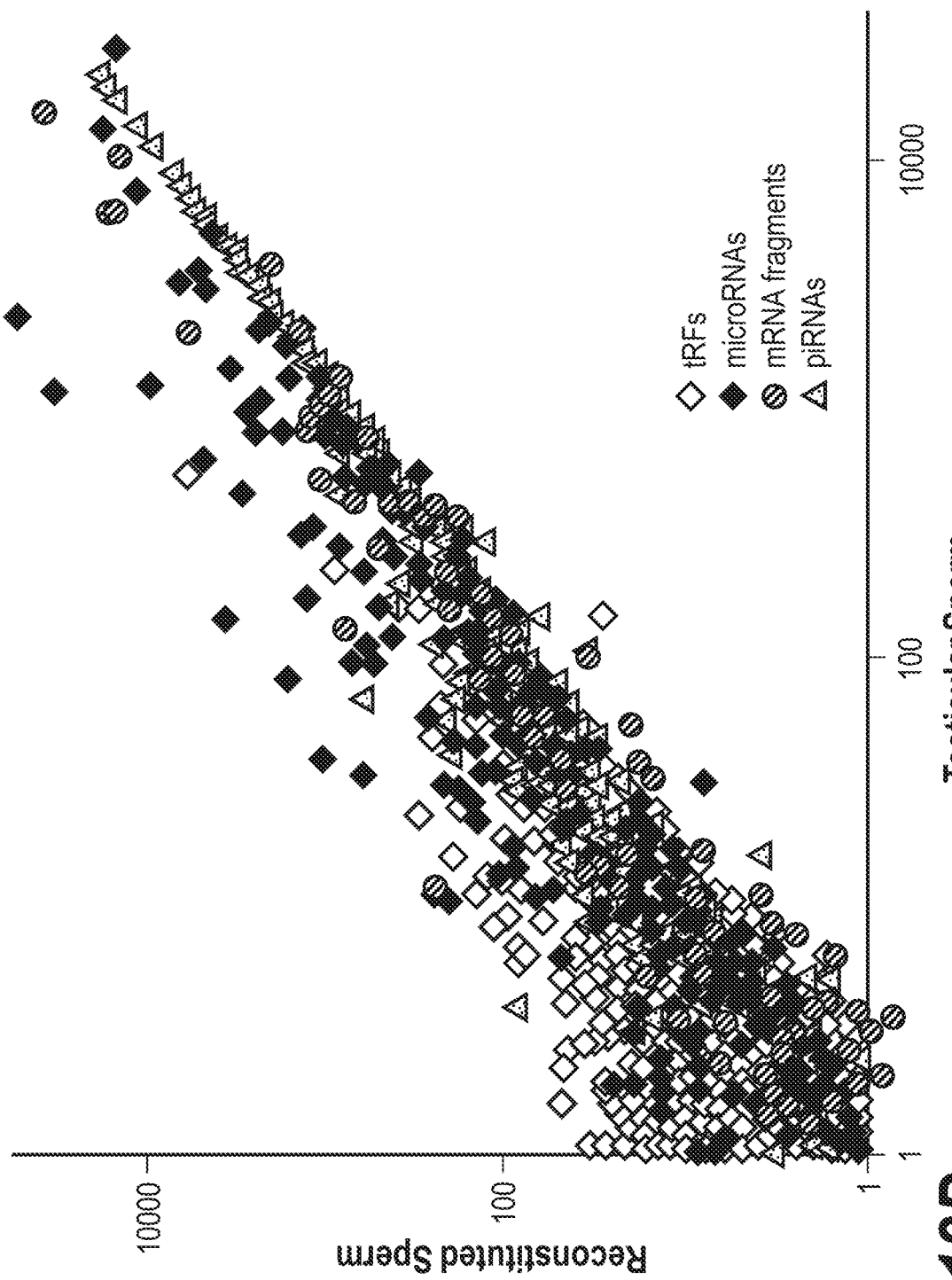

It was determined that tRFs, such as tRF-Glu-CTC and tRF-Val-CAC, which are highly abundant in caput epididymosomes, were up-regulated more than 2-fold in reconstituted spermatozoa compared to the mock fusions (FIG. 18B). Deep sequencing of small RNAs from reconstituted spermatozoa revealed consistent results. Higher levels of tRFs and miRNAs were observed in reconstituted spermatozoa compared to mock controls (FIG. 18A, 18C-18D).

Several lines of evidence prove that the small RNA content of reconstituted sperm is altered due to epididymosome fusion/delivery of small RNAs: 1) as piRNAs are not expressed in epididymis, there are scant levels of piRNAs in epididymosomes (Sharma et al., Science 2016; 351(6271): 391-396), and no change in the levels of piRNAs was detected in reconstituted spermatozoa (piRNAs are all on the diagonal axis of the scatter plot in FIG. 18D); 2) an increase in the levels of small RNA was the primary population of RNA detected, supporting that RNA is delivered to sperm; and 3) reconstituted sperm showed an increase in miRNAs and tRFs that were specifically highly abundant in epididymosomes, such as, e.g., miR-10a/b, miR-148, miR-143, tRF-ValCAC, tRF-GluCTC, tRF-GlyGCC and tRF-His-GTG.

The reconstitution of testicular sperm recapitulated testicular sperm to caput sperm maturation step in vitro. For instance, it was determined that the reconstituted sperm showed 10% higher levels of tRFs compared to testicular spermatozoa (FIG. 18A). In addition, specific small RNA changes were also very well recapitulated. Reconstituted sperm were found to have a higher abundance of caput sperm-enriched microRNAs such as miR-10a/b, miR-143, miR-141, and miR-200a. As such, caput epididymosomes were capable of fusing with mature testicular spermatozoa to deliver their small-RNA cargo. Without intending to be bound by scientific theory, taken together these experiments are most consistent with a mechanism of RNA biogenesis in mammalian sperm in which small RNAs generated in the epididymis are trafficked to sperm in epididymosomes.

Example 22—Analysis of Gene Regulation Effects in Embryos Made Via ICSI Using Caput Sperm, and Cauda Sperm To determine the effects of epididymal maturation on phenotype in the following generation, experiments are carried out in which zygotes are generated via intracytoplasmic sperm injection (ICSI) using sperm obtained from the caput epididymis or from the cauda epididymis. Such zygotes are then allowed to develop into 2-cell embryos, to blastocysts, or are implanted into females and carried to term. Gene regulation is studied in the preimplantation embryos, and metabolic traits are measured in grown offspring, to identify the consequences of using immature sperm to fertilize oocytes.

Example 23—Microinjection of Other Small RNAs into Zygotes; Early Gene Regulation and Metabolic Sequelae Assays To determine the effects of specific small RNAs on phenotype in the following generation, experiments are carried out in which control zygotes are injected with specific small RNAs, such as tRF-Val-CAC, and allowed to develop into 2-cell embryos, to blastocysts, or are implanted into females and carried to term. Gene regulation is studied in the preimplantation embryos, and metabolic traits are measured in grown offspring, to identify the functions of specific small RNAs in early development and future health.

The invention is not to be limited in scope by the specific embodiments and examples described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes. Other embodiments are within the following claims.

We claim:

1. A method of altering the sRNA population in a sperm, comprising contacting the sperm with a vesicle comprising an epididymosome loaded with a molecular cargo comprising a synthetic sRNA to produce a sperm having an altered sRNA population, wherein the sperm having an altered sRNA population is capable of fertilizing an oocyte.

2. The method of claim 1, wherein the sRNA is selected from the group consisting of a siRNA, a miRNA, a piRNA, a snoRNA, a srRNA, a U-RNA, and a tRNA fragment.

3. The method of claim 1, wherein the sRNA is a tRNA fragment selected from the group consisting of a tRNA-Gly-CCC fragment, a tRNA-Gly-TCC fragment, a tRNA-Gly-GCC fragment, a tRNA-Val-CAC fragment, a tRNA-Glu-CTC fragment, a tRNA-Lys-CTT fragment, and a tRNA-His-GTG fragment.

4. The method of claim 1, wherein the epididymosome is selected from the group consisting of caput epididymosome, corpus epididymosome and cauda epididymosome.

5. The method of claim 1, wherein the resulting sperm comprises an sRNA population comprising increased siRNA, miRNA, piRNA, snoRNA, srRNA, U-RNA, or tRNA fragment content.

6. The method of claim 5, wherein the tRNA fragment content comprises a tRNA-Gly-CCC fragment content, tRNA-Gly-TCC fragment content, tRNA-Gly-GCC fragment content, tRNA-Val-CAC fragment content, tRNA-Glu-CTC fragment content, tRNA-Lys-CTT fragment content, or tRNA-His-GTG fragment content.

7. The method of claim 5, wherein the miRNA is selected from the group consisting of miR-10a/b, miR-141, miR-143, miR-148 and miR-200a.

8. The method of claim 1, wherein the vesicle comprises molecular cargo comprising a transgene.

9. The method of claim 1, wherein the sperm is capable of fertilizing an oocyte in vitro.

10. The method of claim 1, wherein the sperm is capable of fertilizing an oocyte in vivo.

11. The method of claim 1, wherein prior to contacting the sperm, the sperm is frozen.

12. The method of claim 1, wherein the vesicle is loaded with molecular cargo using electroporation.

13. The method of claim 1, wherein the vesicle is loaded with molecular cargo using co-incubation.

* * * * *